(12) United States Patent
Chiang et al.

(10) Patent No.: US 8,513,242 B2
(45) Date of Patent: Aug. 20, 2013

(54) PYRIMIDINE COMPOUNDS AND METHODS OF MAKING AND USING SAME

(75) Inventors: Phoebe Chiang, East Lyme, CT (US); Shomir Ghosh, Brookline, MA (US)

(73) Assignee: Cystic Fibrosis Foundation Therapeutics, Inc., Bethesda, MD (US)

( * ) Notice: Subject to any disclaimer, the term of this patent is extended or adjusted under 35 U.S.C. 154(b) by 13 days.

(21) Appl. No.: 13/139,009

(22) PCT Filed: Dec. 11, 2009

(86) PCT No.: PCT/US2009/067667
§ 371 (c)(1),
(2), (4) Date: Jul. 26, 2011

(87) PCT Pub. No.: WO2010/068863
PCT Pub. Date: Jun. 17, 2010

(65) Prior Publication Data
US 2011/0281873 A1 Nov. 17, 2011

Related U.S. Application Data

(60) Provisional application No. 61/184,356, filed on Jun. 5, 2009, provisional application No. 61/122,187, filed on Dec. 12, 2008.

(51) Int. Cl.
*A61K 31/535* (2006.01)
*A61K 31/505* (2006.01)

(52) U.S. Cl.
USPC .............. 514/235.8; 514/272; 514/275

(58) Field of Classification Search
None
See application file for complete search history.

(56) References Cited

U.S. PATENT DOCUMENTS

| | | | |
|---|---|---|---|
| 2006/0079543 A1 | 4/2006 | Sum et al. | |
| 2009/0221597 A1 | 9/2009 | Ruah et al. | |

FOREIGN PATENT DOCUMENTS

| | | |
|---|---|---|
| EP | 0233461 A2 | 8/1987 |
| JP | 2005-145956 A | 6/2005 |
| WO | WO-01/00214 A1 | 1/2001 |
| WO | WO-02/083667 A2 | 10/2002 |
| WO | WO-02/102800 A1 | 12/2002 |
| WO | WO-03/000682 A1 | 1/2003 |
| WO | WO-03/056329 A2 | 7/2003 |
| WO | WO-2004/016597 A2 | 2/2004 |
| WO | WO-2004/089913 A1 | 10/2004 |
| WO | WO-2004/110452 A1 | 12/2004 |
| WO | WO-2004/111014 A1 | 12/2004 |
| WO | WO-2005/040135 A1 | 5/2005 |
| WO | WO-2005/075435 A1 | 8/2005 |
| WO | WO-2006/066172 A1 | 6/2006 |
| WO | WO-2006/127588 A2 | 11/2006 |
| WO | WO-2007/021982 A2 | 2/2007 |
| WO | WO-2007/056341 A1 | 5/2007 |
| WO | WO-2008/092199 A1 | 8/2008 |
| WO | WO 2008/098058 * | 8/2008 |
| WO | WO-2009/076593 A1 | 6/2009 |
| WO | WO-2010/068863 A2 | 6/2010 |
| WO | WO-2010/151747 A1 | 12/2010 |
| WO | WO-2011/008931 A2 | 1/2011 |

OTHER PUBLICATIONS

CAS RN 31408-52-3 (entered into STN on Nov. 16, 1984).*
Huang, et. al. (2009) "Molecular modeling of the heterodimer of human CFTR's nucleotide-binding domains using a protein-protein docking approach.," *J. Mol. Graph. Model.*, vol. 27(7), pp. 822-828.
International Search Report and Written Opinion, International Patent Application No. PCT/US2009/067667, mailed on Sep. 10, 2010 (10 pages).
International Search Report and Written Opinion, International Patent Application No. PCT/US2010/039963, mailed on Oct. 19, 2010 (9 pages).
International Search Report and Written Opinion, International Patent Application No. PCT/US2010/042103, mailed on Feb. 8, 2012 (10 pages).
Nagarajan et al. (2009) "IKKbeta inhibitors identification part I: Homology model assisted structure based virtual screening.," *Bioorganic & Medicinal Chemistry*, vol. 17(7), pp. 2759-2766. (Abstract only).
Paul et al. (1993) "Preparation of substituted N-phenyl-4-aryl-2-pyrimidinamines as mediator release inhibitors.," Journal of Medicinal Chemistry, vol. 36(19), pp. 2716-2725. (Abstract only).

* cited by examiner

*Primary Examiner* — Craig Ricci
(74) *Attorney, Agent, or Firm* — Goodwin Procter LLP

(57) ABSTRACT

Disclosed herein are pyrimidinyl compounds that are contemplated to be modulators of cystic fibrosis transmembrane regulators (CFTR), and methods of making and using same. Also provided are pharmaceutical compositions and methods of treating disorders associated with cystic fibrosis transmembrane regulators, such as airway inflammation, cystic fibrosis, and the like.

13 Claims, No Drawings

PYRIMIDINE COMPOUNDS AND METHODS OF MAKING AND USING SAME

RELATED APPLICATIONS

This application is a national stage of International (PCT) Patent Application Serial No. PCT/US2009/067667, filed Dec. 11, 2009, and published under PCT Article 21(2) in English, which claims the benefit of and priority to U.S. Provisional Patent Application Ser. No. 61/122,187, filed Dec. 12, 2008, and U.S. Provisional Patent Application Ser. No. 61/184,356, filed Jun. 5, 2009; the contents of each of which are hereby incorporated by reference.

BACKGROUND

The cystic fibrosis transmembrane regulator (CFTR), is a protein of approximately 1480 amino acids made up of two repeated elements, each having six transmembrane segments and a nucleotide binding domain. Based on its predicted domain structure, CFTR is a member or a class of related proteins which includes the multi-drug resistance (MDR) or P-glycoprotein, bovine adenyl cyclase, the yeast STE6 protein as well as several bacterial amino acid transport proteins. Proteins in this group, characteristically, are involved in pumping molecules into or out of cells. CFTR has been postulated to regulate the outward flow of anions from epithelial cells in response to phosphorylation by cyclic AMP-dependent protein kinase or protein kinase C.

Cystic fibrosis (CF) is a lethal hereditary autosomal recessive disease which is caused by mutations in the gene coding for the CFTR $Cl^-$-channel. By far the most common disease-causing mutation is the deletion of the codon for phenylalanine 508 ($\Delta$F508) in the primary sequence of wild type CFTR. Over 90% of patients carry at least one allele of the $\Delta$F508 CFTR mutant gene. The gene product from this mutant gene is a CFTR $Cl^-$-channel that is poorly processed within the cell: most of the mutant protein is incorrectly or incompletely folded and becomes targeted to endoplasmic reticulum-associated degradation (ERAD). The few mutant $Cl^-$-channels that pass the quality control or simply escape the ER before they are degraded will mature through the golgi and eventually are incorporated into the plasma membrane. These are thought to represent <5% of the level observed in cells expressing wild type CFTR, resulting in a commensurate low total whole-cell $Cl^-$-conductance. In addition to the much lower number of channels in the plasma membrane, the open probability of the individual channel proteins is ~3-fold reduced compared to wild type CFTR.

For over a decade, efforts have been ongoing to identify small molecule drugs that can restore the cell CFTR $Cl^-$-conductance to levels high enough to ameliorate the effects of CF. These include correctors of $\Delta$F508 CFTR, compounds that can improve the intracellular processing, and potentiators, compounds which increase the open probability of mutant CFTR channels at the cell surface.

A small molecule dual-acting potentiator-corrector is expected to be of great benefit for the treatment of most CF patients. To date, it has proven difficult to develop compounds acting solely by correction of the intracellular processing that can sufficiently increase the number of channels in the cell surface to overcome the disease-causing deficiency in $Cl^-$-conductance. On the other hand, potentiation, i.e., increase of open probability, of only the mutant channels at the cell surface will not sufficiently restore $Cl^-$-conductance for most CF patients. A dual-acting potentiator-corrector molecule would mechanistically combine aspects of both corrector and potentiator compounds: the number of CFTR channels at the surface and the channel open probability are increased in parallel.

SUMMARY

Provided herein are compounds contemplated to be CFTR modulators, and their use as, for example, medicinal agents. Also provided are pharmaceutical compositions comprising at least one disclosed compound, or a pharmaceutically acceptable salt, prodrug or N-oxide thereof, and a pharmaceutically acceptable carrier.

Accordingly, one aspect of the invention provides a compound of formula I:

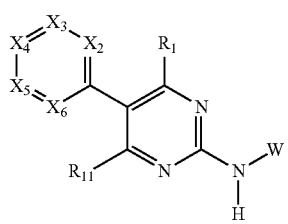

including a pharmaceutically acceptable salt, prodrug or N-oxide thereof, wherein:

$X_2$ is $CR_2$ or N, $X_3$ is $CR_3$ or N, $X_4$ is $CR_4$ or N, $X_5$ is $CR_5$ or N, and $X_6$ is $CR_6$ or N, where no more than two of $X_2$-$X_6$ are N;

W is $C_1$-$C_{10}$alkyl or $C_4$-$C_{10}$cycloalkyl, each of which are optionally substituted with one or two substituents independently selected from the group consisting of $C_1$-$C_6$alkyl, $C_3$-$C_{10}$cycloalkyl, —$OC_1$-$C_6$ alkyl, —O—$C_3$-$C_{10}$cycloalkyl, —$CF_3$, —OH, and fluoro;

$R_1$ and $R_{11}$ are independently hydrogen, $C_1$-$C_{10}$alkyl, $C_3$-$C_{10}$cycloalkyl, $C_3$-$C_{10}$heterocycloalkyl, aryl, heteroaryl, —Y—$C_1$-$C_{10}$alkyl, —Y—$C_3$-$C_{10}$cycloalkyl, —Y—$(CR_{12}R_{13})_n$-aryl, —Y—$(CR_{12}R_{13})_n$-heteroaryl, —Y-aryl, —Y-heteroaryl, —Y—$C_3$-$C_{10}$heterocycloalkyl, —Y—$(CR_{12}R_{13})_n$—$C_3$-$C_{10}$heterocycloalkyl, —$CF_3$, —CN, —$OCF_2$H, —$OCH_2F$, —$OCF_3$, halogen, —$CONR_7R_{10}$, —$NR_7R_{10}$, —$NR_7COR_8$, or —$NR_7SO_2R_9$;

$R_2$ and $R_6$ are independently hydrogen, F, Br, I, —$CF_3$, —$OCF_3$, —$OCHF_2$, —$OCH_2F$, $C_2$-$C_6$alkyl, $C_3$-$C_{10}$cycloalkyl, $C_3$-$C_{10}$heterocyclyl, —$OC_1$-$C_6$alkyl, —O—$C_3$-$C_{10}$cycloalkyl, —$NR_7COR_8$, —$NR_7SO_2R_9$, —$CONR_7R_{10}$, —$SO_2NR_7R_{10}$, —CN, aryl, heteroaryl, —$NR_7R_{10}$, or —$SO_2R_9$;

$R_3$ and $R_5$ are independently hydrogen, halogen, —$CF_3$, —$OCF_3$, —$OCHF_2$, —$OCH_2F$, $C_1$-$C_6$alkyl, $C_3$-$C_{10}$cycloalkyl, $C_3$-$C_{10}$heterocyclyl, —$OC_1$-$C_6$alkyl, —O—$C_3$-$C_{10}$cycloalkyl, —$CONR_7R_{10}$, —$NR_7COR_8$, —$NR_7SO_2R_9$, —$SO_2NR_7R_{10}$, —CN, aryl, heteroaryl, —$NR_7R_{10}$, or —$SO_2R_9$;

$R_4$ is hydrogen, F, Cl, Br, I, —$CF_3$, —CN, —$OCHF_2$, —$OCH_2F$, —$OCF_3$, $C_1$-$C_{10}$alkyl, $C_3$-$C_{10}$cycloalkyl, $C_3$-$C_{10}$heterocyclyl, —$OC_1$-$C_{10}$alkyl, —$OC_3$-$C_{10}$cycloalkyl, —$OC_3$-$C_{10}$heterocycloalkyl, —$SC_1$-$C_{10}$alkyl, —$SC_3$-$C_{10}$cycloalkyl, —$NR_7SO_2R_9$, —$NR_7COR_8$, —$CONR_7R_{10}$, —$SO_2NR_7R_{10}$, aryl, heteroaryl, —$NR_7R_{10}$, or —$SO_2R_9$; or any two adjacent variables selected from $R_2$, $R_3$, $R_4$, $R_5$, and $R_6$ are taken together to form a cycloalkyl, aryl, heteroaryl or heterocyclyl, optionally substituted by one, two, or three substituents independently selected from the group consisting of alkoxy, alkyl, alkylalkoxy, alkenyl, alkynyl, amido, amino, aryl, cyano, cycloalkyl, haloalkyl, halogen, heteroaryl, heterocyclyl, hydroxyl, and sulfonyl;

$R_7$ and $R_{10}$ are independently hydrogen; or $C_1$-$C_6$alkyl, $C_3$-$C_{10}$cycloalkyl, or $C_3$-$C_{10}$heterocycloalkyl, each of which are optionally substituted with one or two substituents independently selected from the group consisting of $C_1$-$C_3$alkyl, halogen, cyano, hydroxy, and alkoxy; or $R_7$ and $R_{10}$ are taken together to form a heterocyclyl group optionally substituted by one, two, or three substituents independently selected from the group consisting of alkoxy, alkyl, alkenyl, alkynyl, amido, amino, aryl, cyano, cycloalkyl, haloalkyl, halogen, heteroaryl, heterocyclyl, hydroxyl, nitro and sulfonyl; wherein the heterocyclyl is not imidazolyl;

$R_8$ is alkoxy, alkyl, alkenyl, alkynyl, amido, amino, aryl, cycloalkoxy, cycloalkyl, haloalkyl, heteroaryl, or heterocyclyl;

$R_9$ is alkyl, alkenyl, alkynyl, aryl, cycloalkoxy, cycloalkyl, haloalkyl, heteroaryl, or heterocyclyl;

$R_{12}$ and $R_{13}$ each represent independently for each occurrence H, methyl, ethyl, n-propyl, isopropyl, or cyclopropyl; or $R_{12}$ and $R_{13}$ taken together with the atom to which they are attached form a $C_3$-$C_6$cycloalkyl group;

Y is O, S, S(O), or S(O)$_2$;

n is 1, 2, or 3;

where at least one of $R_2$, $R_3$, $R_4$, $R_5$, and $R_6$ is not hydrogen;

where $R_3$ is not morpholino or pyridyl; and where if $R_4$ is —CH$_3$, —OCF$_3$, —OCH$_3$, F, Cl, —CONHnBu, —CONH-cyclopentyl, or —CONH—CH$_2$-phenyl-3-Me, then W is not unsubstituted cyclohexyl or unsubstituted cyclopropyl, or $R_1$ is not hydrogen.

Another aspect of the invention provides a compound of formula II:

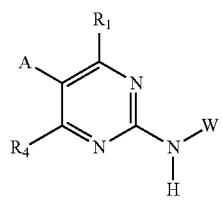

II including a pharmaceutically acceptable salt, prodrug or N-oxide thereof, wherein:

A is one of the following:

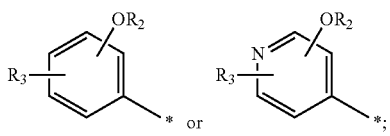

W is $C_1$-$C_{10}$alkyl or $C_4$-$C_{10}$cycloalkyl, each of which is optionally substituted with one or two substituents independently selected from the group consisting of $C_1$-$C_6$alkyl, $C_3$-$C_{10}$cycloalkyl, —OC$_1$-$C_6$alkyl, —O—$C_3$-$C_{10}$cycloalkyl, —CF$_3$, —OH, and fluoro;

$R_1$ and $R_4$ are independently hydrogen, $C_1$-$C_6$alkyl, $C_3$-$C_{10}$cycloalkyl, —OC$_1$-$C_6$alkyl, —O—$C_3$-$C_{10}$cycloalkyl, —O—$C_3$-$C_{10}$heterocycloalkyl, —O—C(R$_8$)(R$_9$)—$C_3$-$C_{10}$heterocycloalkyl, —CF$_3$, —CN, —OCF$_2$H, —OCH$_2$F, —OCF$_3$, halogen, —CONR$_5$R$_6$, —NR$_5$R$_6$, —NR$_5$COR$_6$, —NR$_5$SO$_2$R$_7$, or —SO$_2$R$_7$;

$R_2$ is $C_1$-$C_6$alkyl;

$R_3$ is halogen, —CF$_3$, —OCF$_3$, —OCHF$_2$, —OCH$_2$F, $C_1$-$C_6$alkyl, $C_3$-$C_{10}$cycloalkyl, $C_3$-$C_{10}$heterocyclyl, —OC$_1$-$C_6$alkyl, —O—$C_3$-$C_{10}$cycloalkyl, —O—$C_3$-$C_{10}$heterocycloalkyl, —CONR$_5$R$_6$, —NR$_5$COR$_7$, —NR$_7$SO$_2$R$_7$, —SO$_2$NR$_5$R$_6$, —CN, aryl, heteroaryl, —NR$_5$R$_6$, or —SO$_2$R$_7$;

$R_5$ and $R_6$ are each independently hydrogen; or alkyl or cycloalkyl, each of which is optionally substituted with one or two substituents independently selected from the group consisting of halogen, cyano, hydroxy, and alkoxy; or $R_5$ and $R_6$ are taken together to form a heterocyclyl that is optionally substituted by one, two, or three substituents independently selected from the group consisting of alkoxy, alkyl, alkenyl, alkynyl, amido, amino, aryl, cyano, cycloalkyl, haloalkyl, halogen, heteroaryl, heterocyclyl, hydroxyl, and sulfonyl;

$R_7$ represents independently for each occurrence alkyl, alkenyl, alkynyl, aryl, cycloalkoxy, cycloalkyl, haloalkyl, heteroaryl, or heterocyclyl; and $R_8$ and $R_9$ represent independently hydrogen, methyl, ethyl, n-propyl, isopropyl, or cyclopropyl; or $R_8$ and $R_9$ taken together with the atom to which they are attached form a $C_3$-$C_6$cycloalkyl group.

Another aspect of the invention provides a compound of formula III:

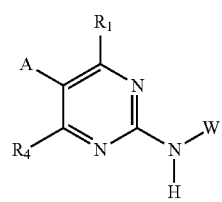

III including a pharmaceutically acceptable salt, prodrug or N-oxide thereof, wherein:

A is

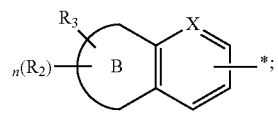

B is heteroaryl or an unsaturated heterocyclyl;

X is C(H) or N;

W is $C_1$-$C_{10}$alkyl or $C_4$-$C_{10}$cycloalkyl, each of which is optionally substituted with one or two substituents independently selected from the group consisting of $C_1$-$C_6$alkyl, $C_3$-$C_{10}$cycloalkyl, —OC$_1$-$C_6$alkyl, —O—$C_3$-$C_{10}$cycloalkyl, —CF$_3$, —OH, and fluoro;

$R_1$ and $R_4$ are independently hydrogen, $C_1$-$C_6$alkyl, $C_3$-$C_{10}$cycloalkyl, —OC$_1$-$C_6$alkyl, —O—$C_3$-$C_{10}$cycloalkyl, —O—$C_3$-$C_{10}$heterocycloalkyl, —O—(CR$_8$R$_9$)$_m$—$C_3$-$C_{10}$heterocycloalkyl, —O-aryl, —CF$_3$, —CN, —OCF$_2$H, —OCH$_2$F, —OCF$_3$, halogen, —CONR$_5$R$_6$, —NR$_5$R$_6$, —NR$_5$COR$_6$, —NR$_5$SO$_2$R$_7$, or —SO$_2$R$_7$;

R$_2$ represents independently for each occurrence halogen, —CF$_3$, —OCF$_3$, —OCHF$_2$, —OCH$_2$F, —CN, C$_1$-C$_6$alkyl, C$_3$-C$_{10}$cycloalkyl, C$_3$-C$_{10}$heterocyclyl, —OC$_1$-C$_6$alkyl, —O—C$_3$-C$_{10}$cycloalkyl, —O—C$_3$-C$_{10}$heterocyclyl, —CONR$_5$R$_6$, —NR$_5$COR$_7$, —NR$_7$SO$_2$R$_7$, —SO$_2$NR$_5$R$_6$, —CN, aryl, heteroaryl, —NR$_5$R$_6$, or —SO$_2$R$_7$;

R$_3$ is hydrogen, C$_1$-C$_6$alkyl, or C$_3$-C$_6$cycloalkyl;

R$_5$ and R$_6$ are independently hydrogen; or alkyl or cycloalkyl, each of which is optionally substituted with one or two substituents independently selected from the group consisting of halogen, cyano, hydroxy, nitro, and alkoxy; or R$_5$ and R$_6$ are taken together to form a heterocyclyl that is optionally substituted by one, two, or three substituents independently selected from the group consisting of alkoxy, alkyl, alkenyl, alkynyl, amido, amino, aryl, cyano, cycloalkyl, haloalkyl, halogen, heteroaryl, heterocyclyl, hydroxyl, nitro and sulfonyl;

R$_7$ represents independently for each occurrence alkyl, alkenyl, alkynyl, amido, amino, aryl, cycloalkoxy, cycloalkyl, haloalkyl, heteroaryl, or heterocyclyl;

R$_8$ and R$_9$ each represent independently for each occurrence H, methyl, ethyl, or n-propyl, or isopropyl; or R$_8$ and R$_9$ taken together with the atom to which they are attached form a C$_3$-C$_6$-cycloalkyl group;

m is 1, 2, or 3; and n is 0, 1, or 2.

Also provided herein are methods of treating airway inflammation, such as cystic fibrosis, comprising administering to a subject in need thereof a therapeutically effective amount of a compound described herein, e.g., a compound of formula I, Ia, II, or III. Also contemplated herein are compositions that include a compound described herein, e.g., a compound of formula I, Ia, II, or III, and a pharmaceutically acceptable excipient.

The disclosure further provides methods of modulating the activity of one or more cystic fibrosis transmembrane regulators comprising, for example, exposing said receptor to a compound described herein, e.g., a compound of formula I, Ia, II, or III.

Also provided herein are methods of treating a disease associated with expression or activity of one or more cystic fibrosis transmembrane regulators in a subject comprising administering to the subject a therapeutically effective amount of a disclosed compound. For example, provided herein are methods of treating chronic obstructive pulmonary disease, dry eye disease, and Sjögren's syndrome, comprising administering a compound described herein, e.g., a compound of formula I, Ia, II, or III. Also provided are use of a compound described herein for therapy and/or the manufacture of a medicament for the treatment of disease associated with cystic fibrosis transmembrane regulators.

DETAILED DESCRIPTION

The features and other details of the disclosure will now be more particularly described. Before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

I. DEFINITIONS

"Treating" includes any effect, e.g., lessening, reducing, modulating, or eliminating, that results in the improvement of the condition, disease, disorder and the like.

The term "aldehyde" or "formyl" as used herein refers to the radical —CHO.

The term "alkanoyl" as used herein refers to a radical —O—CO-alkyl.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C$_2$-C$_{12}$alkenyl, C$_2$-C$_{10}$alkenyl, and C$_2$-C$_6$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkoxy" as used herein refers to an alkyl group attached to an oxygen (—O-alkyl-). Exemplary alkoxy groups include, but are not limited to, groups with an alkyl, alkenyl or alkynyl group of 1-12, 1-8, or 1-6 carbon atoms, referred to herein as C$_1$-C$_{12}$alkoxy, C$_1$-C$_8$alkoxy, and C$_1$-C$_6$alkoxy, respectively. Exemplary alkoxy groups include, but are not limited to methoxy, ethoxy, etc. Similarly, exemplary "alkenoxy" groups include, but are not limited to vinyloxy, allyloxy, butenoxy, etc.

The term "alkyl" as used herein refers to a saturated straight or branched hydrocarbon, such as a straight or branched group of 1-12, 1-10, or 1-6 carbon atoms, referred to herein as C$_1$-C$_{12}$alkyl, C$_1$-C$_{10}$alkyl, and C$_1$-C$_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

Unless specified otherwise, alkyl, alkenyl and alkynyl groups are optionally substituted or interrupted by at least one group selected from alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. In certain embodiments, the alkyl, alkenyl and alkynyl groups are not substituted or interrupted, i.e., they are unsubstituted.

The term "alkynyl" as used herein refers to an unsaturated straight or branched hydrocarbon having at least one carbon-carbon triple bond, such as a straight or branched group of 2-12, 2-8, or 2-6 carbon atoms, referred to herein as C$_2$-C$_{12}$alkynyl, C$_2$-C$_8$alkynyl, and C$_2$-C$_6$alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl, etc.

The term "amide" or "amido" as used herein refers to a radical of the form —R$_a$C(O)N(R$_b$)—, —R$_a$C(O)N(R$_b$)R$_c$—, —C(O)NR$_b$R$_c$, or —C(O)NH$_2$, wherein R$_a$, R$_b$ and R$_c$ are each independently selected from alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, and nitro. The amide can be attached to another group through the carbon, the nitrogen, $R_b$, $R_c$, or $R_a$. The amide also may be cyclic, for example $R_b$ and $R_c$, $R_a$ and $R_b$, or $R_a$ and $R_c$ may be joined to form a 3- to 12-membered ring, such as a 3- to 10-membered ring or a 5- to 6-membered ring. The term "carboxamido" refers to the structure —C(O)NR$_b$R$_c$.

The term "amidino" as used herein refers to a radical of the form —C(=NR)NR'R" where R, R', and R" can each independently be selected from alkyl, alkenyl, alkynyl, amide, aryl, arylalkyl, cyano, cycloalkyl, haloalkyl, heteroaryl, heterocyclyl, hydroxyl, ketone and nitro.

The term "amine" or "amino" as used herein refers to a radical of the form —NR$_d$R$_e$, —N(R$_d$)R$_e$—, or —R$_e$N(R$_d$)R$_f$— where R$_d$, R$_e$, and R$_f$ are independently selected from alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, and nitro. The amino can be attached to the parent molecular group through the nitrogen, R$_d$, R$_e$ or R$_f$. The amino also may be cyclic, for example any two of Rd, Re or Rf may be joined together or with the N to form a 3- to 12-membered ring, e.g., morpholino or piperidinyl. The term amino also includes the corresponding quaternary ammonium salt of any amino group, e.g., —[N(Rd)(Re)(Rf)]+. Exemplary amino groups include aminoalkyl groups, wherein at least one of R$_d$, R$_e$, or R$_f$ is an alkyl group.

The term "aryl" as used herein refers to refers to a mono-, bi-, or other multi-carbocyclic, aromatic ring system. Unless specified otherwise, the aromatic ring is optionally substituted at one or more ring positions with substituents selected from alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. In certain embodiments, the aryl group is not substituted, i.e., it is unsubstituted.

The term "arylalkyl" as used herein refers to an aryl group having at least one alkyl substituent, e.g. -aryl-alkyl-. Exemplary arylalkyl groups include, but are not limited to, arylalkyls having a monocyclic aromatic ring system, wherein the ring comprises 6 carbon atoms. For example, "phenylalkyl" includes phenylC$_4$alkyl, benzyl, 1-phenylethyl, 2-phenylethyl, etc.

The term "azido" as used herein refers to the radical —N$_3$.

The term "carbamate" as used herein refers to a radical of the form —R$_g$OC(O)N(R$_h$)—, —R$_g$OC(O)N(R$_h$)R$_i$—, or —OC(O)NR$_h$R$_i$, wherein R$_g$, R$_h$ and R$_i$ are each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, sulfide, sulfonyl, and sulfonamide. Exemplary carbamates include, but are not limited to, arylcarbamates or heteroaryl carbamates, e.g., wherein at least one of R$_g$, R$_h$ and R$_i$ are independently selected from aryl or heteroaryl, such as phenyl and pyridinyl.

The term "carbonyl" as used herein refers to the radical —C(O)—.

The term "carboxamido" as used herein refers to the radical —C(O)NRR', where R and R' may be the same or different. R and R' may be selected from, for example, alkyl, aryl, arylalkyl, cycloalkyl, formyl, haloalkyl, heteroaryl and heterocyclyl.

The term "carboxy" as used herein refers to the radical —COOH or its corresponding salts, e.g. —COONa, etc.

The term "cyano" as used herein refers to the radical —CN.

The term "cycloalkoxy" as used herein refers to a cycloalkyl group attached to an oxygen.

The term "cycloalkyl" as used herein refers to a monovalent saturated or unsaturated cyclic, bicyclic, or bridged cyclic (e.g., adamantyl)hydrocarbon group of 3-12, 3-8, 4-8, or 4-6 carbons, referred to herein, e.g., as "C$_{4-8}$cycloalkyl," derived from a cycloalkane. Exemplary cycloalkyl groups include, but are not limited to, cyclohexanes, cyclohexenes, cyclopentanes, cyclopentenes, cyclobutanes and cyclopropanes. Unless specified otherwise, cycloalkyl groups are optionally substituted with alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. Cycloalkyl groups can be fused to other cycloalkyl, aryl, or heterocyclyl groups. In certain embodiments, the cycloalkyl group is not substituted, i.e., it is unsubstituted.

The term "ether" refers to a radical having the structure —R$_l$O—R$_m$—, where R$_l$ and R$_m$ can independently be alkyl, aryl, cycloalkyl, heterocyclyl, or ether. The ether can be attached to the parent molecular group through R$_l$ or R$_m$. Exemplary ethers include, but are not limited to, alkoxyalkyl and alkoxyaryl groups. Ether also includes polyethers, e.g., where one or both of R$_l$ and R$_m$ are ethers.

The terms "halo" or "halogen" or "Hal" as used herein refer to F, Cl, Br, or I.

The term "haloalkyl" as used herein refers to an alkyl group substituted with one or more halogen atoms.

The terms "heteroaryl" as used herein refers to a 5-15 membered mono-, bi-, or other multi-cyclic, aromatic ring system containing one or more heteroatoms, for example one to four heteroatoms, such as nitrogen, oxygen, and sulfur. Heteroaryls can also be fused to non-aromatic rings. Unless specified otherwise, the heteroaryl ring is optionally substituted at one or more positions with such substituents as described above, as for example, alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. Illustrative examples of heteroaryl groups include, but are not limited to, acridinyl, benzimidazolyl, benzofuryl, benzothiazolyl, benzothienyl, benzoxazolyl, carbazolyl, carbolinyl, cinnolinyl, furazanyl, furyl, imidazolyl, indazolyl, indolizinyl, indolyl, isobenzofuryl, isoindolyl, isoquinolinyl, isothiazolyl, isoxazolyl, naphthyridinyl, oxadiazolyl, oxazolyl, phenanthridinyl, phenanthrolinyl, phenarsazinyl, phenazinyl, phenothiazinyl, phenoxazinyl, phthalazinyl, pteridinyl, purinyl, pyrazinyl, pyrazolyl, pyrazyl, pyridazinyl, pyridinyl, pyrimidilyl, pyrimidyl, pyrrolyl, quinolinyl, quinolizinyl, quinoxalinyl, quinoxaloyl, quinazolinyl, tetrazolyl, thiadiazolyl, thianthrenyl, thiazolyl, thienyl, thiophenyl, triazinyl, (1,2,3)- and (1,2,4)-triazolyl, and the like. Exemplary heteroaryl groups include, but are not limited to, a monocyclic aromatic ring, wherein the ring comprises 2 to 5 carbon atoms and 1 to 3 heteroatoms. In certain embodiments, the heteroaryl group is not substituted, i.e., it is unsubstituted.

The terms "heterocyclyl" or "heterocyclic group" are art-recognized and refer to saturated or partially unsaturated 3- to 10-membered ring structures, alternatively 3- to 7-membered rings, whose ring structures include one to four heteroatoms, such as nitrogen, oxygen, and sulfur. Heterocycles may also be mono-, bi-, or other multi-cyclic ring systems. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isoxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. Unless specified otherwise, the heterocyclic ring is optionally substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. In certain embodiments, the heterocyclcyl group is not substituted, i.e., it is unsubstituted.

The term "heterocycloalkyl" is art-recognized and refers to a saturated heterocyclyl group as defined above.

The term "heterocyclylalkoxy" as used herein refers to a heterocyclyl attached to an alkoxy group.

The term "heterocyclyloxyalkyl" refers to a heterocyclyl attached to an oxygen (—O—), which is attached to an alkyl group.

The terms "hydroxy" and "hydroxyl" as used herein refers to the radical —OH.

The term "hydroxyalkyl" as used herein refers to a hydroxy radical attached to an alkyl group.

The term "imino" as used herein refers to the radical —C(=N)—R″, where R″ can be, for example, alkyl, alkenyl, alkynyl, aryl, arylalkyl, cycloalkyl, ether, haloalkyl, heteroaryl, heterocyclyl, and ketone.

The term "nitro" as used herein refers to the radical —NO$_2$.

The term "phenyl" as used herein refers to a 6-membered carbocyclic aromatic ring. The phenyl group can also be fused to a cyclohexane or cyclopentane ring. Unless specified otherwise, phenyl is optionally substituted with one or more substituents including alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. In certain embodiments, the phenyl group is not substituted, i.e., it is unsubstituted.

The term "phosphate" as used herein refers to the radical —OP(O)(OR$_{aa}$)$_2$ or its anions. The term "phosphanato" refers to the radical —P(O)(OR$_{aa}$)$_2$ or its anions. The term "phosphinato" refers to the radical —PR$_{aa}$(O)(OR$_{aa}$) or its anion, where each R$_{aa}$ can be selected from, for example, alkyl, alkenyl, alkynyl, aryl, arylalkyl, cycloalkyl, hydrogen, haloalkyl, heteroaryl, and heterocyclyl.

The term "sulfate" as used herein refers to the radical —OS(O)(OR$_{aa}$)$_2$ or its anions, where R$_{aa}$ is defined above.

The term "sulfonamide" or "sulfonamido" as used herein refers to a radical having the structure —N(R$_r$)—S(O)$_2$—R$_s$— or —S(O)$_2$—N(R$_r$)R$_s$, where R$_r$, and R$_s$ can be, for example, hydrogen, alkyl, aryl, cycloalkyl, and heterocyclyl. Exemplary sulfonamides include alkylsulfonamides (e.g., where R$_s$ is alkyl), arylsulfonamides (e.g., where R$_s$ is aryl), cycloalkyl sulfonamides (e.g., where R$_s$ is cycloalkyl), and heterocyclyl sulfonamides (e.g., where R$_s$ is heterocyclyl), etc.

The term "sulfonyl" as used herein refers to a radical having the structure R$_u$SO$_2$—, where R$_u$ can be alkyl, aryl, cycloalkyl, and heterocyclyl, e.g., alkylsulfonyl. The term "alkylsulfonyl" as used herein refers to an alkyl group attached to a sulfonyl group.

The term "sulfide" as used herein refers to the radical having the structure R$_z$S—, where R$_z$ can be alkoxy, alkyl, alkenyl, alkynyl, amide, amino, aryl, arylalkyl, carbamate, carboxy, cycloalkyl, ester, ether, formyl, haloalkyl, heteroaryl, heterocyclyl, and ketone. The term "alkylsulfide" as used herein refers to an alkyl group attached to a sulfur atom. Exemplary sulfides include "thio," which as used herein refers to an —SH radical.

The term "thiocarbonyl" or "thiocarboxy" as used herein refers to compounds and moieties which contain a carbon connected with a double bond to a sulfur atom.

"Pharmaceutically or pharmacologically acceptable" include molecular entities and compositions that do not produce an adverse, allergic or other untoward reaction when administered to an animal, or a human, as appropriate. "For human administration, preparations should meet sterility, pyrogenicity, general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include to any animal, including mammals, preferably mice, rats, other rodents, rabbits, dogs, cats, swine, cattle, sheep, horses, or primates, and most preferably humans. The compounds of the invention can be administered to a mammal, such as a human, but can also be other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in whom modulation of cystic fibrosis transmembrane regulators is desired.

"Modulation" includes antagonism (e.g., inhibition), agonism, partial antagonism and/or partial agonism. Modulators may be dual acting corrector/potentiator compounds. In one embodiment, a modulator is a corrector compound. In another embodiment, a modulator is a potentiator compound.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in the prevention of or a decrease in the symptoms associated with a disease associated with cystic fibrosis transmembrane regulators.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well known asymmetric synthetic methods.

Geometric isomers can also exist in the compounds of the present invention. The symbol ⎓ denotes a bond that may be a single, double or triple bond as described herein. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a polymorph. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the e.g., Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms, such as through hydrolysis in blood. For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy) ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, if a compound of the invention contains an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy) ethyl, 1-methyl-1-(($C_1$-$C_6$)alkanoyloxy)ethyl ($C_1$-$C_6$) alkoxycarbonyloxymethyl, N—($C_1$-$C_6$)alkoxycarbonylaminomethyl, succinoyl, ($C_1$-$C_6$)alkanoyl, α-amino($C_1$-$C_4$) alkanoyl, arylacyl and α-aminoacyl, or α-aminoacyl-α-aminoacyl, where each α-aminoacyl group is independently selected from the naturally occurring L-amino acids, P(O) (OH)$_2$, —P(O)(O($C_1$-$C_6$)alkyl)$_2$ or glycosyl (the radical resulting from the removal of a hydroxyl group of the hemiacetal form of a carbohydrate).

If a compound of the invention incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl-natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$)alkyl and Y$^3$ is ($C_1$-$C_6$)alkyl, carboxy($C_1$-$C_6$)alkyl, amino($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino, morpholino, piperidin-1-yl or pyrrolidin-1-yl.

II. PYRIMIDINYL COMPOUNDS & PHARMACEUTICAL COMPOSITIONS

One aspect of the invention provides a compound of formula I:

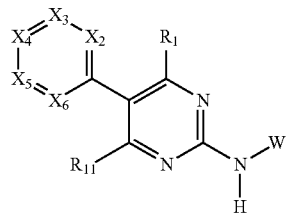

I including a pharmaceutically acceptable salt, prodrug or N-oxide thereof, wherein:

$X_2$ is $CR_2$ or N, $X_3$ is $CR_3$ or N, $X_4$ is $CR_4$ or N, $X_5$ is $CR_5$ or N, and $X_6$ is $CR_6$ or N, where no more than two of $X_2$-$X_6$ are N;

W is $C_1$-$C_{10}$alkyl or $C_4$-$C_{10}$cycloalkyl, each of which are optionally substituted with one or two substituents independently selected from the group consisting of $C_1$-$C_6$alkyl, $C_3$-$C_{10}$cycloalkyl, —O$C_1$-$C_6$alkyl, —O—$C_3$-$C_{10}$cycloalkyl, —CF$_3$, —OH, and fluoro;

$R_1$ and $R_{11}$ are independently hydrogen, $C_1$-$C_{10}$alkyl, $C_3$-$C_{10}$cycloalkyl, $C_3$-$C_{10}$heterocycloalkyl, aryl, heteroaryl, —Y—$C_1$-$C_{10}$alkyl, —Y—$C_3$-$C_{10}$cycloalkyl, —Y—(CR$_{12}$R$_{13}$)$_n$-aryl, —Y—(CR$_{12}$R$_{13}$)$_n$-heteroaryl, —Y-aryl, —Y-heteroaryl, —Y—$C_3$-$C_{10}$heterocycloalkyl, —Y—(CR$_{12}$R$_{13}$)$_n$—$C_3$-$C_{10}$heterocycloalkyl, —CF$_3$, —CN, —OCF$_2$H, —OCH$_2$F, —OCF$_3$, halogen, —CONR$_7$R$_{10}$, —NR$_7$R$_{10}$, —NR$_7$COR$_8$, or —NR$_7$SO$_2$R$_9$;

$R_2$ and $R_6$ are independently hydrogen, F, Br, I, —CF$_3$, —OCF$_3$, —OCHF$_2$, —OCH$_2$F, $C_2$-$C_6$alkyl, $C_3$-$C_{10}$cycloalkyl, $C_3$-$C_{10}$heterocyclyl, —OC$_1$-$C_6$alkyl, —O—$C_3$-$C_{10}$cycloalkyl, —NR$_7$COR$_8$, —NR$_7$SO$_2$R$_9$, —CONR$_7$R$_{10}$, —SO$_2$NR$_7$R$_{10}$, —CN, aryl, heteroaryl, —NR$_7$R$_{10}$, or —SO$_2$R$_9$;

$R_3$ and $R_5$ are independently hydrogen, halogen, —CF$_3$, —OCF$_3$, —OCHF$_2$, —OCH$_2$F, $C_1$-$C_6$ alkyl, $C_3$-$C_{10}$cycloalkyl, $C_3$-$C_{10}$heterocyclyl, —OC$_1$-$C_6$ alkyl, —O—$C_3$-$C_{10}$cycloalkyl, —CONR$_7$R$_{10}$, —NR$_7$COR$_8$, —NR$_7$SO$_2$R$_9$, —SO$_2$NR$_7$R$_{10}$, —CN, aryl, heteroaryl, —NR$_7$R$_{10}$, or —SO$_2$R$_9$;

$R_4$ is hydrogen, F, Cl, Br, I, —CF$_3$, —CN, —OCHF$_2$, —OCH$_2$F, —OCF$_3$, $C_1$-$C_{10}$alkyl, $C_3$-$C_{10}$cycloalkyl, $C_3$-$C_{10}$heterocyclyl, —OC$_1$-$C_{10}$alkyl, —OC$_3$-$C_{10}$cycloalkyl, —OC$_3$-$C_{10}$heterocycloalkyl, —SC$_1$-$C_{10}$alkyl, —SC$_3$-$C_{10}$cycloalkyl, —NR$_7$SO$_2$R$_9$, —NR$_7$COR$_8$, —CONR$_7$R$_{10}$, —SO$_2$NR$_7$R$_{10}$, aryl, heteroaryl, —NR$_7$R$_{10}$, or —SO$_2$R$_9$; or any two adjacent variables selected from $R_2$, $R_3$, $R_4$, $R_5$, and $R_6$ are taken together to form a cycloalkyl, aryl, heteroaryl or heterocyclyl, optionally substituted by one, two, or three substituents independently selected from the group consisting of alkoxy, alkyl, alkylalkoxy, alkenyl, alkynyl, amido, amino, aryl, cyano, cycloalkyl, haloalkyl, halogen, heteroaryl, heterocyclyl, hydroxyl, and sulfonyl;

$R_7$ and $R_{10}$ are independently hydrogen; or $C_1$-$C_6$alkyl, $C_3$-$C_{10}$cycloalkyl, or $C_3$-$C_{10}$heterocycloalkyl, each of which are optionally substituted with one or two substituents independently selected from the group consisting of $C_1$-$C_3$alkyl, halogen, cyano, hydroxy, and alkoxy; or $R_7$ and $R_{10}$ are taken together to form a heterocyclyl group optionally substituted by one, two, or three substituents independently selected from the group consisting of alkoxy, alkyl, alkenyl, alkynyl, amido, amino, aryl, cyano, cycloalkyl, haloalkyl, halogen, heteroaryl, heterocyclyl, hydroxyl, nitro and sulfonyl; wherein the heterocyclyl is not imidazolyl;

$R_8$ is alkoxy, alkyl, alkenyl, alkynyl, amido, amino, aryl, cycloalkoxy, cycloalkyl, haloalkyl, heteroaryl, or heterocyclyl;

$R_9$ is alkyl, alkenyl, alkynyl, aryl, cycloalkoxy, cycloalkyl, haloalkyl, heteroaryl, or heterocyclyl;

$R_{12}$ and $R_{13}$ each represent independently for each occurrence H, methyl, ethyl, n-propyl, isopropyl, or cyclopropyl; or $R_{12}$ and $R_{13}$ taken together with the atom to which they are attached form a $C_3$-$C_6$cycloalkyl group;

Y is O, S, S(O), or S(O)$_2$;

n is 1, 2, or 3;

where at least one of $R_2$, $R_3$, $R_4$, $R_5$, and $R_6$ is not hydrogen;

where $R_3$ is not morpholino or pyridyl; and where if $R_4$ is —$CH_3$, —$OCF_3$, —$OCH_3$, F, Cl, —CONHnBu, —CONH-cyclopentyl, or —CONH—$CH_2$-phenyl-3-Me, then W is not unsubstituted cyclohexyl or unsubstituted cyclopropyl, or $R_1$ is not hydrogen.

In certain embodiments, $X_2$ is $CR_2$, $X_3$ is $CR_3$ or N, $X_4$ is $CR_4$, $X_5$ is $CR_5$, and $X_6$ is $CR_6$. In certain embodiments, W is $C_4$-$C_{10}$cycloalkyl optionally substituted with one or two substituents independently selected from the group consisting of $C_1$-$C_6$alkyl and fluoro. In certain embodiments, W is $C_4$-$C_{10}$cycloalkyl optionally substituted with one or two $C_1$-$C_6$alkyl substituents. In certain embodiments, W is $C_4$-$C_{10}$cycloalkyl optionally substituted with one or two trifluoromethyl groups. In certain embodiments, W is cyclohexyl substituted with $C_1$-$C_6$alkyl. In certain embodiments, W is cyclohexyl optionally substituted with one or two trifluoromethyl groups. In certain embodiments, W is adamantyl. In certain embodiments, Y is O. In certain embodiments, $R_1$ and $R_{11}$ are independently hydrogen, $C_1$-$C_6$alkyl, $C_3$-$C_{10}$cycloalkyl, $C_3$-$C_{10}$heterocycloalkyl, —$OC_1$-$C_6$alkyl, —O—$C_3$-$C_{10}$cycloalkyl, —O—$C_3$-$C_{10}$heterocycloalkyl, —O—C($R_{12}$)($R_{13}$)—$C_3$-$C_{10}$heterocycloalkyl, —O-aryl, —O-heteroaryl, —O—C($R_{12}$)($R_{13}$)-aryl, or —O—C($R_{12}$)($R_{13}$)-heteroaryl. In certain embodiments, $R_1$ is methoxy, ethoxy, propoxy, t-butoxy, cyclobutoxy, cyclopropylmethoxy, morpholinyl, —O-tetrahydrofuranyl, —O—$CH_2$— tetrahydrofuranyl, —O-tetrahydropyranyl, —O—$CH_2$-tetrahydropyranyl, —O-oxetanyl, —O—$CH_2$-oxetanyl, —N($CH_3$)$_2$, phenoxy or benzyloxy; and $R_{11}$ is hydrogen or methyl. In certain embodiments, $R_1$ and $R_{11}$ are independently hydrogen, $C_1$-$C_6$alkyl, —$OC_1$-$C_6$alkyl, —O—$C_3$-$C_{10}$cycloalkyl, or —O—$C_3$-$C_{10}$heterocycloalkyl. In certain embodiments, $R_1$ is methoxy, ethoxy, propoxy, —O-tetrahydrofuranyl, or —O-tetrahydropyranyl; and $R_{11}$ is hydrogen. In certain embodiments, $R_1$ and $R_{11}$ are hydrogen. In certain embodiments, $R_2$ and $R_6$ are hydrogen. In certain embodiments, $R_3$ and $R_5$ are hydrogen or halogen. In certain embodiments, $R_4$ is —$CF_3$, —$OCHF_2$, —$OCH_2F$, —$OCF_3$, $C_1$-$C_6$alkyl, $C_3$-$C_{10}$cycloalkyl, $C_3$-$C_{10}$heterocyclyl, —$OC_1$-$C_6$alkyl, —$OC_3$-$C_{10}$cycloalkyl, —$OC_3$-$C_{10}$heterocycloalkyl, or —$NR_7R_{10}$. In certain embodiments, $R_4$ is —$CF_3$, —$OCHF_2$, —$OCH_2F$, —$OCF_3$, $C_1$-$C_6$alkyl, $C_3$-$C_{10}$cycloalkyl, $C_3$-$C_{10}$heterocyclyl, —$OC_1$-$C_6$alkyl, —$OC_3$-$C_{10}$cycloalkyl, or —$OC_3$-$C_{10}$heterocycloalkyl. In certain embodiments, $R_7$ and $R_{10}$ are independently hydrogen, methyl, ethyl, n-propyl, isopropyl, cyclopropyl, cyclobutyl, cyclopentyl, or cyclohexyl. In certain embodiments, $R_7$ and $R_{10}$ are independently hydrogen, methyl, ethyl or propyl. In certain embodiments, $R_8$ and $R_9$ are $C_1$-$C_6$alkyl. In certain embodiments, $R_8$ and $R_9$ are independently methyl, ethyl, propyl, butyl, pentyl, or hexyl.

Another aspect of the invention provides a compound of formula Ia:

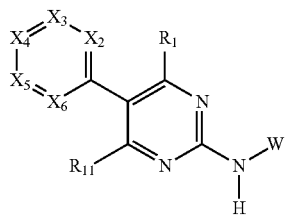

Ia including a pharmaceutically acceptable salt, prodrug or N-oxide thereof, wherein:

$X_2$ is $CR_2$ or N, $X_3$ is $CR_3$ or N, $X_4$ is $CR_4$ or N, $X_5$ is $CR_5$ or N, and $X_6$ is $CR_6$ or N, where no more than two of $X_2$-$X_6$ are N;

W is $C_1$-$C_{10}$alkyl or $C_4$-$C_{10}$cycloalkyl, each of which are optionally substituted with one or two substituents independently selected from the group consisting of $C_1$-$C_6$alkyl, $C_3$-$C_{10}$cycloalkyl, —$OC_1$-$C_6$alkyl, —O—$C_3$-$C_{10}$cycloalkyl, —$CF_3$, and fluoro;

$R_1$ and $R_{11}$ are independently hydrogen, $C_1$-$C_6$alkyl, $C_3$-$C_{10}$cycloalkyl, —$OC_1$-$C_6$alkyl, —O—$C_3$-$C_{10}$cycloalkyl, —$CF_3$, —CN, —$OCF_2H$, —$OCH_2F$, —$OCF_3$, halogen, —$CONR_7R_{10}$, —$NR_7R_{10}$, —$NR_7COR_8$, —$NR_7SO_2R_9$, or —$SO_2R_9$;

$R_2$ and $R_6$ are independently hydrogen, F, Br, I, —$CF_3$, —$OCF_3$, —$OCHF_2$, —$OCH_2F$, $C_2$-$C_6$alkyl, $C_3$-$C_{10}$cycloalkyl, $C_3$-$C_{10}$heterocyclyl, —$OC_1$-$C_6$alkyl, —O—$C_3$-$C_{10}$cycloalkyl, —$NR_7COR_8$, —$NR_7SO_2R_9$, —$CONR_7R_{10}$, —$SO_2NR_7R_{10}$, —CN, aryl, heteroaryl, —$NR_7R_{10}$, or —$SO_2R_9$;

$R_3$ and $R_5$ are independently hydrogen, halogen, —$CF_3$, —$OCF_3$, —$OCHF_2$, —$OCH_2F$, $C_1$-$C_6$alkyl, $C_3$-$C_{10}$cycloalkyl, $C_3$-$C_{10}$heterocyclyl, —$OC_1$-$C_6$alkyl, —O—$C_3$-$C_{10}$cycloalkyl, —$CONR_7R_{10}$, —$NR_7COR_8$, —$NR_7SO_2R_9$, —$SO_2NR_7R_{10}$, —CN, aryl, heteroaryl, —$NR_7R_{10}$, or —$SO_2R_9$;

$R_4$ is hydrogen, F, Cl, Br, I, —$CF_3$, —CN, —$OCHF_2$, —$OCH_2F$, —$OCF_3$, $C_1$-$C_6$alkyl, $C_3$-$C_{10}$cycloalkyl, $C_3$-$C_{10}$heterocyclyl, —$OC_1$-$C_6$alkyl, —$OC_3$-$C_{10}$cycloalkyl, —$NR_7SO_2R_9$, —$NR_7COR_8$, —$CONR_7R_{10}$, —$SO_2NR_7R_{10}$, aryl, heteroaryl, —$NR_7R_{10}$, or —$SO_2R_9$; or any two adjacent variables selected from $R_2$, $R_3$, $R_4$, $R_5$, and $R_6$ can be taken together to form a cycloalkyl, aryl, heteroaryl or heterocyclyl, each of which is optionally substituted by one, two, or three substituents independently selected from the group consisting of alkoxy, alkyl, alkenyl, alkynyl, amido, amino, aryl, cyano, cycloalkyl, haloalkyl, halogen, heteroaryl, heterocyclyl, hydroxyl, nitro and sulfonyl;

$R_7$ and $R_{10}$ are independently hydrogen; or alkyl or cycloalkyl, each of which are optionally substituted with one or two substituents independently selected from the group consisting of halogen, cyano, hydroxy, nitro, and alkoxy, or $R_7$ and $R_{10}$ can be taken together to form a heterocyclyl optionally substituted by one, two, or three substituents independently selected from the group consisting of alkoxy, alkyl, alkenyl, alkynyl, amido, amino, aryl, cyano, cycloalkyl, haloalkyl, halogen, heteroaryl, heterocyclyl, hydroxyl, nitro and sulfonyl; wherein the heterocyclyl is not imidazolyl;

$R_8$ is alkoxy, alkyl, alkenyl, alkynyl, amido, amino, aryl, cycloalkoxy, cycloalkyl, haloalkyl, heteroaryl, or heterocyclyl;

$R_9$ is alkyl, alkenyl, alkynyl, amido, amino, aryl, cycloalkoxy, cycloalkyl, haloalkyl, heteroaryl, or heterocyclyl;

where at least one of $R_2$, $R_3$, $R_4$, $R_5$, and $R_6$ is not hydrogen;

where $R_3$ is not morpholino or pyridyl; and where if $R_4$ is —$CH_3$, —$OCF_3$, —$OCH_3$, F, Cl, —CONHnBu, —CONH-cyclopentyl, or —CONH—$CH_2$-phenyl-3-Me, then W is not unsubstituted cyclohexyl or $R_1$ is not hydrogen.

In certain embodiments, at least one of $R_1$ and $R_{11}$ is selected from the group consisting of hydrogen, $C_1$-$C_6$alkyl, —O—$C_1$-$C_6$alkyl, —O—$C_3$-$C_{10}$cycloalkyl, —$OCHF_2$, —$OCH_2F$, —$OCF_3$, —CN, and —$NR_7R_{10}$. In certain embodiments, at least one of $R_1$ and $R_{11}$ is selected from the group consisting of hydrogen, —$CH_3$, —$OCH_3$, —O—$CH_2$cyclopropyl, —O-isopropyl, —O-t-butyl, —O-cyclobutyl, and —$N(CH_3)_2$. In certain embodiments, at least one of $R_2$ and $R_6$ is selected from the group consisting of hydrogen, —$NR_7R_{10}$, F, —$OCH_3$, —$OCF_2H$, and —$OCF_3$.

In certain embodiments, at least one of $R_3$ and $R_5$ is selected from the group consisting of hydrogen, F, —$OCF_2H$, —$OCFH_2$, —$OCF_3$, —OtBu and —OiPr. In certain embodiments, $R_4$ is selected from the group consisting of hydrogen, —$OCH_3$, —$OCF_3$, —OiPr, —$OCF_2H$, —O—$C_3$-$C_{10}$cycloalkyl, —$SO_2R_9$, —$SO_2NR_7R_{10}$, —$CONR_7R_{10}$, and $C_3$-$C_{10}$heterocyclyl. In certain embodiments, $R_3$ and $R_4$ are taken together to form a heterocyclyl selected from the group consisting of benzodioxolyl, difluorobenzodioxolyl, dihydrobenzodioxinyl, and dihydrobenzofuranyl. In certain embodiments, one of $X_2$-$X_6$ is N. In certain embodiments, $X_4$ is N. In certain embodiments, W is selected from the group consisting of cyclobutyl, cycloheptyl, cyclohexyl, 4-methylcyclohexyl, 4-ethylcyclohexyl, 4-trifluoromethylcyclohexyl, 1-methylcyclohexyl, cyclopentyl, isopropyl, and bicyclo[2,2,1]heptyl. In certain embodiments, W is selected from the group consisting of cyclobutyl, cyclohexyl, cycloheptyl, 4-methylcyclohexyl, 4-ethylcyclohexyl, 4-trifluoromethylcyclohexyl, cyclopentyl, and —$CH_2$cyclohexyl.

Another aspect of the invention provides a compound of formula Ib:

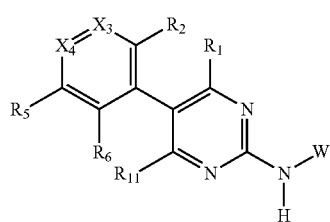

including a pharmaceutically acceptable salt thereof, wherein:

$X_3$ is $CR_3$ or N;

$X_4$ is $CR_4$ or N;

W is cyclohexyl optionally substituted with one or two substituents independently selected from the group consisting of methyl, ethyl, propyl, methoxy, ethoxy, trifluoromethyl, and halogen;

$R_1$ is hydrogen, methyl, ethyl, cyclopropyl, cyclobutyl, cyclopentyl, cyclohexyl, —$OC_1$-$C_6$alkyl, —O—$C_3$-$C_{10}$cycloalkyl, —O—$C_3$-$C_{10}$heterocycloalkyl, or —O—$(CH_2)_n$—$C_3$-$C_{10}$heterocycloalkyl;

$R_2$, $R_5$, and $R_6$ are independently hydrogen, methyl, or ethyl;

$R_3$ is hydrogen, halogen, —$CF_3$, —$OCF_3$, —$OCHF_2$, —$OCH_2F$, methyl, ethyl, methoxy, or ethoxy;

$R_4$ is hydrogen, F, Cl, Br, I, —$CF_3$, —CN, —$OCHF_2$, —$OCH_2F$, —$OCF_3$, $C_1$-$C_6$alkyl, $C_3$-$C_{10}$cycloalkyl, $C_3$-$C_{10}$heterocyclyl, —$OC_1$-$C_6$alkyl, —$OC_3$-$C_{10}$cycloalkyl, —$OC_3$-$C_{10}$heterocycloalkyl, —$SC_1$-$C_6$alkyl, —$SC_3$-$C_{10}$cycloalkyl, —$NR_7SO_2R_9$, —$NR_7COR_8$, —$CONR_7R_{10}$, —$SO_2NR_7R_{10}$, aryl, heteroaryl, —$NR_7R_{10}$, or —$SO_2R_9$; or $R_7$ and $R_{10}$ are independently hydrogen; or $C_1$-$C_6$alkyl, $C_3$-$C_{10}$cycloalkyl, or $C_3$-$C_{10}$heterocycloalkyl, each of which are optionally substituted with one or two substituents independently selected from the group consisting of halogen, methyl, ethyl, methoxy, or ethoxy;

$R_8$ and $R_9$ are independently is methyl, ethyl, propyl, butyl, pentyl, hexyl, phenyl, or benzyl, each of which is optionally substituted by halogen or methoxy;

$R_{11}$ is hydrogen or methyl;

n is 1, 2, or 3; and where if $R_4$ is —$CH_3$, —$OCF_3$, —$OCH_3$, F, Cl, —CONHnBu, —CONH-cyclopentyl, or —CONH—$CH_2$-phenyl-3-Me, then W is not unsubstituted cyclohexyl or $R_1$ is not hydrogen.

In certain embodiments, $X_3$ is $CR_3$. In certain embodiments, $X_3$ is N. In certain embodiments, $X_4$ is $CR_4$. In certain embodiments, $X_4$ is N. In certain embodiments, W is cyclohexyl optionally substituted with one or two substituents independently selected from the group consisting of methyl and ethyl. In certain embodiments, $R_1$ is methyl, ethyl, cyclopropyl, cyclobutyl, cyclopentyl, cyclohexyl, —$OC_1$-$C_6$alkyl, —O—$C_3$-$C_{10}$cycloalkyl, —O—$C_3$-$C_{10}$heterocycloalkyl, or —O—$(CH_2)_n$—$C_3$-$C_{10}$heterocycloalkyl. In certain embodiments, $R_1$ is methyl, ethyl, cyclopropyl, cyclobutyl, cyclopentyl, or cyclohexyl. In certain embodiments, $R_1$ is —$OC_1$-$C_6$ alkyl, —O—$C_3$-$C_{10}$ cycloalkyl, —O—$C_3$-$C_{10}$heterocycloalkyl, or —O—$(CH_2)_n$—$C_3$-$C_{10}$heterocycloalkyl. In certain embodiments, $R_1$ is —O—$(CH_2)_n$—$C_3$-$C_{10}$heterocycloalkyl. In certain embodiments, $R_1$ is —O—$(CH_2)_n$-tetrahydrofuranyl, —O—$(CH_2)_n$-tetrahydropyranyl, or —O—$(CH_2)_n$-pyrrolidinyl, each of which is optionally substituted by methyl or ethyl. In certain embodiments, $R_3$ is hydrogen, halogen, —$CF_3$, —$OCF_3$, —$OCHF_2$, —$OCH_2F$, methyl, ethyl, methoxy, or ethoxy. In certain embodiments, $R_4$ is hydrogen, F, Cl, Br, I, —$CF_3$, —CN, —$OCHF_2$, —$OCH_2F$, —$OCF_3$, $C_1$-$C_6$alkyl, $C_3$-$C_{10}$cycloalkyl, $C_3$-$C_{10}$heterocyclyl, —$OC_1$-$C_6$alkyl, —$OC_3$-$C_{10}$cycloalkyl, or —$OC_3$-$C_{10}$heterocycloalkyl. In certain embodiments, $R_4$ is hydrogen, F, Cl, Br, I, —$CF_3$, —CN, —$OCHF_2$, —$OCH_2F$, —$OCF_3$, methyl, ethyl, methoxy, or ethoxy, cyclopropyl, cyclobutyl, cyclopentyl, cyclohexyl, tetrahydrofuranyl, tetrahydropyranyl, pyrrolidinyl, or piperidinyl. In certain embodiments, $R_4$ is —$OCHF_2$, —$OCH_2F$, —$OCF_3$, methyl, ethyl, methoxy, or ethoxy, cyclopropyl, cyclobutyl, cyclopentyl, cyclohexyl, tetrahydrofuranyl, tetrahydropyranyl, pyrrolidinyl, or piperidinyl. In certain embodiments, $R_4$ is morpholinyl. In certain embodiments, $R_4$ is —$OCHF_{25}$—$OCH_2F$, or —$OCF_3$. In certain embodiments, $R_7$ and $R_{10}$ are independently hydrogen, methyl, ethyl, propyl, butyl, cyclopropyl, cyclobutyl, cyclopentyl, or cyclohexyl.

Another aspect of the invention provides a compound of formula II:

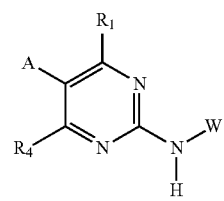

including a pharmaceutically acceptable salt, prodrug or N-oxide thereof, wherein:

A is one of the following:

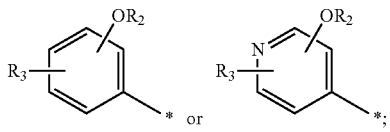

W is $C_1$-$C_{10}$alkyl or $C_4$-$C_{10}$cycloalkyl, each of which is optionally substituted with one or two substituents independently selected from the group consisting of $C_1$-$C_6$alkyl, $C_3$-$C_{10}$cycloalkyl, —$OC_1$-$C_6$alkyl, —O—$C_3$-$C_{10}$cycloalkyl, —$CF_3$, —OH, and fluoro;

$R_1$ and $R_4$ are independently hydrogen, $C_1$-$C_6$alkyl, $C_3$-$C_{10}$cycloalkyl, —$OC_1$-$C_6$alkyl, —O—$C_3$-$C_{10}$cycloalkyl, —O—$C_3$-$C_{10}$heterocycloalkyl, —O—C($R_8$)($R_9$)—$C_3$-$C_{10}$heterocycloalkyl, —$CF_3$, —CN, —$OCF_2H$, —$OCH_2F$, —$OCF_3$, halogen, —$CONR_5R_6$, —$NR_5R_6$, —$NR_5COR_6$, —$NR_5SO_2R_7$, or —$SO_2R_7$;

$R_2$ is $C_1$-$C_6$alkyl;

$R_3$ is halogen, —$CF_3$, —$OCF_3$, —$OCHF_2$, —$OCH_2F$, $C_1$-$C_6$alkyl, $C_3$-$C_{10}$cycloalkyl, $C_3$-$C_{10}$heterocyclyl, —$OC_1$-$C_6$alkyl, —O—$C_3$-$C_{10}$cycloalkyl, —O—$C_3$-$C_{10}$heterocycloalkyl, —$CONR_5R_6$, —$NR_5COR_7$, —$NR_7SO_2R_7$, —$SO_2NR_5R_6$, —CN, aryl, heteroaryl, —$NR_5R_6$, or —$SO_2R_7$;

$R_5$ and $R_6$ are each independently hydrogen; or alkyl or cycloalkyl, each of which is optionally substituted with one or two substituents independently selected from the group consisting of halogen, cyano, hydroxy, and alkoxy; or $R_5$ and $R_6$ are taken together to form a heterocyclyl that is optionally substituted by one, two, or three substituents independently selected from the group consisting of alkoxy, alkyl, alkenyl, alkynyl, amido, amino, aryl, cyano, cycloalkyl, haloalkyl, halogen, heteroaryl, heterocyclyl, hydroxyl, and sulfonyl;

$R_7$ represents independently for each occurrence alkyl, alkenyl, alkynyl, aryl, cycloalkoxy, cycloalkyl, haloalkyl, heteroaryl, or heterocyclyl; and $R_8$ and $R_9$ represent independently hydrogen, methyl, ethyl, n-propyl, isopropyl, or cyclopropyl; or $R_8$ and $R_9$ taken together with the atom to which they are attached form a $C_3$-$C_6$cycloalkyl group.

In certain embodiments, A is

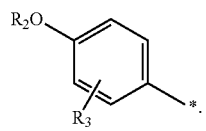

In certain embodiments, A is

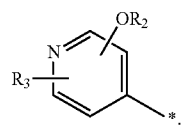

In certain embodiments, $R_1$ and $R_4$ are independently hydrogen, $C_1$-$C_6$alkyl, —$OC_1$-$C_6$alkyl, —O—$C_3$-$C_{10}$cycloalkyl, —O—$C_3$-$C_{10}$heterocycloalkyl, or —O—$CH_2$—$C_3$-$C_{10}$heterocycloalkyl. In certain embodiments, $R_1$ is methoxy, ethoxy, or propoxy; and $R_4$ is hydrogen, methoxy, —O-tetrahydrofuranyl, —O-tetrahydropyranyl, —O—$CH_2$-tetrahydrofuranyl, —O—$CH_2$-tetrahydropyranyl, —O-pyrrolidinyl, —O-piperidinyl, or —O-azetidinyl. In certain embodiments, $R_1$ and $R_4$ are independently hydrogen, $C_1$-$C_6$alkyl, —$OC_1$-$C_6$alkyl, —O—$C_3$-$C_{10}$cycloalkyl, or —O—$C_3$-$C_{10}$heterocycloalkyl. In certain embodiments, $R_1$ is methoxy, ethoxy, or propoxy; and $R_4$ is hydrogen. In certain embodiments, $R_3$ is halogen, —$CF_3$, —$OCF_3$, —$OCHF_2$, —$OCH_2F$, $C_1$-$C_6$alkyl, —$OC_1$-$C_6$alkyl, or $C_3$-$C_8$cycloalkyl. In certain embodiments, $R_3$ is halogen, —$CF_3$, —$OCF_3$, —$OCHF_2$, —$OCH_2F$, $C_1$-$C_6$alkyl, or —$OC_1$-$C_6$alkyl. In certain embodiments, W is $C_4$-$C_{10}$cycloalkyl optionally substituted with one or two $C_1$-$C_6$alkyl substituents. In certain embodiments, W is cyclohexyl substituted with $C_1$-$C_6$alkyl.

Another aspect of the invention provides a compound of formula III:

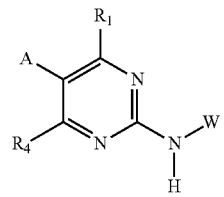

including a pharmaceutically acceptable salt, prodrug or N-oxide thereof, wherein:

A is

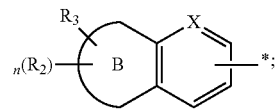

B is heteroaryl or an unsaturated heterocyclyl;

X is C(H) or N;

W is $C_1$-$C_{10}$alkyl or $C_4$-$C_{10}$cycloalkyl, each of which is optionally substituted with one or two substituents independently selected from the group consisting of $C_1$-$C_6$alkyl, $C_3$-$C_{10}$cycloalkyl, —$OC_1$-$C_6$alkyl, —O—$C_3$-$C_{10}$cycloalkyl, —$CF_3$, —OH, and fluoro;

$R_1$ and $R_4$ are independently hydrogen, $C_1$-$C_6$alkyl, $C_3$-$C_{10}$cycloalkyl, —$OC_1$-$C_6$alkyl, —O—$C_3$-$C_{10}$cycloalkyl, —O—$C_3$-$C_{10}$heterocycloalkyl, —O—$(CR_8R_9)_m$—$C_3$-$C_{10}$heterocycloalkyl, —O-aryl, —$CF_3$, —CN, —$OCF_2H$, —$OCH_2F$, —$OCF_3$, halogen, —$CONR_5R_6$, —$NR_5R_6$, —$NR_5COR_6$, —$NR_5SO_2R_7$, or —$SO_2R_7$;

$R_2$ represents independently for each occurrence halogen, —$CF_3$, —$OCF_3$, —$OCHF_2$, —$OCH_2F$, —CN, $C_1$-$C_6$alkyl, $C_3$-$C_{10}$cycloalkyl, $C_3$-$C_{10}$heterocyclyl, —$OC_1$-$C_6$alkyl, —O—$C_3$-$C_{10}$cycloalkyl, —O—$C_3$-$C_{10}$heterocyclyl, —$CONR_5$, $R_6$, —$NR_5COR_7$, —$NR_7SO_2R_7$, —$SO_2NR_5R_6$, —CN, aryl, heteroaryl, —$NR_5R_6$, or —$SO_2R_7$;

$R_3$ is hydrogen, $C_1$-$C_6$alkyl, or $C_3$-$C_6$cycloalkyl;

$R_5$ and $R_6$ are independently hydrogen; or alkyl or cycloalkyl, each of which is optionally substituted with one or two substituents independently selected from the group consisting of halogen, cyano, hydroxy, nitro, and alkoxy; or $R_5$ and $R_6$ are taken together to form a heterocyclyl that is optionally substituted by one, two, or three substituents independently selected from the group consisting of alkoxy, alkyl, alkenyl, alkynyl, amido, amino, aryl, cyano, cycloalkyl, haloalkyl, halogen, heteroaryl, heterocyclyl, hydroxyl, nitro and sulfonyl;

$R_7$ represents independently for each occurrence alkyl, alkenyl, alkynyl, amido, amino, aryl, cycloalkoxy, cycloalkyl, haloalkyl, heteroaryl, or heterocyclyl;

$R_8$ and $R_9$ each represent independently for each occurrence H, methyl, ethyl, or n-propyl, or isopropyl; or $R_8$ and $R_9$ taken together with the atom to which they are attached form a $C_3$-$C_6$-cycloalkyl group;

m is 1, 2, or 3; and n is 0, 1, or 2.

In certain embodiments, A is

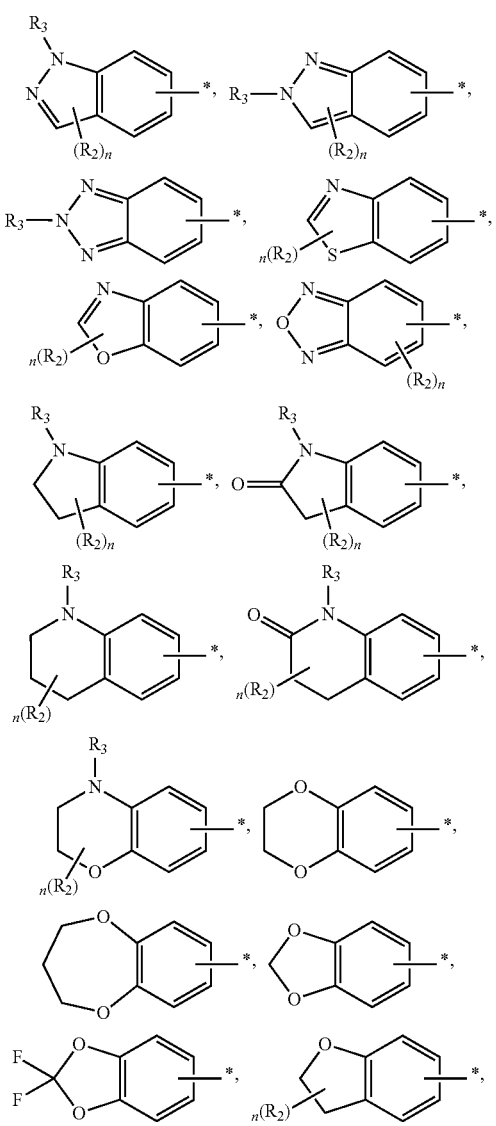

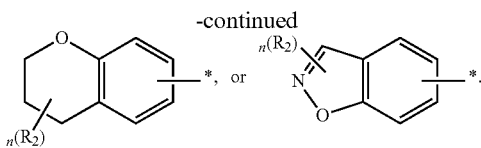

In certain embodiments, A is

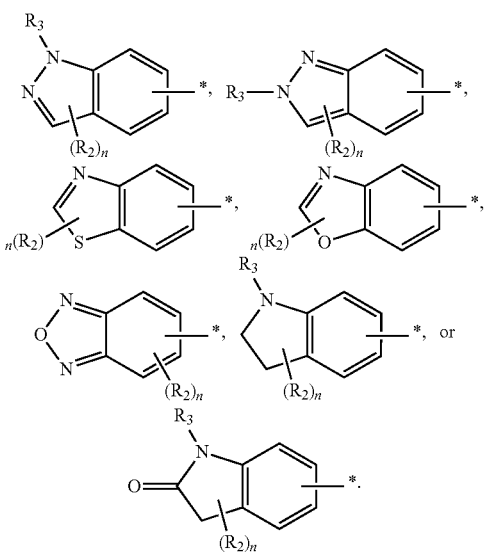

In certain embodiments, A is

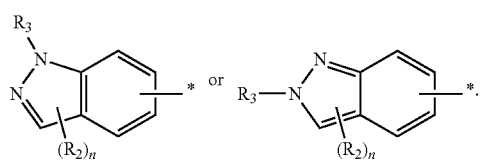

In certain embodiments, $R_1$ and $R_4$ are independently hydrogen, —$OC_1$-$C_6$alkyl, —O—$C_3$-$C_{10}$cycloalkyl, —O—$C_3$-$C_{10}$heterocycloalkyl, or —O—$CH_2$—$C_3$-$C_{10}$heterocycloalkyl. In certain embodiments, $R_1$ is methoxy, t-butoxy, cyclobutoxy, cyclopropylmethoxy, —O-tetrahydrofuranyl, —O-tetrahydropyranyl, —O—$CH_2$-tetrahydrofuranyl, —O—$CH_2$-tetrahydropyranyl, —O-pyrrolidinyl-$CO_2CH_3$, —O-pyrrolidinyl-$SO_2CH_3$, or —O-phenyl-$OCH_3$. In certain embodiments, $R_1$ and $R_4$ are independently hydrogen, —$OC_1$-$C_6$alkyl, —O—$C_3$-$C_{10}$cycloalkyl, or —O—$C_3$-$C_{10}$heterocycloalkyl. In certain embodiments, $R_1$ is methoxy, ethoxy, propoxy, —O-tetrahydrofuranyl, —O-pyrrolidinyl, or —O-phenyl-$OCH_3$. In certain embodiments, $R_2$ represents independently for each occurrence halogen, —$CF_3$, —$OCF_3$, —$OCHF_2$, —$OCH_2F$, $C_1$-$C_6$alkyl, $C_3$-$C_6$cycloalkyl, or —$OC_1$-$C_6$alkyl. In certain embodiments, $R_2$ represents independently for each occurrence halogen, —$CF_3$, —$OCF_3$, —$OCHF_2$, —$OCH_2F$, $C_1$-$C_6$alkyl, or —$OC_1$-$C_6$alkyl. In certain embodiments, n is 0. In certain embodiments, $R_3$ is hydrogen, methyl, ethyl, n-propyl, isopropyl, cyclopropyl, cyclobutyl, or methoxymethyl. In certain embodiments, $R_3$ is hydrogen, methyl, ethyl, or propyl. In certain embodiments, $R_4$ is hydrogen or methyl. In certain embodiments, W is $C_4$-$C_{10}$cycloalkyl optionally substituted with one or two $C_1$-$C_6$alkyl substituents. In certain embodiments, W is cyclohexyl substituted with $C_1$-$C_6$alkyl.

In certain embodiments, the compound is selected from the group consisting of: N-((1S,4S)-4-methylcyclohexyl)-5-(4-(trifluoromethoxy)phenyl)pyrimidin-2-amine; N-((1R,4R)-4-methylcyclohexyl)-5-(4-(trifluoromethoxy)phenyl)pyrimidin-2-amine; 5-(4-isopropoxyphenyl)-N-((1S,4S)-4-(trifluoromethyl)cyclohexyl)pyrimidin-2-amine; 5-(4-isopropoxyphenyl)-4-methoxy-N-((1S,4S)-4-methylcyclohexyl)pyrimidin-2-amine; N-cyclohexyl-5-(3-(trifluoromethoxy)phenyl)pyrimidin-2-amine; N-cyclohexyl-5-(2-(trifluoromethoxy)phenyl)pyrimidin-2-amine; N-(4-(2-(cyclohexylamino)pyrimidin-5-yl)phenyl) isobutyramide; N-cyclohexyl-5-(2-fluorophenyl)pyrimidin-2-amine; N-cyclohexyl-5-(3-fluorophenyl)pyrimidin-2-amine; N-cyclopentyl-5-(4-(trifluoromethoxy)phenyl)pyrimidin-2-amine; N-(4-(2-(cyclohexylamino)pyrimidin-5-yl)phenyl) isobutyramide; N-cyclohexyl-5-(2-fluorophenyl)pyrimidin-2-amine; N-cyclohexyl-5-(3-fluorophenyl)pyrimidin-2-amine; N-cyclopentyl-5-(4-(trifluoromethoxy)phenyl)pyrimidin-2-amine; N-cyclohexyl-5-(4-isopropoxyphenyl)pyrimidin-2-amine; N-cyclohexyl-5-(4-(pyrrolidin-1-ylsulfonyl)phenyl)pyrimidin-2-amine; (4-(2-(cyclohexylamino)pyrimidin-5-yl)phenyl)(pyrrolidin-1-yl)methanone; 4-(2-(cyclohexylamino)pyrimidin-5-yl)benzonitrile; N-cyclohexyl-5-(4-morpholinophenyl)pyrimidin-2-amine; 5-(4-(difluoromethoxy)phenyl)-N-((1s,4s)-4-methylcyclohexyl)pyrimidin-2-amine; N-cyclohexyl-5-(6-methylpyridin-3-yl)pyrimidin-2-amine; 5-(benzo[d][1,3]dioxol-5-yl)-N-cyclohexylpyrimidin-2-amine; N-cyclohexyl-5-(2,3-dihydrobenzo[b][1,4]dioxin-6-yl)pyrimidin-2-amine; 5-(4-isopropoxyphenyl)-N-((1s,4s)-4-methylcyclohexyl)pyrimidin-2-amine; 5-(6-methoxypyridin-3-yl)-N-((1s,4s)-4-methylcyclohexyl)pyrimidin-2-amine; 5-(2-methoxypyridin-4-yl)-N-((1s,4s)-4-methylcyclohexyl)pyrimidin-2-amine; 5-(2,2-difluorobenzo[d][1,3]dioxol-5-yl)-N-((1s,4s)-4-methylcyclohexyl)pyrimidin-2-amine; 5-(4-methoxyphenyl)-N-((1s,4s)-4-methylcyclohexyl)pyrimidin-2-amine; 5-(2,3-dihydrobenzofuran-5-yl)-N-((1s,4s)-4-methylcyclohexyl)pyrimidin-2-amine; N-((1s,4s)-4-methylcyclohexyl)-5-(4-(methylsulfonyl)phenyl)pyrimidin-2-amine; N-cyclohexyl-4-methoxy-5-(4-(trifluoromethoxy)phenyl)pyrimidin-2-amine; N-cycloheptyl-5-(4-(trifluoromethoxy)phenyl)pyrimidin-2-amine; N-(tetrahydro-2H-pyran-4-yl)-5-(4-(trifluoromethoxy)phenyl)pyrimidin-2-amine; N-cyclobutyl-5-(4-(trifluoromethoxy)phenyl)pyrimidin-2-amine; 5-(2,2-difluorobenzo[d][1,3]dioxol-4-yl)-N-((1s,4s)-4-methylcyclohexyl)pyrimidin-2-amine; 5-(3-isopropoxyphenyl)-N-((1s,4s)-4-methylcyclohexyl)pyrimidin-2-amine; N-cyclohexyl-5-(4-isopropoxyphenyl)-4-methoxypyrimidin-2-amine; 5-(3-(difluoromethoxy)phenyl)-N-((1s,4s)-4-methylcyclohexyl)pyrimidin-2-amine; 5-(2-(difluoromethoxy)phenyl)-N-((1s,4s)-4-methylcyclohexyl)pyrimidin-2-amine; N-((1s,4s)-4-methylcyclohexyl)-5-(4-(pyrrolidin-1-yl)phenyl)pyrimidin-2-amine; N-cycloheptyl-5-(4-(difluoromethoxy)phenyl)pyrimidin-2-amine; N-((1s,4s)-4-methylcyclohexyl)-5-(4-(trifluoromethyl)phenyl)pyrimidin-2-amine; N-((1s,4s)-4-methylcyclohexyl)-5-(4-morpholinophenyl)pyrimidin-2-amine; 5-(4-(difluoromethoxy)phenyl)-N-((1s,4s)-4-ethylcyclohexyl)pyrimidin-2-amine; N-((1s,4s)-4-ethylcyclohexyl)-5-(4-isopropoxyphenyl)pyrimidin-2-amine; 5-(4-cyclobutoxyphenyl)-N-((1s,4s)-4-methylcyclohexyl)pyrimidin-2-amine; N-cyclopentyl-5-(4-(difluoromethoxy)phenyl)pyrimidin-2-amine; N-(cyclohexylmethyl)-5-(4-(difluoromethoxy)phenyl)pyrimidin-2-amine; 5-(4-(difluoromethoxy)phenyl)-N-(tetrahydro-2H-pyran-3-yl)pyrimidin-2-amine; N-((1s,4s)-4-methylcyclohexyl)-5-(2,4,6-trimethoxyphenyl)pyrimidin-2-amine; N-((1s,4s)-4-methylcyclohexyl)-5-(6-(piperidin-1-yl)pyridin-3-yl)pyrimidin-2-amine; N-cyclopentyl-5-(4-isopropoxyphenyl)pyrimidin-2-amine; N-(4,4-difluorocyclohexyl)-5-(4-(difluoromethoxy)phenyl)pyrimidin-2-amine; 5-(4-(cyclopropylmethoxy)phenyl)-N-41s,4s)-4-methylcyclohexyl)pyrimidin-2-amine; N-((1s,4s)-4-methylcyclohexyl)-5-(4-(2,2,2-trifluoroethoxy)phenyl)pyrimidin-2-amine; 5-(3-fluoro-4-(2,2,2-trifluoroethoxy)phenyl)-N-((1s,4s)-4-methylcyclohexyl)pyrimidin-2-amine; 5-(4-fluoro-3-(2,2,2-trifluoroethoxy)phenyl)-N-((1s,4s)-4-methylcyclohexyl)pyrimidin-2-amine; 5-(5-chloropyridin-3-yl)-N-((1s,4s)-4-methylcyclohexyl)pyrimidin-2-amine; 4-methoxy-N-((1s,4s)-4-methylcyclohexyl)-5-(4-(trifluoromethoxy)phenyl)pyrimidin-2-amine; 5-(4-(difluoromethoxy)phenyl)-4-methoxy-N-((1s,4s)-4-methylcyclohexyl)pyrimidin-2-amine; 5-(4-tert-butoxyphenyl)-N-((1s,4s)-4-methylcyclohexyl)pyrimidin-2-amine; 5-(4-(5-methyl-1,3,4-oxadiazol-2-yl)phenyl)-N-((1s,4s)-4-methylcyclohexyl)pyrimidin-2-amine; N-cyclohexyl-5-(4-(difluoromethoxy)phenyl)-4-methoxypyrimidin-2-amine; N-(bicyclo[2.2.1]heptan-2-yl)-5-(4-(trifluoromethoxy)phenyl)pyrimidin-2-amine; 5-(4-(difluoromethoxy)phenyl)-N-((1s,4s)-4-(trifluoromethyl)cyclohexyl)pyrimidin-2-amine; 4-methoxy-5-(2-methyl-4-(trifluoromethoxy)phenyl)-N-((1s,4s)-4-methylcyclohexyl)pyrimidin-2-amine; 4-methoxy-5-(2-methoxy-4-(trifluoromethoxy)phenyl)-N-((1s,4s)-4-methylcyclohexyl)pyrimidin-2-amine; 5-(5-chloro-2-methoxypyridin-4-yl)-N-((1s,4s)-4-methylcyclohexyl)pyrimidin-2-amine; N-((1s,4s)-4-methylcyclohexyl)-5-(2-methylpyridin-4-yl)pyrimidin-2-amine; 4-methoxy-N-((1s,4s)-4-methylcyclohexyl)-5-(4-(piperidin-1-yl)phenyl)pyrimidin-2-amine; N-cyclohexyl-5-(4-(trifluoromethoxy)phenoxy)pyrimidin-2-amine; 5-(2-methoxy-4-(trifluoromethoxy)phenyl)-N-((1s,4s)-4-methylcyclohexyl)pyrimidin-2-amine; 5-(4-(difluoromethoxy)phenyl)-N-(1-methylcyclohexyl)pyrimidin-2-amine; 5-(6-isopropoxypyridin-3-yl)-4-methoxy-N-((1s,4s)-4-methylcyclohexyl)pyrimidin-2-amine; 4-methoxy-N-((1s,4s)-4-methylcyclohexyl)-5-(6-(piperidin-1-yl)pyridin-3-yl)pyrimidin-2-amine; N-cyclohexyl-5-(2-methoxy-4-(trifluoromethoxy)phenyl)pyrimidin-2-amine; N2-cyclohexyl-5-(4-(trifluoromethoxy)phenyl)pyrimidine-2,4-diamine; 4-methoxy-N-((1s,4s)-4-methylcyclohexyl)-5-(2-(trifluoromethyl)pyridin-4-yl)pyrimidin-2-amine; 5-(4-(difluoromethoxy)phenyl)-N-((1s,4s)-4-ethylcyclohexyl)pyrimidin-2-amine; N-((1s,4s)-4-ethylcyclohexyl)-5-(4-isopropoxyphenyl)pyrimidin-2-amine; 5-(4-cyclobutoxyphenyl)-N-((1s,4s)-4-methylcyclohexyl)pyrimidin-2-amine; N-cyclopentyl-5-(4-(difluoromethoxy)phenyl)pyrimidin-2-amine; N-(cyclohexylmethyl)-5-(4-(difluoromethoxy)phenyl)pyrimidin-2-amine; N-((1s,4s)-4-methylcyclohexyl)-5-(2,4,6-trimethoxyphenyl)pyrimidin-2-amine; N-((1s,4s)-4-methylcyclohexyl)-5-(6-(piperidin-1-yl)pyridin-3-yl)pyrimidin-2-amine; N-cyclopentyl-5-(4-isopropoxyphenyl)pyrimidin-2-amine; N-(4,4-difluorocyclohexyl)-5-(4-(difluoromethoxy)phenyl)pyrimidin-2-amine; 5-(4-(cyclopropylmethoxy)phenyl)-N-((1s,4s)-4-methylcyclohexyl)pyrimidin-2-amine; N-((1s,4s)-4-methylcyclohexyl)-5-(4-(2,2,2-trifluoroethoxy)phenyl)pyrimidin-2-amine; 5-(3-fluoro-4-(2,2,2-trifluoroethoxy)phenyl)-N-((1s,4s)-4-methylcyclohexyl)pyrimidin-2-amine; 5-(4-fluoro-3-(2,2,2-trifluoroethoxy)phenyl)-N-((1s,4s)-4-methylcyclohexyl)pyrimidin-2-amine; 5-(5-chloropyridin-3-yl)-N-((1s,4s)-4-methylcyclohexyl)

pyrimidin-2-amine; 5-(4-isopropoxyphenyl)-4-methoxy-N-((1s,4s)-4-methylcyclohexyl)pyrimidin-2-amine; 4-methoxy-N-((1s,4s)-4-methylcyclohexyl)-5-(4-(trifluoromethoxy)phenyl)pyrimidin-2-amine; 5-(4-(difluoromethoxy)phenyl)-4-methoxy-N-((1s,4s)-4-methylcyclohexyl)pyrimidin-2-amine; 5-(4-tert-butoxyphenyl)-N-((1s,4s)-4-methylcyclohexyl)pyrimidin-2-amine; 5-(4-(5-methyl-1,3,4-oxadiazol-2-yl)phenyl)-N-((1s,4s)-4-methylcyclohexyl)pyrimidin-2-amine; N-cyclohexyl-5-(4-(difluoromethoxy)phenyl)-4-methoxypyrimidin-2-amine; N-(bicyclo[2.2.1]heptan-2-yl)-5-(4-(trifluoromethoxy)phenyl)pyrimidin-2-amine; 5-(4-isopropoxyphenyl)-N-((1s,4s)-4-(trifluoromethyl)cyclohexyl)pyrimidin-2-amine; 5-(4-(difluoromethoxy)phenyl)-N-((1s,4s)-4-(trifluoromethyl)cyclohexyl)pyrimidin-2-amine; 4-methoxy-5-(2-methyl-4-(trifluoromethoxy)phenyl)-N-((1s,4s)-4-methylcyclohexyl)pyrimidin-2-amine; 4-methoxy-5-(2-methoxy-4-(trifluoromethoxy)phenyl)-N-((1s,4s)-4-methylcyclohexyl)pyrimidin-2-amine; 5-(5-chloro-2-methoxypyridin-4-yl)-N-((1s,4s)-4-methylcyclohexyl)pyrimidin-2-amine; N-((1s,4s)-4-methylcyclohexyl)-5-(2-methylpyridin-4-yl)pyrimidin-2-amine; 4-methoxy-N-((1s,4s)-4-methylcyclohexyl)-5-(4-(piperidin-1-yl)phenyl)pyrimidin-2-amine; 5-(2-methoxy-4-(trifluoromethoxy)phenyl)-N-((1s,4s)-4-methylcyclohexyl)pyrimidin-2-amine; 5-(4-(difluoromethoxy)phenyl)-N-(1-methylcyclohexyl)pyrimidin-2-amine; 5-(6-isopropoxypyridin-3-yl)-4-methoxy-N-((1s,4s)-4-methylcyclohexyl)pyrimidin-2-amine; 4-methoxy-N-((1s,4s)-4-methylcyclohexyl)-5-(6-(piperidin-1-yl)pyridin-3-yl)pyrimidin-2-amine; N-cyclohexyl-5-(2-methoxy-4-(trifluoromethoxy)phenyl)pyrimidin-2-amine; 4-methoxy-N-((1s,4s)-4-methylcyclohexyl)-5-(2-(trifluoromethyl)pyridin-4-yl)pyrimidin-2-amine; 5-(5-chloro-2-methoxypyridin-4-yl)-4-methoxy-N-((1s,4s)-4-methylcyclohexyl)pyrimidin-2-amine; 5-(4-(difluoromethoxy)phenyl)-N4,N4-dimethyl-N2-((1s,4s)-4-methylcyclohexyl)pyrimidine-2,4-diamine; 4-(cyclopropylmethoxy)-5-(4-isopropoxyphenyl)-N-((1s,4s)-4-methylcyclohexyl)pyrimidin-2-amine; 2-(4-(4-methoxy-2-((1s,4s)-4-methylcyclohexylamino)pyrimidin-5-yl)phenoxy)acetonitrile; 4-tert-butoxy-5-(4-isopropoxyphenyl)-N-((1s,4s)-4-methylcyclohexyl)pyrimidin-2-amine; 4-(cyclopropylmethoxy)-5-(4-(difluoromethoxy)phenyl)-N-((1s,4s)-4-methylcyclohexyl)pyrimidin-2-amine; 4-cyclobutoxy-5-(4-(difluoromethoxy)phenyl)-N-((1s,4s)-4-methylcyclohexyl)pyrimidin-2-amine; 4-cyclobutoxy-5-(4-isopropoxyphenyl)-N-((1s,4s)-4-methylcyclohexyl)pyrimidin-2-amine; 4-methoxy-N-((1s,4s)-4-methylcyclohexyl)-5-(6-(methylthio)pyridin-3-yl)pyrimidin-2-amine; 2-(4-(4-cyclobutoxy-2-((1s,4s)-4-methylcyclohexylamino)pyrimidin-5-yl)phenoxy)acetonitrile; N-(2-admantanyl)-5-(4-isopropoxyphenyl)-4-methoxypyrimidin-2-amine; 2-(4-(4-(cyclopropylmethoxy)-2-((1s,4s)-4-methylcyclohexylamino)pyrimidin-5-yl)phenoxy)acetonitrile; 2-(4-(2-((1s,4s)-4-methylcyclohexylamino)-4-morpholinopyrimidin-5-yl)phenoxy)acetonitrile; 4-methoxy-N-((1s,4s)-4-methylcyclohexyl)-5-(6-(methylsulfonyl)pyridin-3-yl)pyrimidin-2-amine; 5-(4-(difluoromethoxy)phenyl)-N-((1s,4s)-4-methylcyclohexyl)-4-morpholinopyrimidin-2-amine; 5-(4-isopropoxyphenyl)-4,6-dimethyl-N-((1s,4s)-4-methylcyclohexyl)pyrimidin-2-amine; 4-methoxy-N-((1s,4s)-4-methylcyclohexyl)-5-(6-(pyrrolidin-1-yl)pyridin-3-yl)pyrimidin-2-amine; 546-(dimethylamino)pyridin-3-yl)-4-methoxy-N-((1s,4s)-4-methylcyclohexyl)pyrimidin-2-amine; 2-(4-(4,6-dimethyl-2-((1s,4s)-4-methylcyclohexylamino)pyrimidin-5-yl)phenoxy)acetonitrile; 4-(cyclopropylmethoxy)-N-((1s,4s)-4-methylcyclohexyl)-5-(6-(piperidin-1-yl)pyridin-3-yl)pyrimidin-2-amine; 4-methoxy-N-((1s,4s)-4-methylcyclohexyl)-5-(6-(2,2,2-trifluoroethoxy)pyridin-3-yl)pyrimidin-2-amine; 4-(4-methoxy-2-((1s,4s)-4-methylcyclohexylamino)pyrimidin-5-yl)picolinonitrile; 5-(4-(difluoromethoxy)phenyl)-N-((1s,4s)-4-methylcyclohexyl)-4-(pyrrolidin-1-yl)pyrimidin-2-amine; 5-(6-(cyclopropylmethoxy)pyridin-3-yl)-4-methoxy-N-((1s,4s)-4-methylcyclohexyl)pyrimidin-2-amine; 2-(4-(4-methoxy-2-(2-admantanylamino)pyrimidin-5-yl)phenoxy)acetonitrile; 5-(6-(dimethylamino)pyridin-3-yl)-4-methoxy-N-(2-admantanyl)pyrimidin-2-amine; 5-(6-(dimethylamino)pyridin-3-yl)-N-((1s,4s)-4-methylcyclohexyl)-4-(tetrahydro-2H-pyran-4-yloxy)pyrimidin-2-amine; 2-(4-(2-((1s,4s)-4-methylcyclohexylamino)-4-(tetrahydro-2H-pyran-4-yloxy)pyrimidin-5-yl)phenoxy)acetonitrile; 2-(4-(2-((1s,4s)-4-methylcyclohexylamino)-4-(tetrahydrofuran-3-yloxy)pyrimidin-5-yl)phenoxy)acetonitrile; 5-(6-(dimethylamino)pyridin-3-yl)-N-((1s,4s)-4-methylcyclohexyl)-4-(tetrahydrofuran-3-yloxy)pyrimidin-2-amine; 4-(cyclopropylmethoxy)-5-(6-methoxypyridin-3-yl)-N-((1s,4s)-4-methylcyclohexyl)pyrimidin-2-amine; 4-(cyclopropylmethoxy)-5-(6-(dimethylamino)pyridin-3-yl)-N-((1s,4s)-4-methylcyclohexyl)pyrimidin-2-amine; 4-(cyclopropylmethoxy)-5-(2-methoxypyridin-4-yl)-N-((1s,4s)-4-methylcyclohexyl)pyrimidin-2-amine; 4-methoxy-5-(3-(5-methyl-1,3,4-oxadiazol-2-yl)phenyl)-N-((1s,4s)-4-methylcyclohexyl)pyrimidin-2-amine; 5-(2-isopropoxypyridin-4-yl)-4-methoxy-N-((1s,4s)-4-methylcyclohexyl)pyrimidin-2-amine; 5-(2,6-dimethoxypyridin-3-yl)-4-methoxy-N-((1s,4s)-4-methylcyclohexyl)pyrimidin-2-amine; 5-(benzo[d]thiazol-5-yl)-4-methoxy-N-((1s,4s)-4-methylcyclohexyl)pyrimidin-2-amine; 2-(4-(4-methoxy-6-methyl-2-((1s,4s)-4-methylcyclohexylamino)pyrimidin-5-yl)phenoxy)acetonitrile; 2-(4-(2-((1s,4R)-4-methylcyclohexylamino)-4-((S)-tetrahydrofuran-3-yloxy)pyrimidin-5-yl)phenoxy)acetonitrile; 5-(6-isopropoxypyridin-3-yl)-N-((1s,4R)-4-methylcyclohexyl)-4-((S)-tetrahydrofuran-3-yloxy)pyrimidin-2-amine; 2-(4-(2-((1s,4S)-4-methylcyclohexylamino)-4-((R)-tetrahydrofuran-3-yloxy)pyrimidin-5-yl)phenoxy)acetonitrile; 5-(6-isopropoxypyridin-3-yl)-N-((1s,4S)-4-methylcyclohexyl)-4-((R)-tetrahydrofuran-3-yloxy)pyrimidin-2-amine; 5-(6-(dimethylamino)pyridin-3-yl)-N-((1s,4s)-4-methylcyclohexyl)-4-(tetrahydro-2H-pyran-3-yloxy)pyrimidin-2-amine; 5-(3-(5-methyl-1,3,4-oxadiazol-2-yl)phenyl)-N-((1s,4s)-4-methylcyclohexyl)-4-(tetrahydro-2H-pyran-3-yloxy)pyrimidin-2-amine; 4-methoxy-5-(4-methyl-3,4-dihydro-2H-pyrido[3,2-b][1,4]oxazin-7-yl)-N-((1s,4s)-4-methylcyclohexyl)pyrimidin-2-amine; 2-(4-(2-((1s,4s)-4-methylcyclohexylamino)-4-(tetrahydro-2H-pyran-3-yloxy)pyrimidin-5-yl)phenoxy)acetonitrile; 2-(4-(2-((1s,4s)-4-methylcyclohexylamino)-4-((tetrahydrofuran-3-yl)methoxy)pyrimidin-5-yl)phenoxy)acetonitrile; 5-(6-(dimethylamino)pyridin-3-yl)-N-((1s,4s)-4-methylcyclohexyl)-4-((tetrahydrofuran-3-yl)methoxy)pyrimidin-2-amine; 2-(4-(2-((1s,4s)-4-methylcyclohexylamino)-4-((tetrahydro-2H-pyran-4-yl)methoxy)pyrimidin-5-yl)phenoxy)acetonitrile; 5-(6-isopropoxypyridin-3-yl)-N-((1s,4s)-4-methylcyclohexyl)-4-((tetrahydro-2H-pyran-4-yl)methoxy)pyrimidin-2-amine; 4-methoxy-5-(1-methyl-1H-indazol-5-yl)-N-((1s,4s)-4-methylcyclohexyl)pyrimidin-2-amine; 2',4-dimethoxy-N-((1s,4s)-4-methylcyclohexyl)-5,5'-bipyrimidin-2-amine; 2',4,4'- trimethoxy-N-((1s,4s)-4-methylcyclohexyl)-5,5'-bipyrimidin-2-amine; 4-methoxy-5-(2-methyl-2H-indazol-6-yl)-N-((1s,4s)-4-methylcyclohexyl)pyrimidin-2-amine; 5-(4-isopropoxyphenyl)-N-((1s,4S)-4-methylcyclohexyl)-4-((R)-tetrahydrofuran-3-yloxy)pyrimidin-2-amine; 5-(4-(difluoromethoxy)phenyl)-N-((1s,4S)-4-methylcyclohexyl)-4-((R)-tetrahydrofuran-3-yloxy)pyrimidin-2-amine; 5-(4-isopropoxyphenyl)-N-((1s,4s)-4-methylcyclohexyl)-4-((tetrahydrofuran-3-yl)methoxy)pyrimidin-2-amine; 5-(4-(difluoromethoxy)phenyl)-N-((1s,4s)-4-methylcyclohexyl)-4-((tetrahydrofuran-3-yl)methoxy)pyrimidin-2-amine; 5-(benzo[d]thiazol-5-yl)-N-((1s,4S)-4-methylcyclohexyl)-4-((R)-tetrahydrofuran-3-yloxy)pyrimidin-2-amine; 5-(2,6-dimethoxypyridin-3-yl)-N-((1s,4S)-4-methylcyclohexyl)-4-((R)-tetrahydrofuran-3-yloxy)pyrimidin-2-amine; 2-(4-(4-(benzyloxy)-2-((1s,4s)-4-methylcyclohexylamino)pyrimidin-5-yl)phenoxy)acetonitrile; 5-(4-isopropoxyphenyl)-N-((1s,4R)-4-methylcyclohexyl)-4-((S)-tetrahydrofuran-3-yloxy)pyrimidin-2-amine; 5-(4-(difluoromethoxy)phenyl)-N-((1s,4R)-4-methylcyclohexyl)-4-((S)-tetrahydrofuran-3-yloxy)pyrimidin-2-amine; 5-(3-(5-methyl-1,3,4-oxadiazol-2-yl)phenyl)-N-((1s,4S)-4-methylcyclohexyl)-4-((R)-tetrahydrofuran-3-yloxy)pyrimidin-2-amine; 5-(4-isopropoxyphenyl)-N-((1s,4s)-4-methylcyclohexyl)-4-(tetrahydro-2H-pyran-3-yloxy)pyrimidin-2-amine; 5-(2-methyl-2H-indazol-6-yl)-N-((1s,4S)-4-methylcyclohexyl)-4-((R)-tetrahydrofuran-3-yloxy)pyrimidin-2-amine; 5-(4-isopropoxyphenyl)-N-((1s,4R)-4-methylcyclohexyl)-4-4(S)-tetrahydrofuran-3-yl)methoxy)pyrimidin-2-amine; 2-(4-(2-((1s,4s)-4-methylcyclohexylamino)-4-((1-methylcyclopropyl)methoxy)pyrimidin-5-yl)phenoxy)acetonitrile; 4-methoxy-5-(2-methylbenzo[d]oxazol-6-yl)-N-((1s,4s)-4-methylcyclohexyl)pyrimidin-2-amine; N-((1s,4s)-4-methylcyclohexyl)-4-((tetrahydro-2H-pyran-4-yl)methoxy)-5-(4-(trifluoromethoxy)phenyl)pyrimidin-2-amine; 5-(4-isopropoxyphenyl)-N-((1s,4s)-4-methylcyclohexyl)-4-((tetrahydro-2H-pyran-4-yl)methoxy)pyrimidin-2-amine; N-((1s,4s)-4-methylcyclohexyl)-4-((1-methylcyclopropyl)methoxy)-5-(4-(trifluoromethoxy)phenyl)pyrimidin-2-amine; 5-(4-isopropoxyphenyl)-4-methoxy-6-methyl-N-((1s,4s)-4-methylcyclohexyl)pyrimidin-2-amine; N4-(2-methoxyethyl)-N4-methyl-N2-((1s,4s)-4-methylcyclohexyl)-5-(4-(trifluoromethoxy)phenyl)pyrimidine-2,4-diamine; N-((1s,4s)-4-methylcyclohexyl)-4-((tetrahydro-2H-pyran-2-yl)methoxy)-5-(4-(trifluoromethoxy)phenyl)pyrimidin-2-amine; 4-methoxy-6-methyl-5-(2-methyl-2H-indazol-6-yl)-N-((1s,4s)-4-methylcyclohexyl)pyrimidin-2-amine; 4-((2,5-dimethyloxazol-4-yl)methoxy)-5-(2-methyl-2H-indazol-6-yl)-N-((1s,4s)-4-methylcyclohexyl)pyrimidin-2-amine; 4-((2,5-dimethyloxazol-4-yl)methoxy)-5-(4-isopropoxyphenyl)-N-((1s,4s)-4-methylcyclohexyl)pyrimidin-2-amine; 5-(2-methyl-2H-indazol-5-yl)-N-((1s,4S)-4-methylcyclohexyl)-4-((R)-tetrahydrofuran-3-yloxy)pyrimidin-2-amine; 5-(2,3-dihydrobenzo[b][1,4]dioxin-6-yl)-N-((1s,4S)-4-methylcyclohexyl)-4-((R)-tetrahydrofuran-3-yloxy)pyrimidin-2-amine; 4-(3-methoxyphenoxy)-5-(2-methyl-2H-indazol-6-yl)-N-((1s,4s)-4-methylcyclohexyl)pyrimidin-2-amine; 4-(3,5-dimethylisoxazol-4-yl)-5-(4-isopropoxyphenyl)-N-((1s,4s)-4-methylcyclohexyl)pyrimidin-2-amine; 2-(4-(4-(cyclopentylmethoxy)-2-((1s,4s)-4-methylcyclohexylamino)pyrimidin-5-yl)phenoxy)acetonitrile; 5-(4-isopropoxyphenyl)-N-((1s,4S)-4-methylcyclohexyl)-4-(((R)-tetrahydrofuran-2-yl)methoxy)pyrimidin-2-amine; N-((1s,4s)-4-methylcyclohexyl)-5-(6-(tetrahydro-2H-pyran-4-yloxy)pyridin-3-yl)-4-((R)-tetrahydrofuran-3-yloxy)pyrimidin-2-amine; 4-methyl-5-(2-methyl-2H-indazol-6-yl)-N-((1s,4S)-4-methylcyclohexyl)-6-((R)-tetrahydrofuran-3-yloxy)pyrimidin-2-amine; 5-(2-methyl-2H-indazol-6-yl)-N-((1s,4S)-4-methylcyclohexyl)-4-4(R)-tetrahydrofuran-2-yl)methoxy)pyrimidin-2-amine; 5-(2,3-dihydrobenzo[b][1,4]dioxin-6-yl)-N-((1s,4S)-4-methylcyclohexyl)-4-(((R)-tetrahydrofuran-2-yl)methoxy)pyrimidin-2-amine; 5-(2,3-dihydrobenzo[b][1,4]dioxin-6-yl)-N-((1s,4S)-4-methylcyclohexyl)-4-((tetrahydro-2H-pyran-4-yl)methoxy)pyrimidin-2-amine; 5-(2,3-dihydrobenzo[b][1,4]dioxin-6-yl)-N-((1s,4S)-4-methylcyclohexyl)-4-((tetrahydro-2H-pyran-2-yl)methoxy)pyrimidin-2-amine; N-((1s,4S)-4-methylcyclohexyl)-5-(4-morpholinophenyl)-4-((R)-tetrahydrofuran-3-yloxy)pyrimidin-2-amine; 5-(2,3-dihydrobenzo[b][1,4]dioxin-6-yl)-N-((1s,4R)-4-methylcyclohexyl)-4-(((S)-tetrahydrofuran-3-yl)methoxy)pyrimidin-2-amine; 5-(4-(5-methyl-1,3,4-oxadiazol-2-yl)phenyl)-N-((1s,4S)-4-methylcyclohexyl)-4-((R)-tetrahydrofuran-3-yloxy)pyrimidin-2-amine; 5-(3,4-dihydro-2H-benzo[b][1,4]dioxepin-7-yl)-N-((1s,4S)-4-methylcyclohexyl)-4-((R)-tetrahydrofuran-3-yloxy)pyrimidin-2-amine; 5-(1-methyl-1H-indazol-5-yl)-N-((1s,4S)-4-methylcyclohexyl)-4-((R)-tetrahydrofuran-3-yloxy)pyrimidin-2-amine; 5-(2-methylbenzo[d]oxazol-6-yl)-N-((1s,4S)-4-methylcyclohexyl)-4-((R)-tetrahydrofuran-3-yloxy)pyrimidin-2-amine; 5-(2-methylbenzo[d]thiazol-5-yl)-N-((1s,4S)-4-methylcyclohexyl)-4-((R)-tetrahydrofuran-3-yloxy)pyrimidin-2-amine; 5-(2,3-dihydrobenzo[b][1,4]dioxin-6-yl)-4-methyl-N-((1s,4S)-4-methylcyclohexyl)-6-((R)-tetrahydrofuran-3-yloxy)pyrimidin-2-amine; methyl 3-(5-(2-methyl-2H-indazol-6-yl)-2-((1s,4s)-4-methylcyclohexylamino)pyrimidin-4-yloxy)pyrrolidine-1-carboxylate; 5-(2-methyl-2H-indazol-5-yl)-N-((1s,4s)-4-methylcyclohexyl)-4-((tetrahydro-2H-pyran-4-yl)methoxy)pyrimidin-2-amine; N-((1s,4S)-4-methylcyclohexyl)-5-(6-(piperidin-1-yl)pyridin-3-yl)-4-((R)-tetrahydrofuran-3-yloxy)pyrimidin-2-amine; 5-(4-methyl-3,4-dihydro-2H-benzo[b][1,4]oxazin-7-yl)-N-((1s,4S)-4-methylcyclohexyl)-4-((R)-tetrahydrofuran-3-yloxy)pyrimidin-2-amine; 5-(2,2-difluorobenzo[d][1,3]dioxol-5-yl)-N-((1s,4S)-4-methylcyclohexyl)-4-((R)-tetrahydrofuran-3-yloxy)pyrimidin-2-amine; 5-(benzo[c][1,2,5]oxadiazol-5-yl)-N-((1s,4S)-4-methylcyclohexyl)-4-((R)-tetrahydrofuran-3-yloxy)pyrimidin-2-amine; 5-(2-methylbenzo[d]oxazol-5-yl)-N-((1s,4S)-4-methylcyclohexyl)-4-((R)-tetrahydrofuran-3-yloxy)pyrimidin-2-amine; 5-(2,3-dihydrobenzo[b][1,4]dioxin-6-yl)-N-((1s,4s)-4-methylcyclohexyl)-4-(oxetan-3-yloxy)pyrimidin-2-amine; 5-(1-methyl-1H-indazol-5-yl)-N-((1s,4s)-4-methylcyclohexyl)-4-(oxetan-3-yloxy)pyrimidin-2-amine; N-((1s,4s)-4-methylcyclohexyl)-5-(4-morpholinophenyl)-4-(oxetan-3-yloxy)pyrimidin-2-amine; N-((1s,4S)-4-methylcyclohexyl)-5-(1-methylindolin-5-yl)-4-((R)-tetrahydrofuran-3-yloxy)pyrimidin-2-amine; 5-(2-((1s,4S)-4-methylcyclohexylamino)-4-((R)-tetrahydrofuran-3-yloxy)pyrimidin-5-yl)indolin-2-one; 5-(2,3-dihydrobenzo[b][1,4]dioxin-6-yl)-N-((1s,4S)-4-methylcyclohexyl)-4-((R)-tetrahydro-2H-pyran-3-yloxy)pyrimidin-2-amine; 5-(5-chloro-2-methoxypyridin-4-yl)-N-((1s,4S)-4-methylcyclohexyl)-4-((R)-tetrahydrofuran-3-yloxy)pyrimidin-2-amine; 5-(2-(methoxymethyl)benzo[d]oxazol-5-yl)-N-((1s,4S)-4-methylcyclohexyl)-4-((R)-tetrahydrofuran-3-yloxy)pyrimidin-2-amine; N-((1s,4s)-4-methylcyclohexyl)-5-(4-morpholinophenyl)-4-((tetrahydro-2H-pyran-4-yl)methoxy)pyrimidin-2-amine; 5-(1-methyl-1H-indazol-5-yl)-N-((1s,4s)-4-methylcyclohexyl)-4-((tetrahydro-2H-pyran-4-yl)methoxy)pyrimidin-2-amine;

5-(2-methylbenzo[d]oxazol-5-yl)-N-((1s,4s)-4-methylcyclohexyl)-4-((tetrahydro-2H-pyran-4-yl)methoxy)pyrimidin-2-amine; 5-(1-methyl-1H-indazol-5-yl)-N-((1s,4S)-4-methylcyclohexyl)-4-((R)-tetrahydro-2H-pyran-3-yloxy)pyrimidin-2-amine; 5-(2-methyl-2H-indazol-5-yl)-N-((1s,4S)-4-methylcyclohexyl)-4-((R)-tetrahydro-2H-pyran-3-yloxy)pyrimidin-2-amine; N-((1s,4S)-4-methylcyclohexyl)-5-(4-morpholinophenyl)-4-((R)-tetrahydro-2H-pyran-3-yloxy)pyrimidin-2-amine; 1-methyl-5-(2-((1s,4S)-4-methylcyclohexylamino)-4-((R)-tetrahydrofuran-3-yloxy)pyrimidin-5-yl)indolin-2-one; 5-(2-methylbenzo[d]thiazol-5-yl)-N-((1s,4s)-4-methylcyclohexyl)-4-(oxetan-3-yloxy)pyrimidin-2-amine; N-((1s,4s)-4-methylcyclohexyl)-4-(oxetan-3-yloxy)-5-(6-(piperidin-1-yl)pyridin-3-yl)pyrimidin-2-amine; 5-(3,4-dihydro-2H-benzo[b][1,4]dioxepin-7-yl)-N-((1s,4s)-4-methylcyclohexyl)-4-(oxetan-3-yloxy)pyrimidin-2-amine; 5-(2-methyl-1,3-benzoxazol-5-yl)-N-(4-methylcyclohexyl)-4-(oxetan-3-yloxy)pyrimidin-2-amine; 5-(2-methyl-2H-indazol-5-yl)-N-(4-methylcyclohexyl)-4-(oxetan-3-yloxy)pyrimidin-2-amine; 5-(2-methyl-2H-indazol-6-yl)-N-(4-methylcyclohexyl)-4-(oxetan-3-yloxy)pyrimidin-2-amine; 4-[(2R)-1,4-dioxan-2-ylmethoxy]-N-(4-methylcyclohexyl)-5-[4-(morpholin-4-yl)phenyl]pyrimidin-2-amine; isopropyl 3-(5-(2,3-dihydrobenzo[b][1,4]dioxin-6-yl)-2-((1s,4s)-4-methylcyclohexylamino)pyrimidin-4-yloxy)pyrrolidine-1-carboxylate; 1-(3-(5-(2,3-dihydrobenzo[b][1,4]dioxin-6-yl)-2-((1s,4S)-4-methylcyclohexylamino)pyrimidin-4-yloxy)pyrrolidin-1-yl)ethanone; or a pharmaceutically acceptable salt, prodrug or N-oxide thereof.

Another aspect of the invention provides a pharmaceutical composition comprising a compound disclosed herein formulated together with one or more pharmaceutically acceptable carriers. These formulations include those suitable for oral, rectal, topical, buccal and parenteral (e.g., subcutaneous, intramuscular, intradermal, or intravenous) administration, although the most suitable form of administration in any given case will depend on the degree and severity of the condition being treated and on the nature of the particular compound being used.

III. THERAPEUTIC APPLICATIONS

The invention further provides methods of modulating the activity of one or more cystic fibrosis transmembrane regulators comprising exposing said receptor to a compound of the invention, e.g., a compound of formula I, Ia, II, or III. The invention further provides methods of treating a disease associated with expression or activity of one or more cystic fibrosis transmembrane regulators in a patient comprising administering to the patient a therapeutically effective amount of a compound of the invention.

These compounds and pharmaceutically acceptable compositions are useful for treating or lessening the severity of a variety of diseases, disorders, or conditions, including, but not limited to, cystic fibrosis, hereditary emphysema, hereditary hemochromatosis, coagulation-cibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, secretory diarrhea or polycystic kidney disease, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry eye disease, or Sjogren's disease.

One embodiment of the invention provides a method of treating airway inflammation comprising administering to a subject in need thereof a therapeutically effective amount of a compound of the invention, e.g., a compound of formula I, Ia, II, or III. The methods disclosed herein may involve treating cystic fibrosis.

One embodiment provides a method of treating cystic fibrosis comprising administering to a subject in need thereof a therapeutically effective amount of a compound described herein, e.g., a compound of formula I, Ia, II, or III. In certain embodiments, the compound has the following formula:

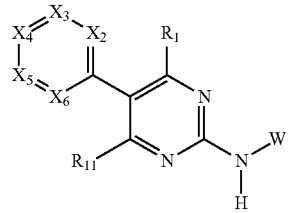

wherein $X_2$ is $CR_2$ or N, $X_3$ is $CR_3$ or N, $X_4$ is $CR_4$ or N, $X_5$ is $CR_5$ or N, and $X_6$ is $CR_6$ or N, where one or two of $X_2$-$X_6$ can be N;

W is selected from the group consisting of $C_1$-$C_{10}$alkyl and $C_4$-$C_{10}$cycloalkyl, optionally substituted with one or two substituents independently, for each occurrence, selected from the group consisting of $C_1$-$C_6$alkyl, $C_3$-$C_{10}$cycloalkyl, —$OC_1$-$C_6$alkyl, —O—$C_3$-$C_{10}$cycloalkyl, —$CF_3$, and fluoro;

$R_1$ and $R_{11}$ are each independently selected from the group consisting of hydrogen, $C_1$-$C_6$alkyl, $C_3$-$C_{10}$cycloalkyl, —$OC_1$-$C_6$alkyl, —O—$C_3$-$C_{10}$cycloalkyl, —$CF_3$, —CN, —$OCF_2H$, —$OCH_2F$, —$OCF_3$, halogen, —$CONR_7R_{10}$, —$NR_7R_{10}$, —$NR_7COR_8$, —$NR_7SO_2R_9$, aryl, heteroaryl, and —$SO_2R_9$;

$R_2$ and $R_6$ are each independently selected from the group consisting of hydrogen, F, Cl, Br, I, —$CF_3$, —$OCF_3$, —$OCHF_2$, —$OCH_2F$, $C_1$-$C_6$alkyl, $C_3$-$C_{10}$cycloalkyl, $C_3$-$C_{10}$heterocyclyl, —$OC_1$-$C_6$alkyl, —O—$C_3$-$C_{10}$cycloalkyl, —$NR_7COR_8$, —$NR_7SO_2R_9$, —$CONR_7R_{10}$, —$SO_2NR_7R_{10}$, —CN, aryl, heteroaryl, —$NR_7R_{10}$, and —$SO_2R_9$;

$R_3$ and $R_5$ are each independently selected from the group consisting of hydrogen, halogen, —$CF_3$, —$OCF_3$, —$OCHF_2$, —$OCH_2F$, $C_1$-$C_6$alkyl, $C_3$-$C_{10}$cycloalkyl, $C_3$-$C_{10}$heterocyclyl, —$OC_1$-$C_6$alkyl, —O—$C_3$-$C_{10}$cycloalkyl, —$CONR_7R_{10}$, —$NR_7COR_8$, $NR_7SO_2R_9$, —$SO_2NR_7R_{10}$, —CN, aryl, heteroaryl, —$NR_7R_{10}$, and —$SO_2R_9$;

$R_4$ is selected from the group consisting of hydrogen, F, Cl, Br, I, —$CF_3$, —CN, —$OCHF_2$, —$OCH_2F$, —$OCF_3$, $C_1$-$C_6$alkyl, $C_3$-$C_{10}$cycloalkyl, $C_3$-$C_{10}$heterocyclyl, —$OC_1$-$C_6$alkyl, —$OC_3$-$C_{10}$cycloalkyl, —$NR_7SO_2R_9$, —$NR_7COR_8$, —$CONR_7R_{10}$, —$SO_2NR_7R_{10}$, aryl, heteroaryl, —$NR_7R_{10}$, and —$SO_2R_9$; or any two adjacent variables selected from $R_2$, $R_3$, $R_4$, $R_5$, and $R_6$ can be taken together to form a cycloalkyl, aryl, heteroaryl or heterocyclyl, optionally substituted by one, two, or three substituents independently, for each occurrence, selected from the group consisting of alkoxy, alkyl, alkenyl, alkynyl, amido, amino, aryl, cyano, cycloalkyl, haloalkyl, halogen, heteroaryl, heterocyclyl, hydroxyl, nitro and sulfonyl;

$R_7$ and $R_{10}$ are each independently selected from the group consisting of hydrogen, alkyl, and cycloalkyl, optionally substituted with one or two substituents independently, for each occurrence, selected from the group consisting of halogen, cyano, hydroxy, nitro, and alkoxy, or $R_7$ and $R_{10}$ can be taken together to form a heterocyclyl, optionally substituted by one, two, or three substituents independently, for each occurrence, selected from the group consisting of alkoxy, alkyl, alkenyl, alkynyl, amido, amino, aryl, cyano, cycloalkyl, haloalkyl, halogen, heteroaryl, heterocyclyl, hydroxyl, nitro and sulfonyl;

$R_8$ is selected from the group consisting of alkoxy, alkyl, alkenyl, alkynyl, amido, amino, aryl, cycloalkoxy, cycloalkyl, haloalkyl, heteroaryl, and heterocyclyl;

$R_9$ is selected from the group consisting of alkyl, alkenyl, alkynyl, amido, amino, aryl, cycloalkoxy, cycloalkyl, haloalkyl, heteroaryl, and heterocyclyl;

or pharmaceutically acceptable salts, prodrugs, or N-oxides thereof.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Exemplary pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin. Compositions for inhalation or insufflation include solutions and suspensions in pharmaceutically acceptable, aqueous or organic solvents, or mixtures thereof, and powders.

Advantageously, the invention also provides kits for use by a consumer having, or at risk of having, a disease or condition associated with cystic fibrosis transmembrane regulators. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . ." etc.

Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

EXAMPLES

The compounds of the present invention can be prepared in a number of ways well known to one skilled in the art of organic synthesis. More specifically, compounds of the invention may be prepared using the reactions and techniques described herein. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available (such as through Aldrich Chemicals Co. (Milwaukee, Wis.), Alfa Aesar (Ward Hill, Mass.), Maybridge Chemical Company, Ltd. (Cornwall, England), Ryan Scientific Inc. (Mt. Pleasant, S.C.), Combi-Blocks, Inc. (San Diego, Calif.), and Focus Synthesis LLC (San Diego, Calif.)) or are readily prepared by standard methods from known materials.

Unless specified otherwise, starting materials are generally available from commercial sources NMR spectra were recorded on a Varian AS 400 (Varian Inc., Palo Alto, Calif.) at room temperature at 400 MHz for proton, or a Bruker Avance 300 UltraShield™ (Bruker BioSpin Corp., Billerica, Mass.) at 300 MHz for proton and at 282 MHz for $^{19}$F. Chemical shifts are expressed in parts per million (δ) relative to residual solvent as an internal reference. The peak shapes are denoted as follows: s, singlet; d, doublet; t, triplet; q, quartet; m, multiplet; bs, broad singlet; bd, broad doublet. Liquid chromatography electrospray ionization mass spectra (LCMS) were obtained on an Agilent HP 1100 instrument (Agilent Technologies, Foster City, Calif.). Where the intensity of chlorine or bromine-containing ions are described, the expected intensity ratio was observed (approximately 3:1 for $^{35}$Cl/$^{37}$Cl-containing ions and 1:1 for $^{79}$Br/$^{81}$Br-containing ions) and the intensity of only the lower mass ion is given. MS peaks are reported for all examples. Microwave reactions were performed on a Biotage Emrys™ Optimizer (Biotage, Charlottesville, Va.).

Column chromatography was performed on a CombiFlash Companion™ (Teledyne ISCO Inc., Lincoln, Nebr.) with different size of RediSep Rf columns. Preparative thin-layer chromatography was performed using Analtech silica gel GF with UV254 indicator (Analtech Inc., Newark, Del.) on 20 cm×20 cm×1 mm plates. When needed, multiple plates are used. After eluting the plates with the indicated solvent, the desired band is marked under UV light, and scraped off. The desired product is extracted from the silica using a polar solvent system (e.g., 20% methanol in methylene chloride or 100% EtOAc). Preparative HPLC was performed on a Varian Dynamax instrument (Varian Inc., Palo Alto, Calif.) using a Kromasil 100-10-C18 250 mm×20 mm column (EKA Chemicals, 80 Bohus, Sweden).

Example 1

General Experimental Procedure

Scheme 1 illustrates a general procedure for preparing a compound of the present invention where $R_1$ is H, or —OCH$_3$, or —NH$_2$. Compound 1A can be prepared by amination of a desired 2-chloropyrimidine with a desired amine according to methods known in the art. For example, compound 1A can be prepared by heating a mixture of a commercially available 2-chloropyrimidine and a desired amine R—NH$_2$ in the presence of triethylamine in ethanol at about 75° C. for about 8-24 h. Compound 1B can be prepared from compound 1A through coupling of a desired boronic acid under Suzuki conditions, where X may be selected from, for example, alkyl, alkoxy, amino, etc.

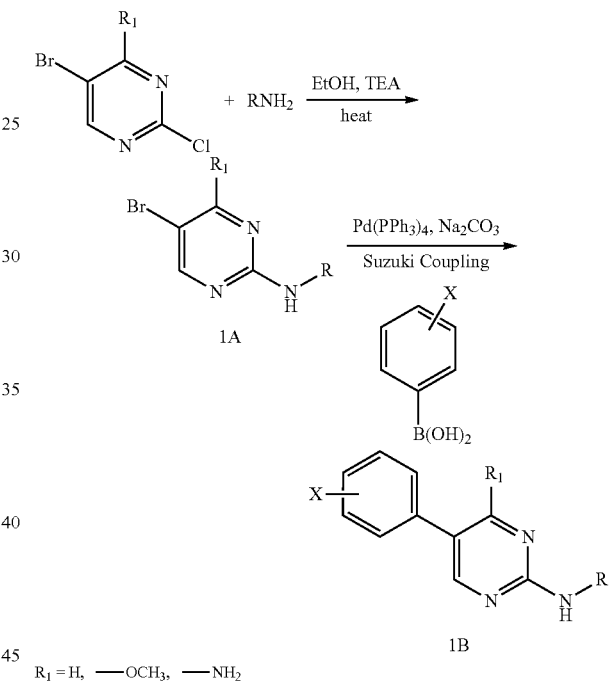

Preparation of 5-Bromo-N-((1S,4S)-4-methylcyclo-hexyl)pyrimidin-2-amine (1a) and 5-Bromo-N-((1R,4R)-4-methylcyclohexyl)pyrimidin-2-amine (1b)

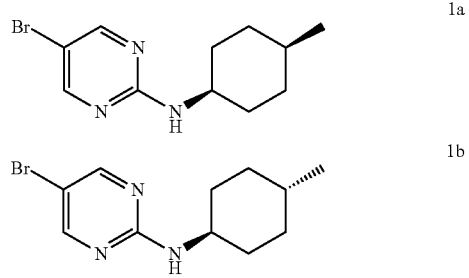

To a solution of 5-bromo-2-chloropyrimidine (3.86 g, 20.0 mmol) in EtOH (6.00 ml) was added 4-methylcyclohexanamine (mixture of cis and trans isomers, 2.56 mL, 20.0 mmol) followed by triethylamine (8.00 mL, 57.5 mmol). The mixture was heated in a microwave oven at 100° C. for 1 hour. After cooling to room temperature, the reaction mixture was diluted with CH$_2$Cl$_2$, and washed with saturated NaCl solution. The organic layer was separated, dried (Na$_2$SO$_4$) and concentrated in vacuo. The residue was purified three times by ISCO chromatography (120 g silica column, 0-30% EtOAc in hexanes; R$_f$~0.50 with hexanes:EtOAc=8:1 for 1a and R$_f$~0.45 with hexanes:EtOAc=8:1 for 1b) to give 2.80 g (52%) of 1a and 2.03 g (38%) of 1b as white solids. 1a: $^1$H NMR (CDCl$_3$, 300 MHz) δ 8.27 (s, 2H), 5.30 (bd, 1H, J=5.5 Hz), 4.05-3.99 (m, 1H), 1.84-1.45 (m, 7H), 1.27-1.18 (m, 2H), 0.94 (d, 3H, J=6.5 Hz); MS (ESI, M+H$^+$) C$_{11}$H$_{17}$BrN$_3$, calcd. 270.1, found 270.0. 1b: $^1$H NMR (CDCl$_3$, 300 MHz) δ 8.25 (s, 2H), 4.98 (bd, 1H, J=7.1 Hz), 3.72-3.61 (m, 1H), 2.10-2.06 (m, 2H), 1.77-1.73 (m, 2H), 1.45-1.30 (m, 1H), 1.26-1.02 (m, 4H), 0.92 (d, 3H, J=6.5 Hz); MS (ESI, M+H$^+$) C$_{11}$H$_{17}$BrN$_3$, calcd. 270.1, found 270.0.

Example 2

General Experimental Procedure

Scheme 2 illustrates a general procedure for preparing a compound of the present invention where R$_1$ is —NR$_7$R$_{10}$. Compound 2A can be prepared by amination of a commercially available 2,4-dichloro-5-bromo-pyrimidine with a desired amine R$_7$R$_{10}$NH$_2$ using methods well-known in the art. For example, compound 2A can be prepared by treating the pyrimidine in CH$_3$CN with a desired amine at about −20° C. to 45° C. in the presence of triethylamine. Compound 2A can be converted to compound 2B according to the methods described in Scheme 1. Compound 2C can be prepared from compound 2B and a desired boronic acid via Suzuki coupling.

SCHEME 2

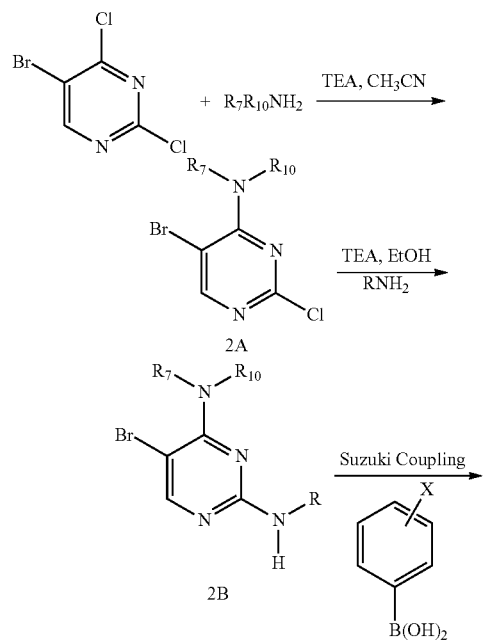

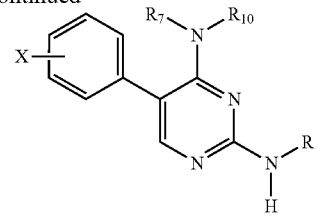

Preparation of Intermediates 5-Bromo-N-((1S,4S)-4-(trifluoromethyl)cyclohexyl)pyrimidin-2-amine (2a) and 5-Bromo-N-((1R,4R)-4-(trifluoromethyl)cyclohexyl)pyrimidin-2-amine (2b)

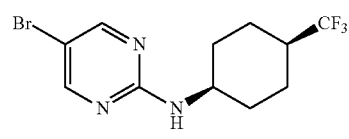

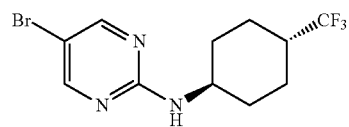

The title compounds were prepared according to the procedures described in Example 1 for intermediates 1a and 1b. A mixture of 5-bromo-2-chloropyrimidine (475 mg, 2.46 mmol), 4-(trifluoromethyl)cyclohexanamine (mixture of cis and trans isomers, 411 mg, 2.46 mmol) and triethylamine (2.00 mL, 14.4 mmol) in EtOH (2.00 ml) was stirred at 100° C. in a microwave oven for 1 h. The crude product was purified by ISCO chromatography (120 g silica column, 0-40% EtOAc in hexanes; R$_f$~0.35 with hexanes:EtOAc=8:1 for 2a and R$_f$~0.25 with hexanes:EtOAc=8:1 for 2b) to give 280 mg (35%) of 2a and 172 mg (22%) of 2b as white solids. 2a: $^1$H NMR (CDCl$_3$, 300 MHz) δ 8.28 (s, 2H), 5.31 (bd, 1H, J=5.8 Hz), 4.15-4.10 (m, 1H), 2.17-1.97 (m, 3H), 1.85-1.79 (m, 2H), 1.70-1.52 (m, 4H); $^{19}$F NMR (CDCl$_3$, 282 MHz) δ −73.1 (d, 3 F, J=8.3 Hz); MS (ESI, M+H$^+$) C$_{11}$H$_{14}$BrF$_3$N$_3$, calcd. 324.0, found 324.0. 2b: $^1$H NMR (CDCl$_3$, 300 MHz) δ 8.27 (s, 2H), 4.99 (bd, 1H, J=6.7 Hz), 3.81-3.68 (m, 1H), 2.25-2.21 (m, 2H), 2.05-1.99 (m, 3H), 1.53-1.44 (m, 2H), 1.29-1.13 (m, 2H); $^{19}$F NMR (CDCl$_3$, 282 MHz) δ −73.6 (d, 3 F, J=8.6 Hz); MS (ESI, M+H$^+$) C$_{11}$H$_{14}$BrF$_3$N$_3$, calcd. 324.0, found 324.0.

Example 3

General Experimental Procedure

Scheme 3 illustrates a general procedure for preparing a compound of the present invention where R$_1$ is alkoxy or cycloalkoxy. Compound 3A can be prepared from a commercially available 2,4-dichloro-5-bromo-pyrimidine and a desired alcohol using methods known in the art. For example, compound 3A can be prepared by treating the pyrimidine in THF with a desired alkoxide at about −20° C. to 60° C. for about 8-24 h. The alkoxide can be generated from a corresponding alcohol and NaH in THF at about −20° C. to 60° C.

for about 2-24 h or according to methods known in the art. Compound 3A can be converted to compound 3C by amination followed by Suzuki coupling as described in Scheme 3 below.

SCHEME 3

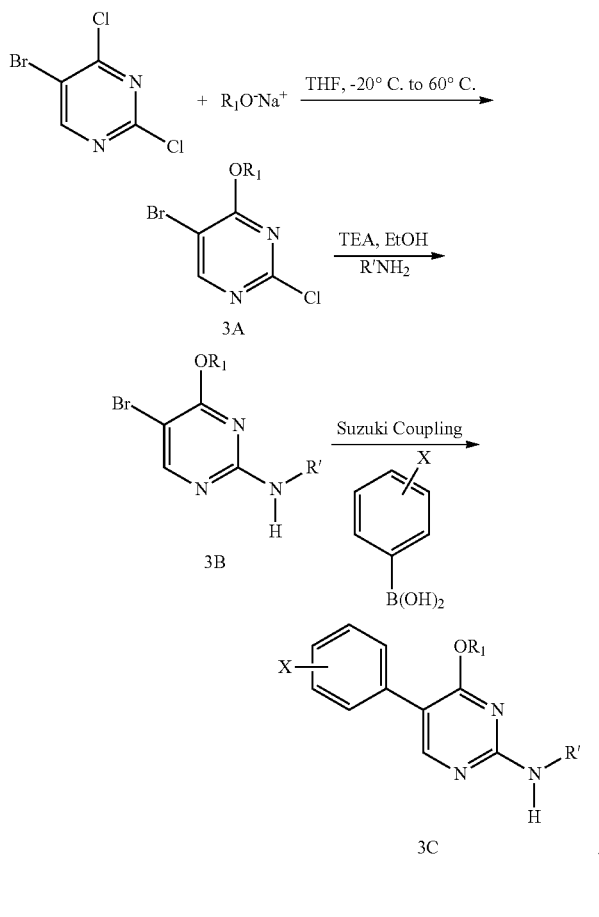

Preparation of Intermediates 5-Bromo-4-methoxy-N-((1S,4S)-4-methylcyclohexyl)pyrimidin-2-amine (3a) and 5-Bromo-4-methoxy-N-((1R,4R)-4-methylcyclohexyl)pyrimidin-2-amine (3b)

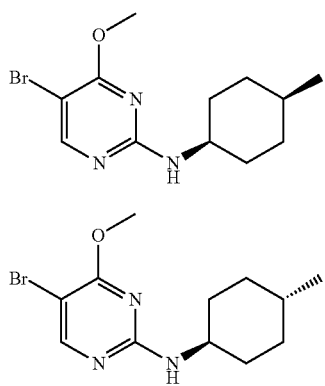

To a solution of 5-bromo-2-chloro-4-methoxypyrimidine (1.00 g, 4.49 mmol) in EtOH (3.00 mL) was added 4-methylcyclohexanamine (mixture of cis and trans isomers, 523 mg, 4.62 mmol) followed by triethylamine (1.87 mL, 13.4 mmol). The mixture was stirred at 100° C. for 19 h. After cooling to room temperature, the reaction mixture was diluted with $CH_2Cl_2$, and washed with saturated NaCl solution. The organic layer was separated, dried ($Na_2SO_4$) and concentrated in vacuo. The residue was purified by ISCO chromatography (120 g silica column, 0-40% EtOAc in hexanes; $R_f$~0.35 with hexanes:EtOAc=8:1 for 3a and $R_f$~0.30 with hexanes:EtOAc=8:1 for 3b) to give 440 mg (33%) of 3a and 309 mg (23%) of 3b as white solids. 3a: $^1$H NMR ($CDCl_3$, 300 MHz) δ 8.08 (s, 1H), 5.15 (b, 1H), 4.05-3.99 (m, 1H), 3.96 (s, 3H), 1.90-1.76 (m, 2H), 1.70-1.51 (m, 5H), 1.28-1.17 (m, 2H), 0.94 (d, 3H, J=6.4 Hz); MS (ESI, M+H$^+$) $C_{12}H_{19}BrN_3O$, calcd. 300.1, found 300.0. 3b: $^1$H NMR ($CDCl_3$, 300 MHz) δ 8.08 (s, 1H), 4.85 (bd, 1H, J=6.3 Hz), 3.95 (s, 3H), 3.70-3.65 (m, 1H), 2.11-2.07 (m, 2H), 1.78-1.73 (m, 2H), 1.41-1.35 (m, 1H), 1.26-1.06 (m, 4H), 0.92 (d, 3H, J=6.5 Hz); MS (ESI, M+H$^+$) $C_{12}H_{19}BrN_3O$, calcd. 300.1, found 300.0.

Example 4

Preparation of N-((1S,4S)-4-Methylcyclohexyl)-5-(4-(trifluoromethoxy)phenyl)pyrimidin-2-amine

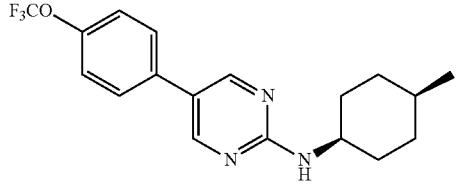 [SMILES: C[C@H]1CC[C@@H](Nc2ncc(-c3ccc(OC(F)(F)F)cc3)cn2)CC1]

To a solution of 5-bromo-N-((1S,4S)-4-methylcyclohexyl)pyrimidin-2-amine (1a) (27.0 mg, 100 μmol) in $CH_3CN$ (2.00 mL) was added 4-(trifluoromethoxy)phenylboronic acid (41.2 mg, 200 μmol) followed by Pd(PPh$_3$)$_4$ (5.80 mg, 5.00 μmol) and 2 M $Na_2CO_3$ solution (620 mL). The mixture was stirred in a microwave oven at 100° C. for 30 minutes. After cooling to room temperature, the reaction mixture was diluted with EtOAc, and washed with saturated NaCl solution. The organic layer was separated, dried ($Na_2SO_4$) and concentrated in vacuo. The residue was purified by ISCO chromatography (40 g silica column, 0-80% EtOAc in hexanes; $R_f$~0.25 with hexanes:EtOAc=8:1) and preparative TLC (100% $CH_2Cl_2$) to give 31.0 mg (88%) of the title compound as a white solid. $^1$H NMR ($CDCl_3$, 300 MHz) δ 8.49 (s, 2H), 7.50-7.47 (m, 2H), 7.29 (d, 2H, J=8.7 Hz), 5.41 (bd, 1H, J=7.7 Hz), 4.17-4.12 (m, 1H), 1.87-1.50 (m, 7H), 1.32-1.23 (m, 2H), 0.95 (d, 3H, J=6.4 Hz); $^{19}$F NMR ($CDCl_3$, 282 MHz) δ −58.9 (s, 3 F); MS (ESI, M+H$^+$) $C_{18}H_{21}F_3N_3O$, calcd. 352.2, found 352.2.

Example 5

Preparation of N-((1R,4R)-4-Methylcyclohexyl)-5-(4-(trifluoromethoxy)phenyl)pyrimidin-2-amine

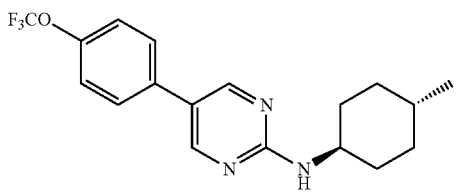 [SMILES: C[C@H]1CC[C@H](Nc2ncc(-c3ccc(OC(F)(F)F)cc3)cn2)CC1]

The title compound was prepared according to the procedure described in Example 4 using 5-bromo-N-((1R,4R)-4-methylcyclohexyl)pyrimidin-2-amine (1b) (54.0 mg, 200 µmol) and 4-(trifluoromethoxy)phenylboronic acid (82.4 mg, 400 µmol) as starting materials. The crude product was purified by ISCO chromatography (40 g silica column, 0-100% EtOAc in hexanes; $R_f$~0.20 with hexanes:EtOAc=8:1) to give 63.0 mg (90%) of the title compound as a white solid. $^1$H NMR (CDCl$_3$, 300 MHz) δ 8.48 (s, 2H), 7.49-7.46 (m, 2H), 7.30-7.27 (m, 2H), 5.10 (bd, 1H, J=7.8 Hz), 3.85-3.73 (m, 1H), 2.15-2.11 (m, 2H), 1.79-1.74 (m, 2H), 1.47-1.35 (m, 1H), 1.30-1.06 (m, 4H), 0.93 (d, 3H, J=6.5 Hz); $^{19}$F NMR (CDCl$_3$, 282 MHz) δ −57.9 (s, 3 F); MS (ESI, M+H$^+$) C$_{18}$H$_{21}$F$_3$N$_3$O, calcd. 352.2, found 352.2.

Example 6

Preparation of 5-(4-Isopropoxyphenyl)-N-((1S,4S)-4-(trifluoromethyl)cyclohexyl)pyrimidin-2-amine

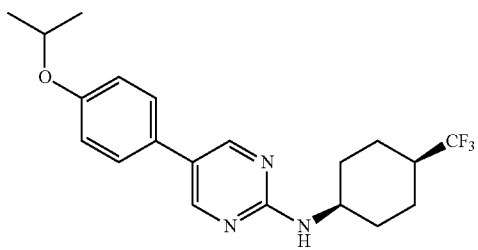 [SMILES: CC(C)Oc1ccc(-c2cnc(N[C@H]3CC[C@@H](C(F)(F)F)CC3)nc2)cc1]

The title compound was prepared according to the procedure described for Example 4 using 5-bromo-N-((1S,4S)-4-(trifluoromethyl)cyclohexyl)pyrimidin-2-amine (2a) (32.4 mg, 100 µmol) and 4-isopropoxyphenylboronic acid (36.0 mg, 200 µmol), Pd(PPh$_3$)$_4$ (5.80 mg, 5.00 µmol) as starting materials. The crude product was purified by ISCO chromatography (80 g silica column, 0-40% EtOAc in hexanes; $R_f$~0.45 with hexanes:EtOAc=2:1) to give 35.9 mg (95%) of the title compound as a white solid. $^1$H NMR (CDCl$_3$, 300 MHz) δ 8.48 (s, 2H), 7.39-7.36 (m, 2H), 6.98-6.95 (m, 2H), 5.33 (bd, 1H, J=7.3 Hz), 4.62-4.54 (m, 1H), 4.26-4.21 (m, 1H), 2.20-2.00 (m, 3H), 1.86-1.57 (m, 6H), 1.37 (d, 6H, J=6.0 Hz); $^{19}$F NMR (CDCl$_3$, 282 MHz) δ −73.1 (d, 3 F, J=8.3 Hz); MS (ESI, M+H$^+$) C$_{20}$H$_{25}$F$_3$N$_3$O, calcd. 380.2, found 380.2.

Example 7

Preparation of 5-(4-Isopropoxyphenyl)-4-methoxy-N-((1S,4S)-4-methylcyclohexyl)pyrimidin-2-amine

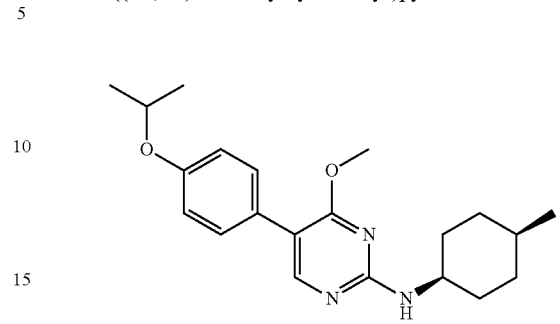

The title compound was prepared according to the procedure described in Example 1 using 5-bromo-4-methoxy-N-((1S,4S)-4-methylcyclohexyl)pyrimidin-2-amine (3a) (90.0 mg, 300 µmol) and 4-isopropoxyphenylboronic acid (81.0 mg, 450 µmol) as starting materials. The crude product was purified by ISCO chromatography (80 g silica column, 0-70% EtOAc in hexanes; $R_f$~0.70 with hexanes:EtOAc=2:1) and preparative HPLC (0-100% CH$_3$CN in H$_2$O) to give 94.6 mg (89%) of the title compound as a white solid. $^1$H NMR (CDCl$_3$, 300 MHz) δ 8.06 (s, 1H), 7.39-7.36 (m, 2H), 6.93-6.90 (m, 2H), 5.15 (bd, 1H, J=7.4 Hz), 4.61-4.53 (m, 1H), 4.15-4.10 (m, 1H), 3.93 (s, 3H), 1.88-1.80 (m, 2H), 1.73-1.52 (m, 5H), 1.36 (d, 6H, J=6.1 Hz), 1.33-1.25 (m, 2H), 0.96 (d, 3H, J=6.4 Hz); MS (ESI, M+H$^+$) C$_{21}$H$_{30}$N$_3$O$_2$, calcd. 356.2, found 356.2.

Examples 8-77

Compounds listed in Table 1 below were prepared using procedures analogous to those described above in Examples 4-7 using appropriate starting materials which are available commercially, prepared based on procedures known in the art, or prepared in a manner analogous to routes described above for other intermediates.

TABLE 1

| Example No. | Compound Name | MS Calc (M$^+$) | MS Found (M$^+$ + 1) |
|---|---|---|---|
| 8 | N-cyclohexyl-5-(3-(trifluoromethoxy)phenyl)pyrimidin-2-amine | 337.14 | 338.2 |
| 9 | N-cyclohexyl-5-(2-(trifluoromethoxy)phenyl)pyrimidin-2-amine | 337.14 | 338.2 |
| 10 | N-(4-(2-(cyclohexylamino)pyrimidin-5-yl)phenyl) isobutyramide | 338.21 | 339.2 |
| 11 | N-cyclohexyl-5-(2-fluorophenyl)pyrimidin-2-amine | 271.15 | 272.2 |
| 12 | N-cyclohexyl-5-(3-fluorophenyl)pyrimidin-2-amine | 271.15 | 272.2 |
| 13 | N-cyclopentyl-5-(4-(trifluoromethoxy)phenyl)pyrimidin-2-amine | 323.12 | 324.2 |
| 14 | N-cyclohexyl-5-(4-isopropoxyphenyl)pyrimidin-2-amine | 311.20 | 312.2 |
| 15 | N-cyclohexyl-5-(4-(pyrrolidin-1-ylsulfonyl)phenyl)pyrimidin-2-amine | 386.18 | 387.2 |
| 16 | (4-(2-(cyclohexylamino)pyrimidin-5-yl)phenyl)(pyrrolidin-1-yl)methanone | 350.21 | 351.2 |
| 17 | 4-(2-(cyclohexylamino)pyrimidin-5-yl)benzonitrile | 278.15 | 279.2 |
| 18 | N-cyclohexyl-5-(4-morpholinophenyl)pyrimidin-2-amine | 338.21 | 339.2 |

TABLE 1-continued

| Example No. | Compound Name | MS Calc (M+) | MS Found (M+ + 1) |
|---|---|---|---|
| 19 | 5-(4-(difluoromethoxy) phenyl)-N-((1s,4s)-4-methylcyclohexyl)pyrimidin-2-amine | 333.17 | 334.2 |
| 20 | N-cyclohexyl-5-(6-methylpyridin-3-yl)pyrimidin-2-amine | 268.17 | 269.2 |
| 21 | 5-(benzo[d][1,3]dioxol-5-yl)-N-cyclohexylpyrimidin-2-amine | 297.15 | 298.2 |
| 22 | N-cyclohexyl-5-(2,3-dihydrobenzo[b][1,4]dioxin-6-yl)pyrimidin-2-amine | 311.16 | 312.2 |
| 23 | 5-(4-isopropoxyphenyl)-N-((1s,4s)-4-methylcyclohexyl)pyrimidin-2-amine | 325.22 | 326.2 |
| 24 | 5-(6-methoxypyridin-3-yl)-N-((1s,4s)-4-methylcyclohexyl)pyrimidin-2-amine | 298.18 | 299.2 |
| 25 | 5-(2-methoxypyridin-4-yl)-N-((1s,4s)-4-methylcyclohexyl)pyrimidin-2-amine | 298.18 | 299.2 |
| 26 | 5-(2,2-difluorobenzo[d][1,3]dioxol-5-yl)-N-((1s,4s)-4-methylcyclohexyl) pyrimidin-2-amine | 347.14 | 348.2 |
| 27 | 5-(4-methoxyphenyl)-N-((1s,4s)-4-methylcyclohexyl)pyrimidin-2-amine | 297.18 | 298.2 |
| 28 | 5-(2,3-dihydrobenzofuran-5-yl)-N-((1s,4s)-4-methylcyclohexyl)pyrimidin-2-amine | 309.18 | 310.2 |
| 29 | N-((1s,4s)-4-methylcyclohexyl)-5-(4-(methylsulfonyl)phenyl)pyrimidin-2-amine | 345.15 | 346.2 |
| 30 | N-cyclohexyl-4-methoxy-5-(4-(trifluoromethoxy)phenyl)pyrimidin-2-amine | 367.15 | 368.2 |
| 31 | N-cycloheptyl-5-(4-(trifluoromethoxy)phenyl)pyrimidin-2-amine | 351.16 | 352.2 |
| 32 | N-(tetrahydro-2H-pyran-4-yl)-5-(4-(trifluoromethoxy)phenyl)pyrimidin-2-amine | 339.12 | 340.2 |
| 33 | N-cyclobutyl-5-(4-(trifluoromethoxy)phenyl)pyrimidin-2-amine | 309.11 | 310.0 |
| 34 | 5-(2,2-difluorobenzo[d][1,3]dioxol-4-yl)-N-((1s,4s)-4-methyl cyclohexyl)pyrimidin-2-amine | 347.14 | 348.2 |
| 35 | 5-(3-isopropoxyphenyl)-N-((1s,4s)-4-methylcyclohexyl)pyrimidin-2-amine | 325.22 | 326.2 |
| 36 | N-cyclohexyl-5-(4-isopropoxyphenyl)-4-methoxypyrimidin-2-amine | 341.21 | 342.2 |
| 37 | 5-(3-(difluoromethoxy)phenyl)-N-((1s,4s)-4-methylcyclohexyl)pyrimidin-2-amine | 333.17 | 334.2 |
| 38 | 5-(2-(difluoromethoxy)phenyl)-N-((1s,4s)-4-methylcyclohexyl)pyrimidin-2-amine | 333.17 | 334.2 |
| 39 | N-((1s,4s)-4-methylcyclohexyl)-5-(4-(pyrrolidin-1-yl)phenyl)pyrimidin-2-amine | 336.23 | 337.2 |
| 40 | N-cycloheptyl-5-(4-(difluoromethoxy)phenyl)pyrimidin-2-amine | 333.17 | 334.2 |
| 41 | N-((1s,4s)-4-methylcyclohexyl)-5-(4-(trifluoromethyl) phenyl)pyrimidin-2-amine | 335.16 | 336.2 |
| 42 | N-((1s,4s)-4-methylcyclohexyl)-5-(4-morpholinophenyl) pyrimidin-2-amine | 352.23 | 352.2 |
| 43 | 5-(4-(difluoromethoxy) phenyl)-N-((1s,4s)-4-ethylcyclohexyl)pyrimidin-2-amine | 347.18 | 348.2 |
| 44 | N-((1s,4s)-4-ethylcyclohexyl)-5-(4-isopropoxyphenyl)pyrimidin-2-amine | 339.23 | 340.2 |
| 45 | 5-(4-cyclobutoxyphenyl)-N-((1s,4s)-4-methylcyclohexyl)pyrimidin-2-amine | 337.22 | 338.2 |
| 46 | N-cyclopentyl-5-(4-(difluoromethoxy)phenyl)pyrimidin-2-amine | 305.13 | 306.2 |
| 47 | N-(cyclohexylmethyl)-5-(4-(difluoromethoxy)phenyl)pyrimidin-2-amine | 333.17 | 334.2 |
| 48 | 5-(4-(difluoromethoxy) phenyl)-N-(tetrahydro-2H-pyran-3-yl)pyrimidin-2-amine | 321.13 | 322.2 |
| 49 | N-((1s,4s)-4-methylcyclohexyl)-5-(2,4,6-trimethoxyphenyl)pyrimidin-2-amine | 357.21 | 358.2 |
| 50 | N-((1s,4s)-4-methylcyclohexyl)-5-(6-(piperidin-1-yl)pyridin-3-yl)pyrimidin-2-amine | 351.24 | 352.2 |
| 51 | N-cyclopentyl-5-(4-isopropoxyphenyl)pyrimidin-2-amine | 297.18 | 298.2 |
| 52 | N-(4,4-difluorocyclohexyl)-5-(4-(difluoromethoxy)phenyl)pyrimidin-2-amine | 355.13 | 356.2 |
| 53 | 5-(4-(cyclopropylmethoxy)phenyl)-N-((1s,4s)-4-methylcyclohexyl)pyrimidin-2-amine | 337.22 | 338.2 |
| 54 | N-((1s,4s)-4-methylcyclohexyl)-5-(4-(2,2,2-trifluoroethoxy)phenyl)pyrimidin-2-amine | 365.17 | 366.2 |
| 55 | 5-(3-fluoro-4-(2,2,2-trifluoroethoxy)phenyl)-N-((1s,4s)-4-methylcyclohexyl)pyrimidin-2-amine | 383.16 | 384.2 |
| 56 | 5-(4-fluoro-3-(2,2,2-trifluoroethoxy)phenyl)-N-((1s,4s)-4-methylcyclohexyl)pyrimidin-2-amine | 383.16 | 384.2 |
| 57 | 5-(5-chloropyridin-3-yl)-N-((1s,4s)-4-methylcyclohexyl)pyrimidin-2-amine | 302.12 | 303.2 |
| 58 | 4-methoxy-N-((1s,4s)-4-methylcyclohexyl)-5-(4-(trifluoromethoxy)phenyl)pyrimidin-2-amine | 381.17 | 382.2 |
| 59 | 5-(4-(difluoromethoxy)phenyl)-4-methoxy-N-((1s,4s)-4-methylcyclohexyl)pyrimidin-2-amine | 363.18 | 364.2 |
| 60 | 5-(4-tert-butoxyphenyl)-N-((1s,4s)-4-methylcyclohexyl)pyrimidin-2-amine | 339.23 | 340.2 |
| 61 | 5-(4-(5-methyl-1,3,4-oxadiazol-2-yl)phenyl)-N-((1s,4s)-4-methylcyclohexyl)pyrimidin-2-amine | 349.19 | 350.2 |
| 62 | N-cyclohexyl-5-(4-(difluoromethoxy)phenyl)-4-methoxypyrimidin-2-amine | 349.16 | 350.2 |
| 63 | N-(bicyclo[2.2.1]heptan-2-yl)-5-(4-(trifluoromethoxy)phenyl)pyrimidin-2-amine | 349.14 | 350.2 |
| 64 | 5-(4-(difluoromethoxy) phenyl)-N-((1s,4s)-4-(trifluoromethyl)cyclohexyl)pyrimidin-2-amine | 387.14 | 388.2 |
| 65 | 4-methoxy-5-(2-methyl-4-(trifluoromethoxy)phenyl)-N-((1s,4s)-4-methylcyclohexyl)pyrimidin-2-amine | 395.18 | 396.2 |
| 66 | 4-methoxy-5-(2-methoxy-4-(trifluoromethoxy)phenyl)-N-((1s,4s)-4-methylcyclohexyl)pyrimidin-2-amine | 411.18 | 412.2 |
| 67 | 5-(5-chloro-2-methoxypyridin-4-yl)-N-((1s,4s)-4-methylcyclohexyl)pyrimidin-2-amine | 332.14 | 333.2 |
| 68 | N-((1s,4s)-4-methylcyclohexyl)-5-(2-methylpyridin-4-yl)pyrimidin-2-amine | 282.18 | 283.2 |
| 69 | 4-methoxy-N-((1s,4s)-4-methylcyclohexyl)-5-(4-(piperidin-1-yl)phenyl)pyrimidin-2-amine | 380.26 | 381.2 |
| 70 | N-cyclohexyl-5-(4-(trifluoromethoxy)phenoxy)pyrimidin-2-amine | 353.14 | 354.2 |
| 71 | 5-(2-methoxy-4-(trifluoromethoxy)phenyl)-N-((1s,4s)-4-methylcyclohexyl)pyrimidin-2-amine | 381.17 | 382.2 |
| 72 | 5-(4-(difluoromethoxy) phenyl)-N-(1-methylcyclohexyl)pyrimidin-2-amine | 333.17 | 334.2 |
| 73 | 5-(6-isopropoxypyridin-3-yl)-4-methoxy-N-((1s,4s)-4-methylcyclohexyl)pyrimidin-2-amine | 356.22 | 357.2 |
| 74 | 4-methoxy-N-((1s,4s)-4-methylcyclohexyl)-5-(6-(piperidin-1-yl)pyridin-3-yl)pyrimidin-2-amine | 381.25 | 382.2 |
| 75 | N-cyclohexyl-5-(2-methoxy-4-(trifluoromethoxy)phenyl)pyrimidin-2-amine | 367.15 | 368.2 |
| 76 | N2-cyclohexyl-5-(4-(trifluoromethoxy)phenyl)pyrimidine-2,4-diamine | 352.15 | 353.2 |
| 77 | 4-methoxy-N-((1s,4s)-4-methylcyclohexyl)-5-(2-(trifluoromethyl)pyridin-4-yl)pyrimidin-2-amine | 366.17 | 367.4 |

Example 78

General Experimental Procedure

Scheme 4 illustrates a general procedure for preparing compound 1C where R is $C_3$-$C_{10}$heterocycloalkyl, $C_1$-$C_4$alkyl$C_3$-$C_{10}$heterocyclooalkyl, $C_1$-$C_4$alkylaryl or $C_1$-$C_4$alkylheteroaryl. Compound 1A can be prepared from a commercially available 2,4-dichloro-5-bromo-pyrimidine and a desired $C_3$-$C_{10}$heterocyclo alcohol or $C_3$-$C_{10}$heterocycloalkyl$C_1$-$C_4$alkyl alcohol or aryl$C_1$-$C_4$alkyl alcohol or heteroaryl$C_1$-$C_4$ alkyl alcohol using methods well-known in the art. For example, compound 1A can be prepared by treating 2,4-dichloro-5-bromo-pyrimidine in THF with a desired sodium alkoxide at about −20° C. to 25° C. for about 8-24 h. The sodium alkoxide can be generated from a corresponding alcohol and NaH in THF at about −20° C. to 60° C. for about 2-24 h or according to methods known in the art. Compound 1A can be converted to compound 1B by amination in the presence of a hindered organic base, such as triethylamine (TEA). Compound 1C can be prepared from compound 1B and a desired boronic acid or its corresponding pinacol ester through Suzuki coupling conditions.

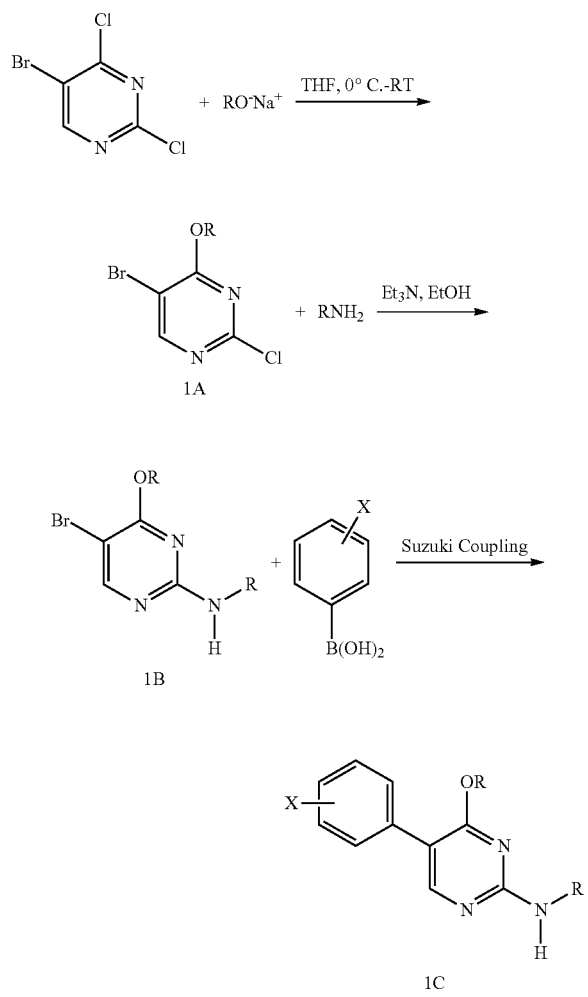

SCHEME 4

Preparation of 5-(4-Isopropoxyphenyl)-N-((1s,4S)-4-methylcyclohexyl)-4-((R)-tetrahydrofuran-3-yloxy)pyrimidin-2-amine Step 1: Preparation of (R)-5-Bromo-2-chloro-4-(tetrahydrofuran-3-yloxy)pyrimidine (1)

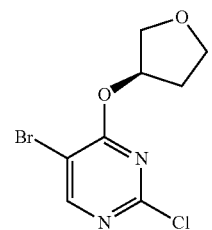

(1)

To a solution of (R)-(−)-3-hydroxytetrahydrofuran (0.9 g, 10.2 mmol) in 1.2 mL anhydrous THF at 0° C. was added NaH (60% in mineral oil, 100 mg, 2.5 mmol). The mixture was stirred at 0° C. for 5 min and then r.t. for 2 h until there was no hydrogen bubbles generated. This mixture was added slowly to a solution of 5-bromo-2,4-dichloropyrimidine (570 mg, 2.5 mmol) and (R)-(−)-3-hydroxytetrahydrofuran (0.1 g, 1.1 mmol) in 0.8 mL THF at −10° C., and then the reaction mixture was stirred at the same temperature for 30 min. The reaction was quenched with water and extracted with EtOAc. The organic layer was separated, dried ($Na_2SO_4$) and concentrated in vacuo. The residue was purified using ISCO chromatography (40 g silica gel, 1-20% EtOAc in hexanes in 40 min) to give the title compound (285 mg, 41%) as a white solid. $^1$H NMR (CDCl$_3$, 400 MHz) δ 8.45 (s, 1H), 5.69-5.66 (m, 1H), 4.11-3.91 (m, 4H), 2.36-2.21 (m, 2H).

Step 2: Preparation of 5-Bromo-N-((1s,4S)-4-methylcyclohexyl)-4-((R)-tetrahydrofuran-3-yloxy)pyrimidin-2-amine (2)

(2)

To a solution of (R)-5-bromo-2-chloro-4-(tetrahydrofuran-3-yloxy)pyrimidine (1) (285 mg, 1.02 mmol) in 2 mL EtOH was added cis-4-methylcyclohexylamine hydrochloride (242 mg, 1.6 mmol), followed by triethylamine (3 mL). The mixture was heated in a microwave reactor at 110° C. for 2 h. After cooling to room temperature, the reaction mixture was diluted with $CH_2Cl_2$, and washed with $H_2O$. The organic layer was separated, dried ($Na_2SO_4$) and concentrated in vacuo. The residue was purified by ISCO chromatography (40 g silica gel, 1-20% EtOAc in hexanes in 40 min) to give the title compound (2) (250 mg, 69%) as a white solid. $^1$H NMR (CDCl$_3$, 400 MHz) δ 8.08 (s, 1H), 5.51 (m, 1H), 5.15 (bd, 1h), 4.10-3.89 (m, 5H), 2.27-2.20 (m, 2H), 1.76 (m, 2H), 1.66-1.56 (m, 6H), 1.25-1.18 (m, 2H), 0.94 (d, 3H); MS (ESI, M+H$^+$) C$_{15}$H$_{23}$BrN$_3$O$_2$, calcd. 356.1, found 356.0, 358.0.

Step 3: Preparation of 5-(4-Isopropoxyphenyl)-N-((1s,4S)-4-methylcyclohexyl)-4-((R)-tetrahydrofuran-3-yloxy)pyrimidin-2-amine

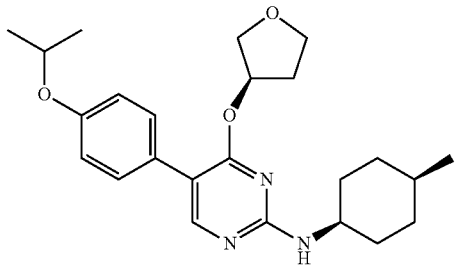 [SMILES: CC(C)Oc1ccc(-c2cnc(N[C@H]3CC[C@@H](C)CC3)nc2O[C@@H]2CCOC2)cc1]

To a solution of 5-bromo-N-((1s,4S)-4-methylcyclohexyl)-4-((R)-tetrahydrofuran-3-yloxy)pyrimidin-2-amine (2) (40.0 mg, 0.11 mmol) in CH$_3$CN (2.5 mL) was added 4-isopropoxyphenylboronic acid (40.3 mg, 0.22 mmol) followed by Pd(PPh$_3$)$_4$ (6.5 mg, 5.6 µmol) and 2 M Na$_2$CO$_3$ solution (0.75 mL). The mixture was heated in a microwave reactor at 100° C. for 30 minutes. After cooling to room temperature, the reaction mixture was diluted with EtOAc, and washed with H$_2$O. The organic layer was separated, dried (Na$_2$SO$_4$) and concentrated in vacuo. The residue was purified by ISCO chromatography (40 g silica gel, 1-25% EtOAc in hexanes in 40 min) and preparative HPLC (0-100% CH$_3$CN in H$_2$O) to give the title compound (35.5 mg, 78%) as a white solid. $^1$H NMR (CDCl$_3$, 400 MHz) 8.09 (s, 1H), 7.38 (d, 2H), 6.91 (d, 2H), 5.59 (s, 1H), 5.18 (bd, 1H), 4.60-4.55 (m, 1H), 4.12-4.07 (m, 2H), 3.94-3.88 (m, 3H), 2.25-2.18 (m, 2H), 1.82 (bd, 2H), 1.69-1.59 (m, 5H), 1.34-1.24 (m, 8H), 0.95 (d, 3H). MS (ESI, M+H$^+$) C$_{24}$H$_{34}$N$_3$O$_3$, calcd. 412.3, found 412.2.

Example 79

General Experimental Procedure

Scheme 5 illustrates a general procedure for preparing compounds 2B, 2C, 2D and 2E, where W is a bond or C$_1$-C$_4$alkyl. Compounds 2B, 2C, 2D and 2E can be prepared from compound 2A based on functional group manipulation procedures known in the art. For example, compound 2B can be prepared by treating compound 2A with a desired chloroformate in CH$_2$Cl$_2$/H$_2$O at about 0° C.-40° C. in the presence of a base such as Na$_2$CO$_3$. Compound 2C can be prepared from compound 2A with a desired acid chloride or corresponding anhydride in CH$_2$Cl$_2$ at about 0° C.-40° C. in the presence of a base such as Na$_2$CO$_3$ or TEA.

Compound 2D can be prepared by reacting compound 2A with a desired carbamoyl chloride or an isocyanate in CH$_2$Cl$_2$ at about 0° C.-40° C. in the presence of a base such as Na$_2$CO$_3$ or TEA. Compound 2E can be prepared from compound 2A with a desired sulfonyl chloride in CH$_2$Cl$_2$ at about 0° C.-40° C. in the presence of a base such as Na$_2$CO$_3$ or TEA.

Compound 2A can prepared based on the procedures described above in Example 78.

SCHEME 5

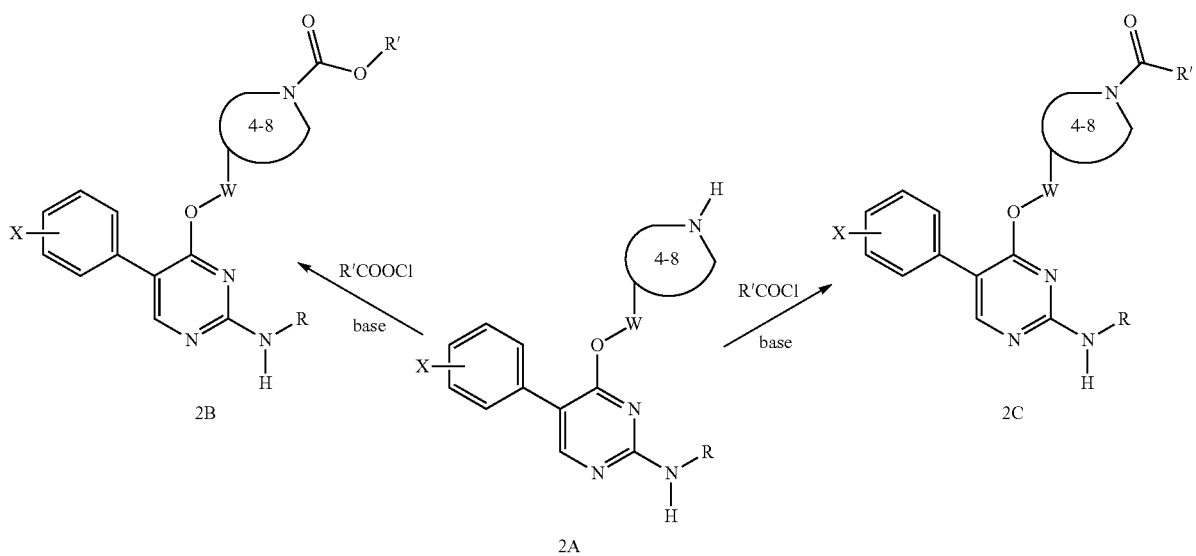

-continued

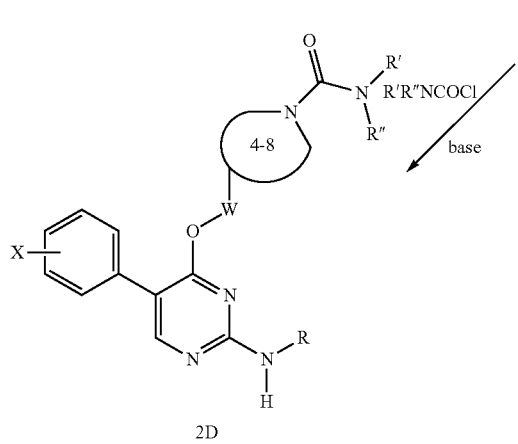

2D

W is, for example, a bond or $C_1$-$C_4$alkyl

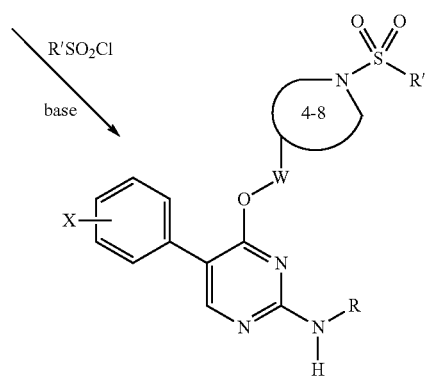

2E

Preparation of Methyl 3-(5-(2-methyl-2H-indazol-6-yl)-2-((1s,4s)-4-methylcyclohexylamino)pyrimidin-4-yloxy)pyrrolidine-1-carboxylate

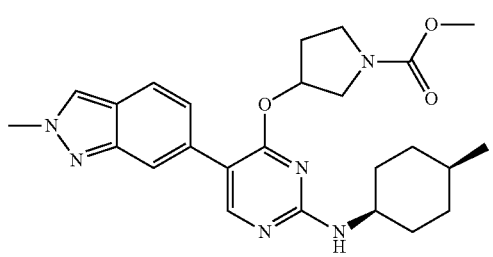

Step 1: Preparation of tert-Butyl 3-(5-bromo-2-chloropyrimidin-4-yloxy)pyrrolidine-1-carboxylate

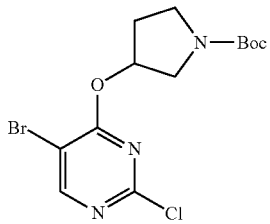 [SMILES: CC(C)(C)OC(=O)N1CCC(Oc2nc(Cl)ncc2Br)C1]

To a solution of N-Boc-3-hydroxypyrrolidine (2.06 g, 11 mmol) in anhydrous THF (50 mL), was added NaH (60% oil dispersion, 0.44 g, 11 mmol). The mixture was stirred at room temperature for 19 h. The reaction mixture was cooled to –0° C. and was added slowly to a solution of 5-bromo-2,4-dichloropyrimidine (2.28 g, 10 mmol) in anhydrous THF (20 mL) at –5° C. The resulting mixture was stirred at –0° C. for 5 h and quenched with water. The aqueous solution was extracted with ethyl acetate (3×50 mL). The combined organic layers were dried over $MgSO_4$ and concentrated in vacuo. The residue was purified on ISCO (hexane/ethyl acetate gradient, 0-20%) to give the title compound (3.0 g, 79.2%) as colorless oil. MS (ESI) m/z: Found: 378.0 ($M^+$+1); Calc. 377.0 ($M^+$)

Step 2: Preparation of tert-Butyl 3-(5-bromo-2-((1s,4s)-4-methylcyclohexylamino) pyrimidin-4-yloxy) pyrrolidine-1-carboxylate

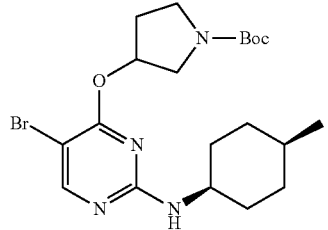 [SMILES: CC(C)(C)OC(=O)N1CCC(Oc2nc(N[C@H]3CC[C@@H](C)CC3)ncc2Br)C1]

A mixture of tert-butyl 3-(5-bromo-2-chloropyrimidin-4-yloxy)pyrrolidine-1-carboxylate (1.89 g, 5 mmol), cis-4-methylcyclohexamine hydrochloride (0.97 g, 65 mmol), triethylamine (5 mL) in ethanol (10 mL) was stirred at 85° C. for 19 h. The reaction mixture was concentrated and water (25 mL) was added. The resulting solution was extracted with ethyl acetate (3×25 mL), dried over $MgSO_4$ and concentrated. The crude product was purified on ISCO (hexane/ethyl acetate, 0-20%) to give sticky oil which was then recrystallized from ethanol to yield the title compound (1.07 g, 47.0%) as a white solid. $^1$HNMR ($CDCl_3$, 400 MHz): 8.08 (s, 1H), 5.49 (s, 1H), 5.16 (br, 1H), 3.96 (s, 1H), 3.70-3.52 (m, 4H), 2.19 (m, 2H), 1.76 (m, 2H), 1.59 (m, 5H), 1.47 (s, 9H), 1.20 (m, 2H), 0.93 (d, J=6.4 Hz, 3H). MS (ESI) m/z: Found: 455.2 ($M^+$+1); Calc. 454.2 ($M^+$).

Step 3: Preparation of tert-Butyl 3-(5-(2-methyl-2H-indazol-6-yl)-2-((1s,4s)-4-methylcyclohexylamino) pyrimidin-4-yloxy)pyrrolidine-1-carboxylate

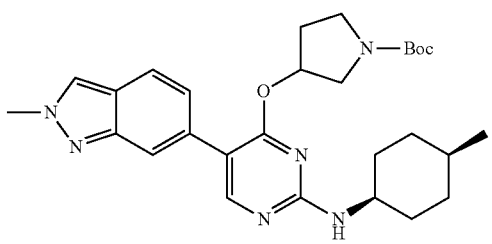

A mixture of tert-butyl 3-(5-bromo-2-((1s,4s)-4-methylcyclohexylamino)pyrimidin-4-yloxy)pyrrolidine-1-carboxylate (911 mg, 2 mmol), 2-methylindazole-6-boronic acid pinacol ester (568 mg, 2.2 mmol), Na₂CO₃ (424 mg, 4 mmol) and Pd(PPh₃)₄ (115.6 mg, 0.1 mmol) in dioxane/water (3:1, 4 mL) was stirred in a sealed tube at 140° C. for 19 h. After cooling to room temperature, water (10 mL) was added. The resulting mixture was extracted with ethyl acetate (3×25 mL). The combined organic extracts were dried over MgSO₄ and concentrated. The residue was purified on ISCO (DCM/Methanol, 0-5%, twice, then hexane/ethylacetate, 0-100%) to give the title compound as an off-white solid (430 mg, 42.5%). ¹HNMR (CDCl₃, 400 MHz): 8.20 (s, 1H), 7.87 (s, 1H), 7.71 (s, 1H), 7.61 (d, J=8.0 Hz, 1H), 7.18 (dd, J=8.8, 1.6 Hz, 1H), 5.59 (s, 1H), 5.20 (br, 1H, NH), 4.22 (s, 3H), 4.08 (s, 1H), 3.70-3.42 (m, 4H), 2.16 (m, 2H), 1.82 (m, 2H), 1.61 (m, 5H), 1.45 (s, 9H), 1.25 (m, 2H), 0.95 (d, J=7.0 Hz, 3H). MS (ESI) m/z: Found: 507.3 (M⁺+1); Calc. 506.3 (M⁺).

Step 4: Preparation of 5-(2-Methyl-2H-indazol-6-yl)-N-((1s,4s)-4-methylcyclohexyl)-4-(pyrrolidin-3-yloxy)pyrimidin-2-amine

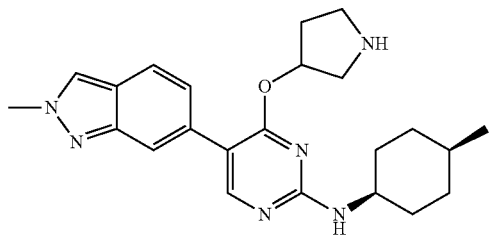

tert-Butyl 3-(5-(2-methyl-2H-indazol-6-yl)-2-((1s,4 s)-4-methylcyclohexylamino) pyrimidin-4-yloxy)pyrrolidine-1-carboxylate (430 mg, 0.849 mmol) in dichloromethane (DCM, 2 mL) was added slowly to trifluoroacetic acid (TFA, 2 mL). The resulting mixture was stirred at room temperature for 1 h and concentrated in vacuo. The residue was dissolved in DCM (5 mL) and basified with 10% Na₂CO₃ aqueous solution. The aqueous solution was extracted with DCM (3×5 mL). The combined organic extracts were dried over Na₂CO₃, and concentrated to give the title compound as an off-white solid (330 mg, 95.5%) which was used in the next step without further purification. ¹HNMR (CDCl₃, 400 MHz): 8.20 (s, 1H), 7.85 (s, 1H), 7.69 (s, 1H), 7.62 (d, J=8.8 Hz, 1H), 7.16 (dd, J=8.8, 1.6 Hz, 1H), 5.66 (m, 1H), 5.28 (br, 2H), 4.18 (s, 3H), 4.07 (s, 1H), 3.50-3.34 (m, 2H), 3.24 (m, 2H), 2.20 (m, 2H), 1.81 (m, 2H), 1.63 (m, 5H), 1.26 (m, 2H), 0.95 (d, J=6.4 Hz, 3H). MS (ESI) m/z: Found: 407.3 (M⁺+1); Calc. 406.3 (M⁺).

Step 5: Preparation of Methyl 3-(5-(2-methyl-2H-indazol-6-yl)-2-((1s,4s)-4-methylcyclohexylamino) pyrimidin-4-yloxy)pyrrolidine-1-carboxylate

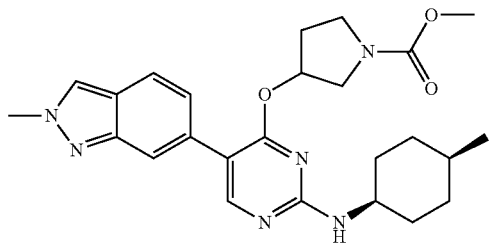

To a solution of 5-(2-Methyl-2H-indazol-6-yl)-N-((1s,4s)-4-methylcyclohexyl)-4-(pyrrolidin-3-yloxy)pyrimidin-2-amine (30 mg, 0.074 mmol) in DCM (5 mL)/water (2 mL) was added excess Na₂CO₃. To which at room temperature was added dropwise methyl chloroformate (50 µL, 0.65 mmol). The resulting solution was stirred at room temperature for 5 min. The organic layer was separated and the aqueous solution was extracted with DCM (2×5 mL). The combined organic extracts were dried over Na₂SO₄ and concentrated. The residue was purified by ISCO (DCM/Methanol, 0-10%) to give the title compound as an off-white solid (33 mg, 96.2%). ¹HNMR (CDCl₃, 400 MHz): 8.19 (s, 1H), 7.87 (s, 1H), 7.69 (s, 1H), 7.61 (d, J=8.8 Hz, 1H), 7.16 (d, J=8.8 Hz, 1H), 5.63 (m, 1H), 5.21 (s, 1H), 4.22 (s, 3H), 4.09 (m, 1H), 3.76-3.46 (m, 4H), 3.69 (s, 3H), 2.17 (m, 2H), 1.82 (m, 2H), 1.65 (m, 5H), 1.26 (m, 2H), 0.95 (d, J=7.0 Hz, 3H). MS (ESI) m/z: Found: 465.3 (M⁺+1); Calc. 464.3 (M⁺).

Example 80

Preparation of Methyl 3-(2-((1s,4s)-4-methylcyclohexylamino)-5-(2,3,4a,8a-tetrahydrobenzo[b][1,4]dioxin-6-yl)pyrimidin-4-yloxy)pyrrolidine-1-carboxylate

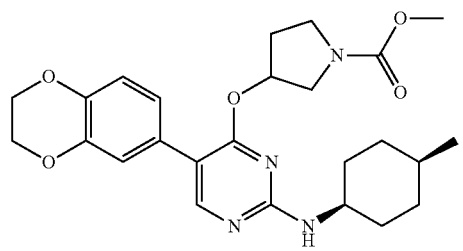 [SMILES: COC(=O)N1CCC(Oc2nc(N[C@H]3CC[C@@H](C)CC3)ncc2-c2ccc3c(c2)OCCO3)C1]

Step 1: Preparation of tert-Butyl 3-(5-(2,3-dihydrobenzo[b][1,4]dioxin-6-yl)-2-((1s,4s)-4-methylcyclohexylamino)pyrimidin-4-yloxy)pyrrolidine-1-carboxylate

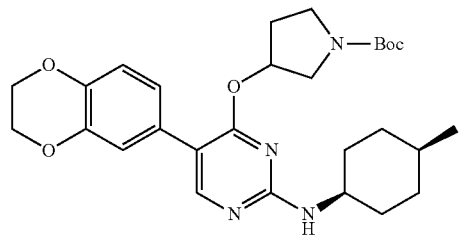 [SMILES: CC(C)(C)OC(=O)N1CCC(Oc2nc(N[C@H]3CC[C@@H](C)CC3)ncc2-c2ccc3c(c2)OCCO3)C1]

Using the procedure of Example 79, Step 3, tert-butyl 3-(5-bromo-2-((1s,4s)-4-methylcyclohexylamino)pyrimidin-4-yloxy)pyrrolidine-1-carboxylate was reacted with 2,3-dihydrobenzo[b][1,4]dioxin-6-ylboronic acid to provide the title compound. ¹HNMR (CDCl₃, 400 MHz): 8.08 (d, 1H, CH), 6.96 (s, 1H), 6.92 (d, 1H), 6.86 (d, 1H), 5.57 (m, 1H), 5.19 (br, 1H), 4.27 (s, 4H), 4.05 (m, 1H), 3.70-3.45 (m, 4H), 2.16 (m, 2H), 1.81 (m, 2H), 1.70-1.57 (m, 5H), 1.45 (ds, 9H), 1.25 (m, 2H), 0.94 (d, 3H).

Step 2: Preparation of 5-(2,3-Dihydrobenzo[b][1,4]
dioxin-6-yl)-N-((1s,4s)-4-methylcyclohexyl)-4-(pyr-
rolidin-3-yloxy)pyrimidin-2-amine

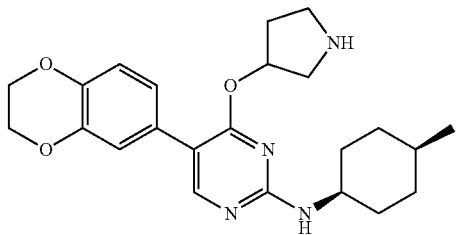 [SMILES: C[C@H]1CC[C@@H](Nc2ncc(-c3ccc4c(c3)OCCO4)c(OC3CCNC3)n2)CC1]

Using the procedure of Example 79, Step 4, tert-butyl 3-(5-(2,3-dihydrobenzo[b][1,4]dioxin-6-yl)-2-((1s,4s)-4-methylcyclohexylamino)pyrimidin-4-yloxy)pyrrolidine-1-carboxylate was reacted with TFA to provide the title compound. $^1$HNMR (CDCl$_3$, 400 MHz): 8.08 (s, 1H, CH), 6.96-6.85 (m, 3H), 5.73 (m, 1H), 5.19 (br, 1H), 4.27 (s, 4H), 4.05 (m, 1H), 3.24 (m, 3H), 3.07 (m, 1H), 2.45 (br, 1H), 2.17 (m, 1H), 2.07 (m, 1H), 1.80 (m, 2H), 1.70-1.57 (m, 5H), 1.25 (m, 2H), 0.94 (d, 3H). MS (ESI) m/z: Found: 411.3 (M$^+$+1); Calc. 410.2 M$^+$).

Step 3: Preparation of Methyl 3-(2-((1s,4s)-4-methylcyclohexylamino)-5-(2,3,4a,8a-tetrahydrobenzo[b][1,4]dioxin-6-yl)pyrimidin-4-yloxy)pyrrolidine-1-carboxylate

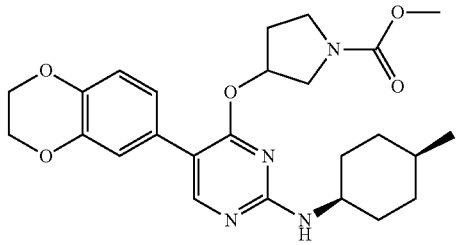 [SMILES: COC(=O)N1CCC(Oc2nc(N[C@H]3CC[C@@H](C)CC3)ncc2-c2ccc3c(c2)OCCO3)C1]

Using the procedure of Example 79, Step 5, N-((1s,4s)-4-methylcyclohexyl)-4-(pyrrolidin-3-yloxy)-5-(2,3,4a,8a-tetrahydrobenzo[b][1,4]dioxin-6-yl)pyrimidin-2-amine was reacted with methyl chloroformate to provide the title compound. $^1$HNMR (CDCl$_3$, 400 MHz): 8.07 (s, 1H), 6.95-6.84 (m, 3H), 5.61 (m, 1H), 5.18 (s, 1H), 4.27 (s, 4H), 4.05 (m, 1H), 3.74-3.48 (m, 7H), 2.18 (m, 2H), 1.80 (m, 2H), 1.62 (m, 5H), 1.26 (m, 2H), 0.94 (d, 3H). MS (ESI) m/z: Found: 469.3 (M$^+$+1); Calc. 468.2 (M$^+$).

Example 81

Preparation of 5-(2,3-Dihydrobenzo[b][1,4]dioxin-6-yl)-N-((1s,4s)-4-methylcyclohexyl)-4-(1-(methylsulfonyl)pyrrolidin-3-yloxy)pyrimidin-2-amine

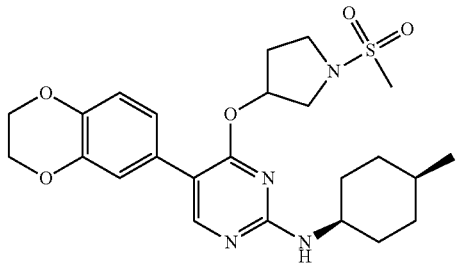 [SMILES: CS(=O)(=O)N1CCC(Oc2nc(N[C@H]3CC[C@@H](C)CC3)ncc2-c2ccc3c(c2)OCCO3)C1]

To a mixture of 5-(2,3-dihydrobenzo[b][1,4]dioxin-6-yl)-N-((1s,4s)-4-methylcyclohexyl)-4-(pyrrolidin-3-yloxy)pyrimidin-2-amine (41.3 mg, 0.1 mmol), and saturated Na$_2$CO$_3$ solution in CH$_2$Cl$_2$ (5 mL) at room temperature was added dropwise methyl sulfonylchloride (50 µL, 0.65 mmol). After stirring at room temperature for 5 min, the organic layer was separated. The aqueous solution was extracted with CH$_2$Cl$_2$ (2×5 mL). The combined organic extracts were dried over Na$_2$SO$_4$ and concentrated. The residue was purified by ISCO (DCM/Methanol, 0-10%) to give the title compound as a white solid (38.5 mg, 79%). $^1$HNMR (CDCl$_3$, 400 MHz): 8.07 (s, 1H), 6.91 (s, 1H), 6.85 (s, 2H), 5.68 (m, 1H), 5.20 (br, 1H), 4.27 (s, 4H), 4.05 (m, 1H), 3.69 (dd, 1H), 3.58 (m, 1H), 3.51 (m, 1H), 3.31 (m, 1H), 2.57 (s, 3H), 2.32 (m, 1H), 2.23 (m, 1H), 1.81 (m, 2H), 1.63 (m, 5H), 1.25 (m, 2H), 0.94 (d, 3H). MS (ESI) m/z: Found: 489.3 (M$^+$+1); Calc. 488.2 (M$^+$).

Example 82

General Experimental Procedure

Scheme 6 illustrates a general procedure for preparing compound 3C. Compound 3A can be prepared from a commercially available 2,4-dichloro-5-bromo-pyrimidine and a desired aryl alcohol or heteroaryl alcohol using methods well-known in the art. For example, compound 3A can be prepared by treating 2,4-dichloro-5-bromo-pyrimidine with a desired aryl alcohol or heteroaryl alcohol in DMF at about −20° C. to 0° C. for about 6-24 h. Compound 3B can be prepared from compound 3A by amination according to methods well-known in the art. Compound 3C can be prepared from compound 3B and a desired boronic acid or its corresponding pinacol ester through Suzuki coupling conditions.

SCHEME 6

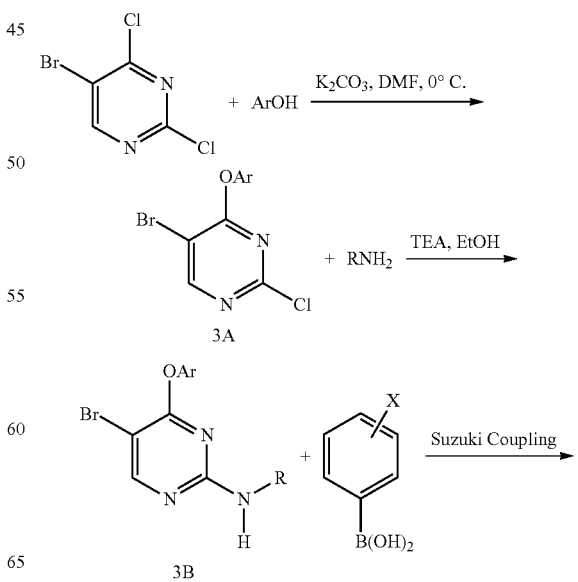

53

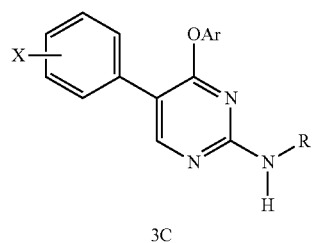

3C

Preparation of 5-(4-Isopropoxyphenyl)-4-(3-methoxyphenoxy)-N-((1s,4s)-4-methylcyclohexyl)pyrimidin-2-amine

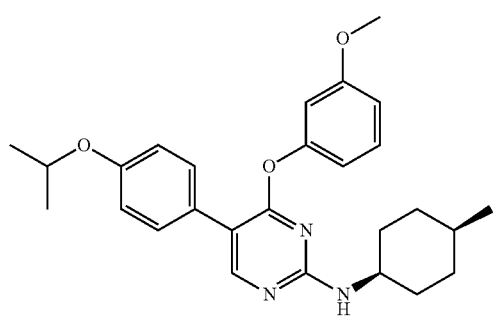 [SMILES: COc1cccc(Oc2nc(N[C@H]3CC[C@@H](C)CC3)ncc2-c2ccc(OC(C)C)cc2)c1]

Step 1: Preparation of 5-Bromo-2-chloro-4-(3-methoxyphenoxy)pyrimidine

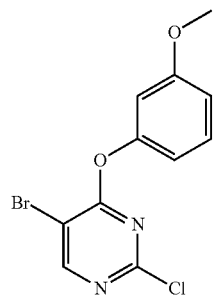 [SMILES: COc1cccc(Oc2nc(Cl)ncc2Br)c1]

To a mixture of 5-bromo-2,4-dichloropyrimidine (300 mg, 1.32 mmol) and 3-methoxyphenol (163.4 mg, 1.32 mmol) in DMF (5 mL) at 0° C. was added $K_2CO_3$ (363 mg, 2.63 mmol). The resulting mixture was stirred at 0° C. for 7 h. The reaction was quenched with $H_2O$ and extracted with EtOAc (3×30 mL). The combined organic extracts were washed with $H_2O$ (5×30 mL), brine, dried and concentrated. The crude product was purified by preparative TLC using 100% of $CH_2Cl_2$ as eluting solvent to afford the title compound (380 mg, 92%). $^1$HNMR (CDCl$_3$, 400 MHz): 8.57 (s, 1H), 7.37 (dd, 1H), 6.88-6.84 (dd, 1H), 6.72-6.79 (dd+d, 2H), 3.83 (s, 3H). MS (ESI) m/z: Found: 315.0 ($M^++1$), 317.0 ($M^++3$); Calc. 314.0 ($M^+$).

54

Step 2: Preparation of 5-Bromo-4-(3-methoxyphenoxy)-N-((1s,4s)-4-methylcyclohexyl)pyrimidin-2-amine

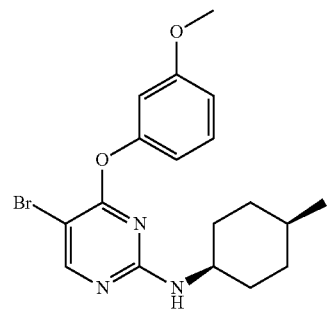 [SMILES: COc1cccc(Oc2nc(N[C@H]3CC[C@@H](C)CC3)ncc2Br)c1]

Using the procedure of Example 78, Step 2, 5-bromo-2-chloro-4-(3-methoxyphenoxy)pyrimidine was reacted with cis-4-methylcyclohexylamine hydrochloride to provide the title compound. MS (ESI) m/z: Found: 392.1 ($M^++1$), 394.1 ($M^++3$); Calc. 391.1 ($M^+$).

Step 3: Preparation of 5-(4-Isopropoxyphenyl)-4-(3-methoxyphenoxy)-N-((1s,4s)-4-methylcyclohexyl)pyrimidin-2-amine

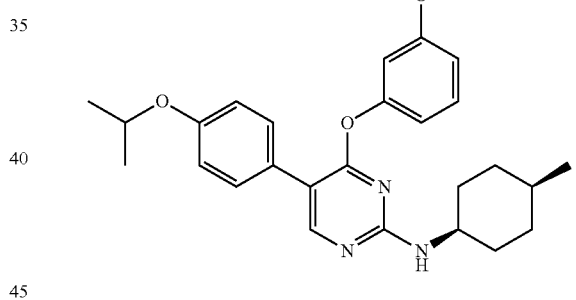

Using the procedure of Example 78, Step 3, 5-bromo-4-(3-methoxyphenoxy)-N-((1s,4s)-4-methylcyclohexyl)pyrimidin-2-amine was reacted with 4-isopropoxyphenylboronic acid to provide the title compound. $^1$H NMR (CDCl$_3$, 400 MHz) 8.24 (s, 1H), 7.50-7.52 (m, 2H), 7.28 (m, 1H), 6.97-6.94 (m, 2H), 6.79-6.73 (m, 3H), 5.15 (br s, 1H), 4.61-4.57 (m, 1H), 3.82 (s, 3H), 1.68-1.51 (m, 7H), 1.39 (s, 3H), 1.37 (s, 3H), 1.21-1.18 (m, 3H), 0.92 (d, 3H). MS (ESI) m/z: Found: 448.2 ($M^++1$), Calc. 447.25 ($M^+$).

Example 83

Preparation of 4-(((R)-1,4-Dioxan-2-yl)methoxy)-5-(2,3-dihydrobenzo[b][1,4]dioxin-6-yl)-N-((1s,4S)-4-methylcyclohexyl)pyrimidin-2-amine Scheme 7 below illustrates the overall synthetic process for making the title compound. Additional details for particular steps in the sequence are provided below.

SCHEME 7

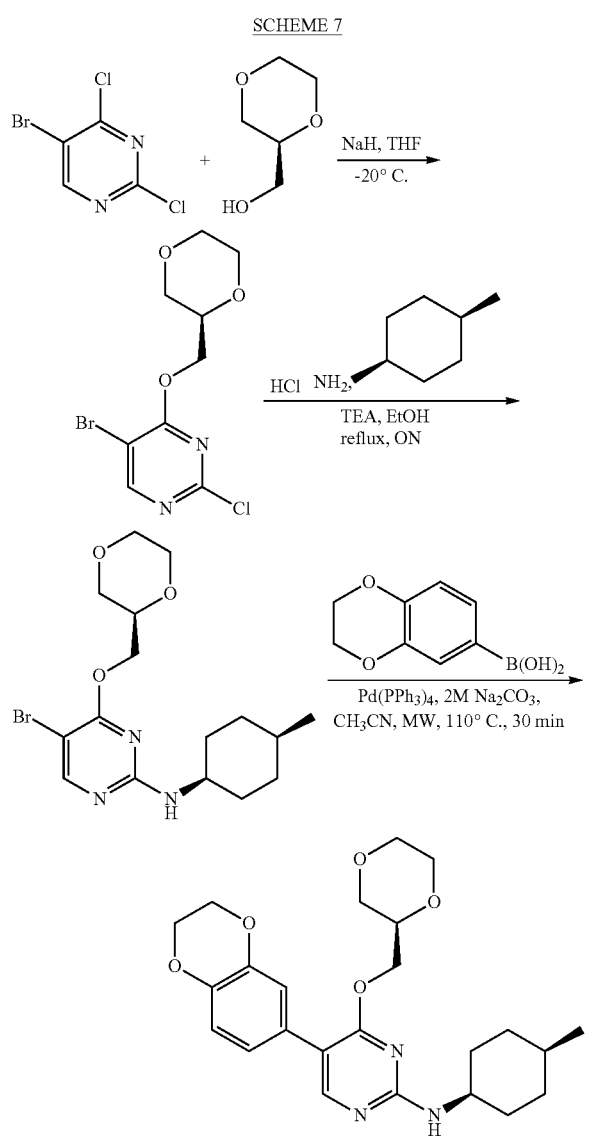

Step 1: Preparation of Starting Material
(S)-(1,4-Dioxan-2-yl)methanol

Scheme 8 below illustrates the procedure for making the title compound from (R)-2-(chloromethyl)oxirane. Additional details on the synthetic procedure can be found, for example, in H. Y. Kim, R. J. Kuhn, C. Patkar, R. Warrior, M. Cushman, Bioorg. Med. Chem. 15 (2007), 2667-2679.

SCHEME 8

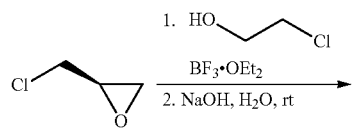

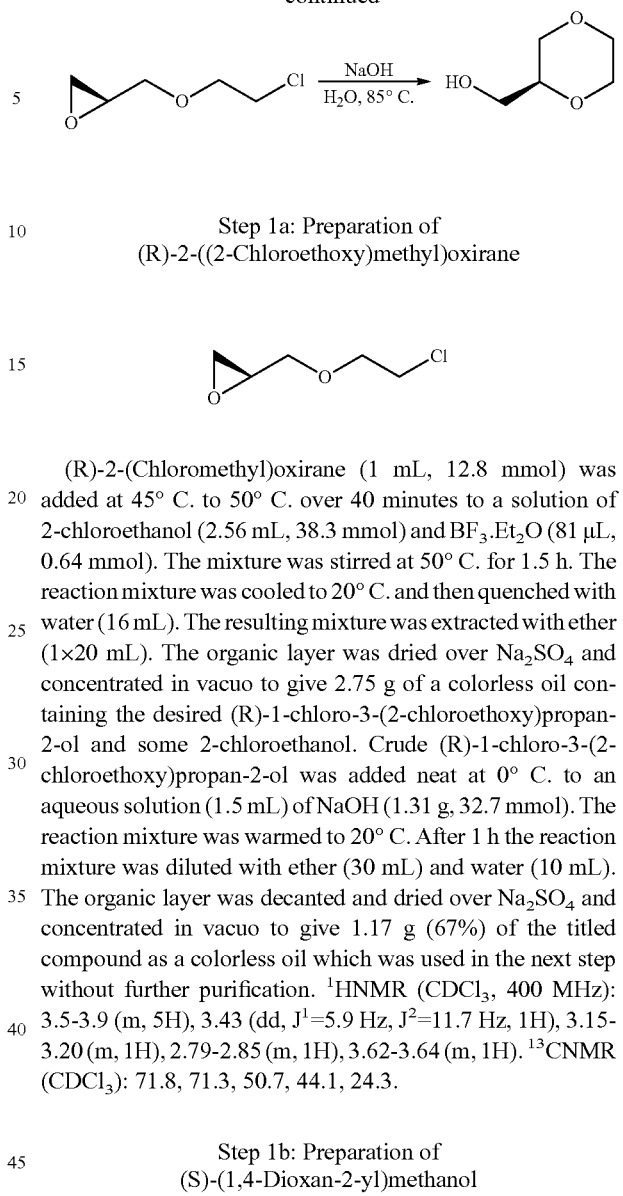

Step 1a: Preparation of
(R)-2-((2-Chloroethoxy)methyl)oxirane (R)-2-(Chloromethyl)oxirane (1 mL, 12.8 mmol) was added at 45° C. to 50° C. over 40 minutes to a solution of 2-chloroethanol (2.56 mL, 38.3 mmol) and $BF_3 \cdot Et_2O$ (81 µL, 0.64 mmol). The mixture was stirred at 50° C. for 1.5 h. The reaction mixture was cooled to 20° C. and then quenched with water (16 mL). The resulting mixture was extracted with ether (1×20 mL). The organic layer was dried over $Na_2SO_4$ and concentrated in vacuo to give 2.75 g of a colorless oil containing the desired (R)-1-chloro-3-(2-chloroethoxy)propan-2-ol and some 2-chloroethanol. Crude (R)-1-chloro-3-(2-chloroethoxy)propan-2-ol was added neat at 0° C. to an aqueous solution (1.5 mL) of NaOH (1.31 g, 32.7 mmol). The reaction mixture was warmed to 20° C. After 1 h the reaction mixture was diluted with ether (30 mL) and water (10 mL). The organic layer was decanted and dried over $Na_2SO_4$ and concentrated in vacuo to give 1.17 g (67%) of the titled compound as a colorless oil which was used in the next step without further purification. $^1$HNMR (CDCl$_3$, 400 MHz): 3.5-3.9 (m, 5H), 3.43 (dd, $J^1$=5.9 Hz, $J^2$=11.7 Hz, 1H), 3.15-3.20 (m, 1H), 2.79-2.85 (m, 1H), 3.62-3.64 (m, 1H). $^{13}$CNMR (CDCl$_3$): 71.8, 71.3, 50.7, 44.1, 24.3.

Step 1b: Preparation of
(S)-(1,4-Dioxan-2-yl)methanol

An aqueous solution (9 mL) of NaOH (0.86 g, 21.4 mmol) was added to (R)-2-((2-chloroethoxy)methyl)oxirane neat (1.17 g, 8.6 mmol) at room temperature. The reaction mixture was stirred at 85° C. for 2.5 h. The reaction mixture was cooled to 20° C. and the aqueous layer was first extracted with $CH_2Cl_2$ (5×25 mL) and the combined layers were dried over $Na_2SO_4$ and concentrated to give 1.68 g of crude titled product. A second round of extractions with $CH_2Cl_2$ (5×25 mL) gave 185 mg of pure title compound (18%) as a colorless oil. $^1$HNMR (CDCl$_3$, 400 MHz): 3.6-3.9 (m, 9H), 2.45 (m, 1H). $^{13}$CNMR (CDCl$_3$): 75.6, 67.8, 66.5, 66.3, 62.4.

Step 2: Preparation of (R)-4-((1,4-Dioxan-2-yl)methoxy)-5-bromo-2-chloropyrimidine

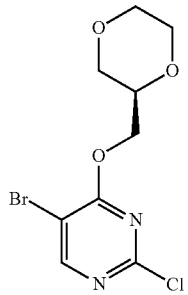 [SMILES: Clc1ncc(Br)c(OC[C@H]2COCCO2)n1]

To a solution of (S)-(1,4-dioxan-2-yl)methanol (185 mg, 1.6 mmol) in anhydrous THF (2 mL), was added NaH (60% oil dispersion, 42 mg, 1.04 mmol). The mixture was stirred at room temperature for 2.5 h. The reaction mixture was cooled to −20° C. and 5-bromo-2,4-dichloropyrimidine (252 mg, 1.04 mmol) was added at once. The resulting mixture was stirred between −15° C. and 15° C. for 6 h and quenched with water. The aqueous solution was extracted with ethyl acetate (3×10 mL). The combined organic layers were dried over $Na_2SO_4$ and concentrated in vacuo. The residue was purified on ISCO (hexane/ethyl acetate gradient, 5-20%) to give the title compound (57 mg, 17.7%) as colorless oil. $^1$HNMR ($CDCl_3$, 400 MHz): 8.44 (s, 1H), 4.47 (dd, $J^1$=5.5 Hz, $J^2$=11.7 Hz, 1H), 4.43 (dd, $J^1$=4.5 Hz, $J^2$=11.7 Hz, 1H), 3.98-4.04 (m, 1H), 3.72-3.91 (m, 4H), 3.61-3.69 (m, 1H), 3.55 (dd, $J^1$=10.0 Hz, $J^2$=11.5 Hz, 1H). MS (ESI) m/z: Found: 309.0 ($M^1$+1); Calc. 308.0 ($M^+$)

Step 3: Preparation of 4-(((R)-1,4-Dioxan-2-yl)methoxy)-5-bromo-N-((1s,4S)-4-methylcyclohexyl)pyrimidin-2-amine

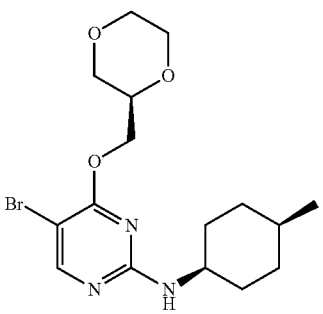 [SMILES: C[C@H]1CC[C@@H](Nc2ncc(Br)c(OC[C@H]3COCCO3)n2)CC1]

A mixture of (R)-4-((1,4-dioxan-2-yl)methoxy)-5-bromo-2-chloropyrimidine (57 mg, 0.18 mmol), cis-4-methylcyclohexamine hydrochloride (30 mg, 0.20 mmol), triethylamine (0.5 mL) in ethanol (1 mL) was stirred at 100° C. for 19 h. The reaction mixture was concentrated and saturated $NaHCO_3$ (3 mL) was added. The resulting solution was extracted with $CH_2Cl_2$ (3×5 mL), dried over $Na_2SO_4$ and concentrated. The crude product was purified on ISCO (hexane/ethyl acetate, 5-15%) to give the title compound (64 mg, 90.0%) as a colorless oil.

$^1$HNMR ($CDCl_3$, 400 MHz): 8.44 (s, 1H), 5.19 (br s, 1H), 4.36 (dd, $J^1$=5.1 Hz, $J^2$=11.3 Hz, 1H), 4.27 (dd, $J^1$=5.4 Hz, $J^2$=11.3 Hz, 1H), 3.61-4.13 (m, 7H), 3.52 (t, J=10.3 Hz, 1H), 1.68-1.82 (m, 2H), 1.46-1.68 (m, 5H), 1.10-1.28 (m, 2H), 0.92 (d, J=6.3 Hz, 3H). MS (ESI) m/z: Found: 386.0 ($M^+$+1), 388.0 ($M^+$+3), Calc. 385.1 ($M^+$).

Step 4: Preparation of 4-(((R)-1,4-Dioxan-2-yl)methoxy)-5-(2,3-dihydrobenzo[b][1,4]dioxin-6-yl)-N-((1s,4S)-4-methylcyclohexyl)pyrimidin-2-amine

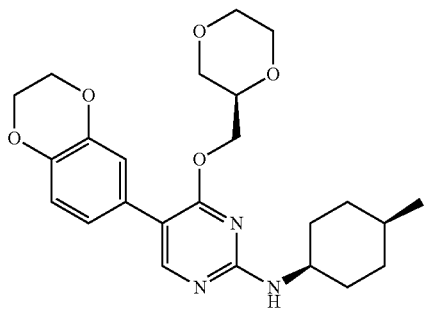 [SMILES: C[C@H]1CC[C@@H](Nc2ncc(-c3ccc4c(c3)OCCO4)c(OC[C@H]3COCCO3)n2)CC1]

Using the procedure of Example 78, Step 3,4-(((R)-1,4-dioxan-2-yl)methoxy)-5-bromo-N-((1s,4S)-4-methylcyclohexyl)pyrimidin-2-amine was reacted with 2,3-dihydrobenzo[b][1,4]dioxin-6-ylboronic acid to provide the title compound (66% yield). $^1$H NMR ($CDCl_3$, 400 MHz) 8.02 (s, 1H), 7.00 (d, J=2.0 Hz, 1H), 6.93 (dd, $J^1$=2.0 Hz, $J^2$=8.6 Hz, 1H), 6.87 (d, J=8.6 Hz, 1H), 5.17 (br s, 1H), 4.38 (dd, $J^1$=5.5 Hz, $J^2$=11.7 Hz, 1H), 4.32 (dd, $J^1$=5.5 Hz, $J^2$=11.7 Hz, 1H), 4.28 (s, 4H), 4.04-4.12 (m, 1H), 3.94-4.01 (m, 1H), 3.60-3.89 (m, 5H), 3.46-3.52 (m, 1H), 1.76-1.87 (m, 2H), 1.46-1.76 (m, 5H), 1.18-1.32 (m, 2H), 0.92 (d, J=6.3 Hz, 3H). MS (ESI) m/z: Found: 442.2 ($M^+$+1), Calc. 441.2 ($M^+$).

Example 84

Preparation of 4-((R)-Tetrahydrofuran-3-yloxy)-5-(2,3-dihydrobenzo[b][1,4]dioxin-6-yl)-N-(2,6-dimethylcyclohexyl)pyrimidin-2-amine

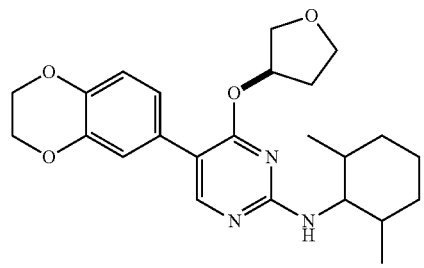 [SMILES: CC1CCCC(C)C1Nc1ncc(-c2ccc3c(c2)OCCO3)c(O[C@@H]2CCOC2)n1]

Step 1: Preparation of 4-((R)-Tetrahydrofuran-3-yloxy)-5-bromo-N-(2,6-dimethylcyclohexyl)pyrimidin-2-amine

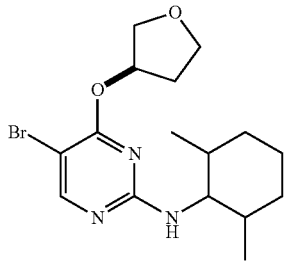 [SMILES: CC1CCCC(C)C1Nc1ncc(Br)c(O[C@@H]2CCOC2)n1]

Using the procedure of Example 78, Step 2, (R)-5-bromo-2-chloro-4-(tetrahydrofuran-3-yloxy)pyrimidine was reacted with 2,6-dimethylcyclohexanamine HCl salt to provide the title compound. MS (ESI) m/z: Found: 370 (M$^+$+1), Calc. 369 (M$^+$).

Step 2: Preparation of 4-((R)-Tetrahydrofuran-3-yloxy)-5-(2,3-dihydrobenzo[b][1,4]dioxin-6-yl)-N-(2,6-dimethylcyclohexyl)pyrimidin-2-amine

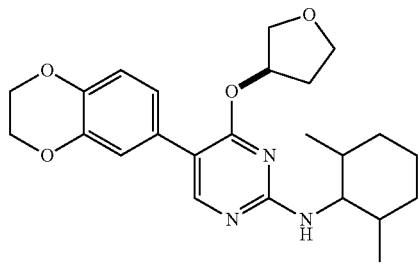 [SMILES: CC1CCCC(C)C1Nc1ncc(-c2ccc3c(c2)OCCO3)c(O[C@@H]2CCOC2)n1]

Using the procedure of Example 78, Step 3, 4-((R)-tetrahydrofuran-3-yloxy)-5-bromo-N-(2,6-dimethylcyclohexyl)pyrimidin-2-amine was reacted with 2,3-dihydrobenzo[b][1,4]dioxin-6-yl-6-boronic acid to provide the title compound. $^1$H NMR (CDCl$_3$, 300 MHz) δ 0.89 (two d, J=6.9 Hz, 6H), 1.0~2.2 (set of m, 10H), 3.9~4.1 (set of m, 4H), 4.22 (s, overlapped 4H+1H), 5.07 (br, 1H), 5.58 (s, 1H) 6.85~7.0 (set of m, 3H, aromatic CH), 8.03 (s, 1H). MS (ESI) m/z: Found: 426 (M$^+$+1), Calc. 425 (M$^+$).

Example 85

Preparation of 4-(4-((R)-Tetrahydrofuran-3-yloxy)-5-(2,3-dihydrobenzo[b][1,4]dioxin-6-yl)pyrimidin-2-ylamino)-1-methylcyclohexanol

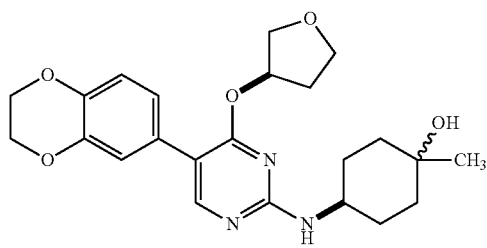

Step 1: Preparation of Starting Material 4-Amino-1-methylcyclohexanol Hydrochloride

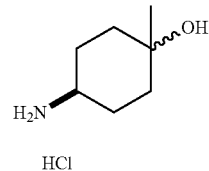

General Synthetic Procedure:

The compound 4-amino-1-methylcyclohexanol hydrochloride can be prepared in two steps from tert-butyl 4-oxocyclohexylcarbamate as shown in Scheme 9 below.

SCHEME 9

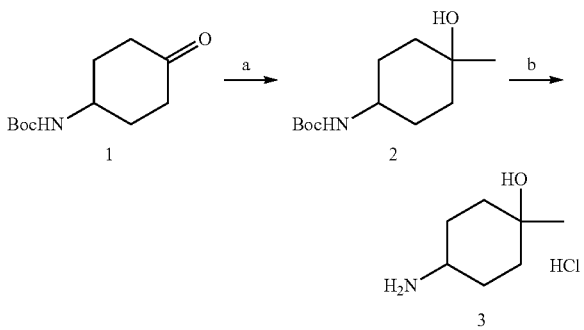

Reagents and Conditions: a) MeMgBr. b) 4M HCl

To a stirred solution of tert-butyl 4-oxocyclohexylcarbamate (2 g, 9.3 mmol) in THF (40 mL) at −78° C. was added dropwise MeMgBr (10 mL of 3M/THF, 30 mmol). The reaction mixture was allowed to warm to room temperature. After stirring at room temperature for 18 h, the reaction was treated with saturated NH$_4$Cl aqueous solution. The solution was concentrated, taken up into CH$_2$Cl$_2$, washed with H$_2$O by aid of citric acid. The organic phase was washed with saturated NaHCO$_3$ aqueous solution, H$_2$O, brine, dried (Na$_2$SO$_4$) and concentrated. The crude product was purified by column chromatography to give tert-butyl 4-hydroxy-4-methylcyclohexylcarbamate 2 as oil (1.2 g, 56%). $^1$H NMR (300 MHz, CDCl$_3$) δ 1.20 (s, 3H), 1.45 (s, overlapped 9H), 1.5~1.8 (set of m, 10H), 3.40 (br, 1H), 4.40 (br, 1H).

tert-Butyl 4-hydroxy-4-methylcyclohexylcarbamate 2 (1.2 g, 5.2 mmol) in EtOAc (20 mL) at room temperature was treated with 4M HCl (10 mL of dioxane). After stirring at room temperature for 1 h, the solid was collected by filtration, washed with EtOAc and hexane, and dried to provide the title compound 3 (900 mg). MS (ESI) m/z: Found: 130 (M$^+$+1), Calc. 129 (M$^+$).

Step 2: Preparation of 4-(4-((R)-Tetrahydrofuran-3-yloxy)-5-bromopyrimidin-2-ylamino)-1-methylcyclohexanol

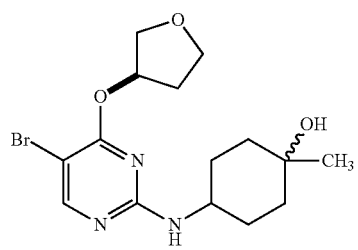

Using the procedure of Example 78, Step 2, (R)-5-bromo-2-chloro-4-(tetrahydrofuran-3-yloxy)pyrimidine was reacted with 4-amino-1-methylcyclohexanol HCl salt to provide the title compound. MS (ESI) m/z: Found: 372 (M⁺+1), Calc. 371 (M⁺).

Step 3: Preparation of 4-(4-((R)-Tetrahydrofuran-3-yloxy)-5-(2,3-dihydrobenzo[b][1,4]dioxin-6-yl)pyrimidin-2-ylamino)-1-methylcyclohexanol

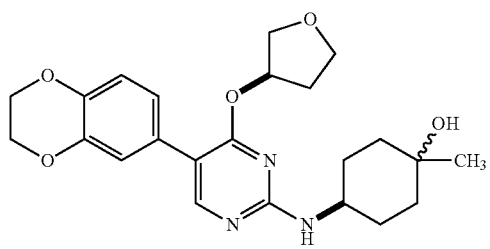

Using the procedure of Example 78, Step 3,4-(4-((R)-tetrahydrofuran-3-yloxy)-5-bromopyrimidin-2-ylamino)-1-methylcyclohexanol was reacted with 2,3-dihydrobenzo[b][1,4]dioxin-6-yl-6-boronic acid to provide the title compound. $^1$H NMR (CDCl$_3$, 300 MHz) δ 1.27 (two s, overlapped 3H), 1.2-2.2 (set of m, 10H), 3.76 (br, 1H), 3.92~4.1 (set of m, 4H), 4.28 (s, 4H), 5.94 (br, 1H), 5.55 (s, 1H), 6.85~7.0 (set of m, 3H, aromatic CH), 8.06 (s, 1H). MS (ESI) m/z: Found: 428.2 (M⁺+1), Calc. 427.2 (M⁺).

Example 86

Preparation of 4-((R)-Tetrahydrofuran-3-yloxy)-5-(2,3-dihydrobenzo[b][1,4]dioxin-6-yl)-N-((1s,4S)-4-methoxycyclohexyl)pyrimidin-2-amine

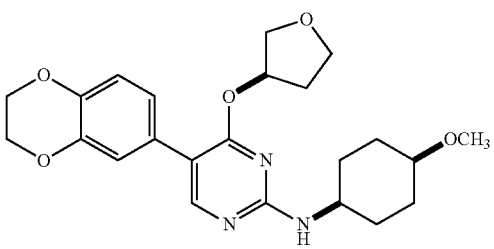

Step 1: Preparation of Starting Material 4-Methoxycyclohexanamine Hydrochloride

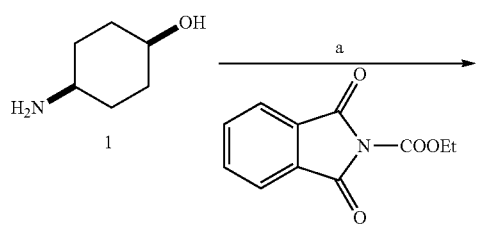

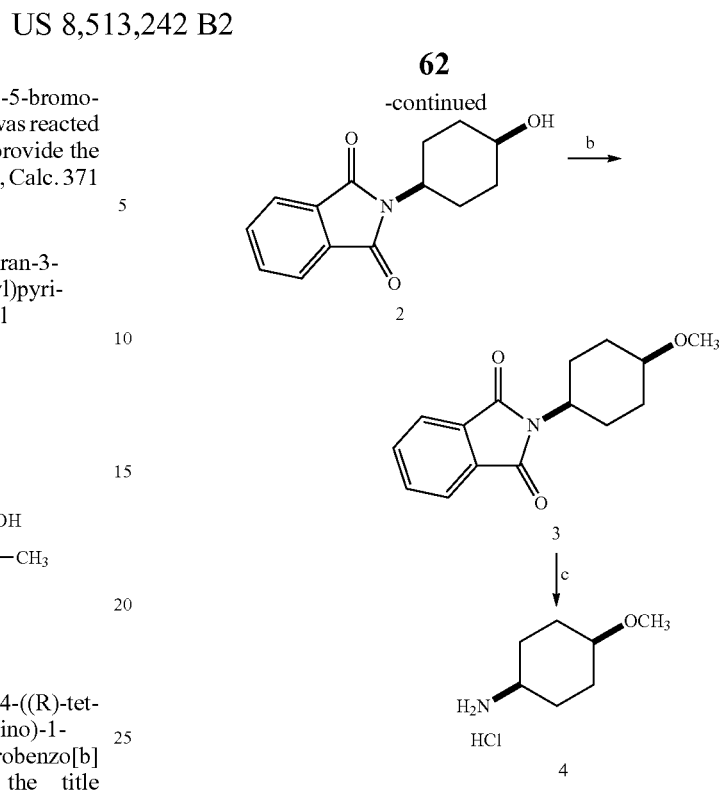

Reagents and Conditions: a) K$_2$CO$_3$, H$_2$;
b) KHMDS, MeI, and THF;
c) NH$_2$NH$_2$, EtOH, then 4M HCl Step 1-1: Preparation of 2-((1s,4s)-4-Hydroxycyclohexyl)isoindoline-1,3-dione (2)

To a stirred solution of cis-4-aminocyclohexanol HCl (107 mg, 0.71 mmol) in H$_2$O (1.7 mL) at room temperature was added K$_2$CO$_3$ (174 mg, 1.25 mmol), followed by N-carboethoxyphthalimide (174 mg, 0.79 mmol). After stirring at room temperature for 30 min, the solid was filtered, washed with H$_2$O, and dried in vacuo to provide the title compound (140 mg, 81%) as a white solid. $^1$H NMR (300 MHz, CDCl$_3$) δ 7.82 (m, 1H), 7.79 (m, 1H), 4.10 (m, 1H), 2.64 (m, 1H), 1.5~2.0 (set of m, 4H). MS (ESI) m/z: Found: 491 (2M⁺+1), Calc. 245 (M⁺).

Step 1-2: Preparation of 2-((1s,4s)-4-Methoxycyclohexyl)isoindoline-1,3-dione (3)

To a stirred solution of 2-((1s,4s)-4-hydroxycyclohexyl)isoindoline-1,3-dione 2 (125 mg, 0.51 mmol) in THF (4 mL) at −78° C. was added KHMDS (1.22 mL of 0.5M/THF, 0.61 mmol). After stirring at the same temp for 15 min, to the solution was added iodomethane (87 mg, 0.62 mmol). The reaction mixture was allowed to warm to room temperature. After stirring at room temperature for 2 h, saturated NH$_4$Cl aqueous solution was added. The solution was extracted with EtOAc (3×). The combined extracts were washed with water, brine, dried (Na$_2$SO$_4$), and concentrated to provide the title compound (120 mg, 91%). $^1$H NMR (300 MHz, CDCl$_3$) δ 7.81 (m, 2H), 7.65 (m, 2H), 4.19 (m, 1H), 3.45 (m, 1H), 3.25 (s, 3H), 2.59 (m, 2H), 2.15 (m, 2H), 1.45 (m, 4H). MS (ESI) m/z: Found: 260 (M⁺+1), Calc. 259 (M⁺).

Step 1-3: Preparation of 4-Methoxycyclohexanamine hydrochloride (4)

To a stirred solution of 2-((1s,4s)-4-methoxycyclohexyl)isoindoline-1,3-dione 3 (110 mg, 0.43 mmol) in EtOH (3 mL)

at room temperature was added NH$_2$NH$_2$ hydrate (106 mg, 2.3 mmol). After heating at 50° C. for 2 h, the reaction was quenched with H$_2$O, extracted with dichloromethane (3×). The combined extracts were treated with 4M HCl and the solid was collected after filtering. The solid was washed with dichloromethane/hexane and dried in vacuo to give the title compound 4. MS (ESI) m/z: Found: 130 (M$^+$+1), Calc. 129 (M$^+$).

Step 2: Preparation of 4-((R)-Tetrahydrofuran-3-yloxy)-5-bromo-N-Cis-4-methoxycyclohexyl)pyrimidin-2-amine

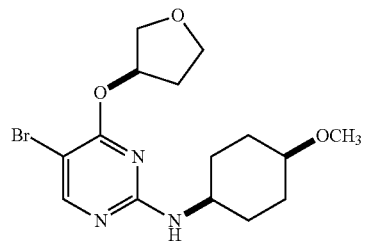

Using the procedure of Example 78, Step 2, (R)-5-bromo-2-chloro-4-(tetrahydrofuran-3-yloxy)pyrimidine was reacted with cis-4-methoxycyclohexanamine HCl salt to provide the title compound. $^1$H NMR (CDCl$_3$, 300 MHz) δ 1.3~2.2 (set of m, 10H), 3.30 (s, 3H), 3.40 (m, 1H), 3.6~4.1 (set of m, 4H+1H), 5.50 (m, 1H), 8.05 (s, 1H). MS (ESI) m/z: Found: 372 (M$^+$+1), Calc. 371 (M$^+$).

Step 3: Preparation of 4-((R)-Tetrahydrofuran-3-yloxy)-5-(2,3-dihydrobenzo[b][1,4]dioxin-6-yl)-N-((1s,4S)-4-methoxycyclohexyl)pyrimidin-2-amine

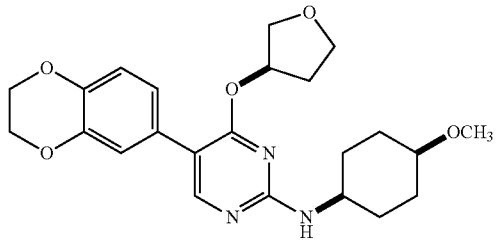

Using the procedure of Example 78, Step 3,4-((R)-tetrahydrofuran-3-yloxy)-5-bromo-N-cis-4-methoxycyclohexyl)pyrimidin-2-amine was reacted with 2,3-dihydrobenzo[b][1,4]dioxin-6-yl-6-boronic acid to provide the title compound. $^1$H NMR (CDCl$_3$, 300 MHz) δ 1.5~2.3 (set of m, 10H), 3.33 (s, 3H, OCH3), 3.39 (m, 1H), 3.8~3.9 (set of m, 4H), 4.10 (m, 1H), 4.26 (s, 4H), 5.56 (m, 1H), 6.85~6.9 (set of m, 3H, aromatic CH), 8.07 (s, 1H). MS (ESI) m/z: Found: 428.7 (M$^+$+1), Calc. 427.2 (M$^+$).

Example 87

General Experimental Procedure

Scheme 11 illustrates a general procedure for preparing compound 4C where R is aryl or heteroaryl. Compound 4A can be prepared using methods well-known in the art. For example compound 4A can be prepared by reacting 2,4-dichloro-5-bromo-pyrimidine with a desired tri(n-butyl)aryltin or tri(n-butyl)heteroaryltin in DMF in the presence of catalytic amount of bis(triphenylphosphine)palladium (II) dichloride at about 70-80° C. for about 18-24 h. Compound 4A can be converted to compound 4C via amination, followed by Suzuli coupling as shown in Scheme 11.

SCHEME 11

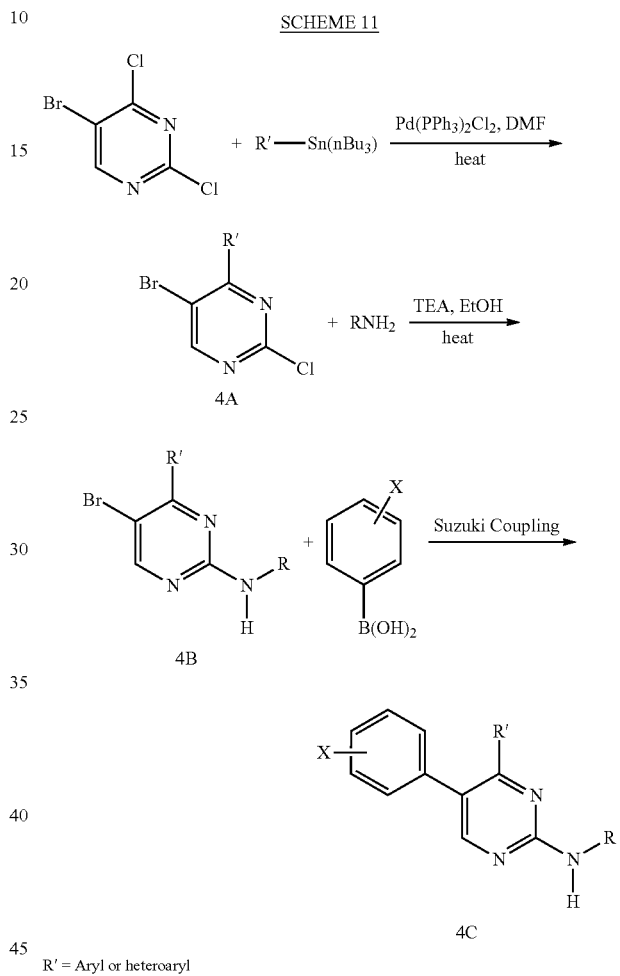

R' = Aryl or heteroaryl

Preparation of 4-(3,5-Dimethylisoxazol-4-yl)-5-(4-isopropoxyphenyl)-N-((1s,4s)-4-methylcyclohexyl)pyrimidin-2-amine The title compound was prepared using the specific synthetic process described below in Scheme 12.

SCHEME 12

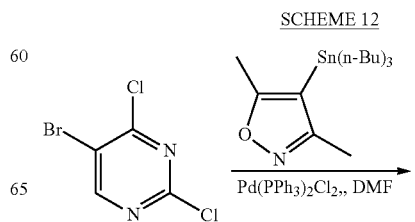

-continued

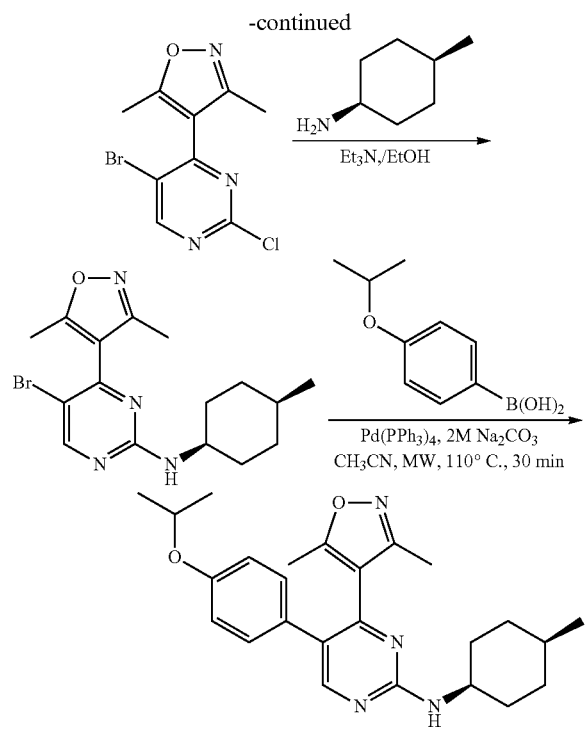

Step 1: Preparation of 4-(5-Bromo-2-chloropyrimidin-4-yl)-3,5-dimethylisoxazole

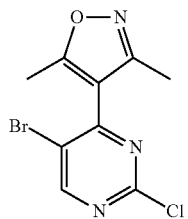

To a degassed with argon solution of 5-bromo-2,4-dichloropyrimidine (228 mg, 1.0 mmol) and 3,5-dimethyl-4-(tributylstannyl)isoxazole (772 mg, 2.0 mmol) in anhydrous DMF (2 mL), was added Pd(PPh$_3$)$_2$Cl$_2$ (35 mg, 1.04 mmol). The mixture was stirred at 70° C. for 16.5 h. DMF was evaporated. The resulting orange oil was purified on ISCO (hexane/ethyl acetate gradient, 5-25%) to give the title compound (211 mg, 73.0%). $^1$HNMR (CDCl$_3$): 8.81 (s, 1H), 2.44 (s, 3H), 2.30 (s, 3H). MS (ESI) m/z: Found: 288.0 (M$^+$+1), 290.0 (M$^+$+3), Calc. 286.9 (M$^+$).

Step 2: Preparation of 5-Bromo-4-(3,5-dimethylisoxazol-4-yl)-N-((1s,4s)-4-methylcyclohexyl)pyrimidin-2-amine

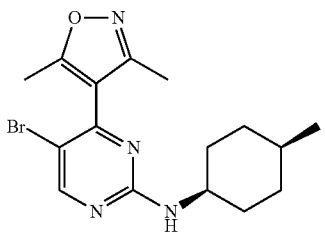 [SMILES: Cc1noc(C)c1-c1nc(N[C@H]2CC[C@@H](C)CC2)ncc1Br]

Using the procedure of Example 78, Step 2,4-(5-bromo-2-chloropyrimidin-4-yl)-3,5-dimethylisoxazole was reacted with cis-4-methylcyclohexylamine hydrochloride to provide the title compound in 71% yield. MS (ESI) m/z: Found: 365.0 (M$^+$+1), 367.0 (M$^+$+3), Calc. 364.1 (M$^+$).

Step 3: Preparation of 4-(3,5-Dimethylisoxazol-4-yl)-5-(4-isopropoxyphenyl)-N-((1s,4s)-4-methylcyclohexyl)pyrimidin-2-amine

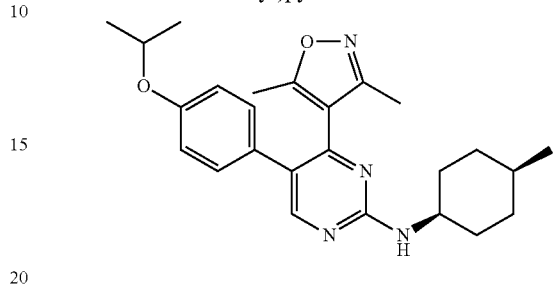

Using the procedure of Example 78, Step 3,5-bromo-4-(3,5-dimethylisoxazol-4-yl)-N-((1s,4s)-4-methylcyclohexyl)pyrimidin-2-amine was reacted with 4-isopropoxyphenyl boronic acid to provide the title compound (45.1% yield). $^1$H NMR (CDCl$_3$, 400 MHz) 8.35 (s, 1H), 7.02 (d, J=8.6 Hz, 2H), 6.83 (d, J=8.6 Hz, 2H), 5.50 (br s, 1H), 4.53 (septuplet, J=5.9-6.3 Hz, 1H), 4.15 (m, 1H), 2.05 (s, 3H), 2.00 (s, 3H), 1.76-1.87 (m, 2H), 1.46-1.76 (m, 5H), 1.33 (d, J=5.9 Hz, 6H). 1.18-1.37 (m, 2H), 0.94 (d, J=6.2 Hz, 3H). MS (ESI) m/z: Found: 421.2 (M$^+$+1), Calc. 420.3 (M$^+$).

Examples 88-249

Compounds listed in Table 2 below were prepared using procedures analogous to those described above for the synthesis of Examples 78-88 above using appropriate starting materials which are available commercially, prepared based on procedures known in the art, or prepared in a manner analogous to routes described above for other intermediates.

TABLE 2

| Example No. | Compound Name | MS Calc M$^+$ | MS Found M$^+$+1 |
|---|---|---|---|
| 88 | 5-(4-(difluoromethoxy)phenyl)-N-((1s,4s)-4-ethylcyclohexyl)pyrimidin-2-amine | 347.2 | 348.2 |
| 89 | N-((1s,4s)-4-ethylcyclohexyl)-5-(4-isopropoxyphenyl)pyrimidin-2-amine | 339.2 | 340.2 |
| 90 | 5-(4-cyclobutoxyphenyl)-N-((1s,4s)-4-methylcyclohexyl)pyrimidin-2-amine | 337.2 | 338.2 |
| 91 | N-cyclopentyl-5-(4-(difluoromethoxy)phenyl)pyrimidin-2-amine | 305.1 | 306.2 |
| 92 | N-(cyclohexylmethyl)-5-(4-(difluoromethoxy)phenyl)pyrimidin-2-amine | 333.2 | 334.2 |
| 93 | N-((1s,4s)-4-methylcyclohexyl)-5-(2,4,6-trimethoxyphenyl)pyrimidin-2-amine | 357.2 | 358.2 |
| 94 | N-((1s,4s)-4-methylcyclohexyl)-5-(6-(piperidin-1-yl)pyridin-3-yl)pyrimidin-2-amine | 351.2 | 352.2 |
| 95 | N-cyclopentyl-5-(4-isopropoxyphenyl)pyrimidin-2-amine | 297.2 | 298.2 |
| 96 | N-(4,4-difluorocyclohexyl)-5-(4-(difluoromethoxy)phenyl)pyrimidin-2-amine | 355.1 | 356.2 |
| 97 | 5-(4-(cyclopropylmethoxy)phenyl)-N-((1s,4s)-4-methylcyclohexyl)pyrimidin-2-amine | 337.2 | 338.2 |
| 98 | N-((1s,4s)-4-methylcyclohexyl)-5-(4-(2,2,2-trifluoroethoxy)phenyl)pyrimidin-2-amine | 365.2 | 366.2 |
| 99 | 5-(3-fluoro-4-(2,2,2-trifluoroethoxy)phenyl)-N-((1s,4s)-4-methylcyclohexyl)pyrimidin-2-amine | 383.2 | 384.2 |

TABLE 2-continued

| Example No. | Compound Name | MS Calc M+ | MS Found M+ + 1 |
|---|---|---|---|
| 100 | 5-(4-fluoro-3-(2,2,2-trifluoroethoxy)phenyl)-N-((1s,4s)-4-methylcyclohexyl)pyrimidin-2-amine | 383.2 | 384.2 |
| 101 | 5-(5-chloropyridin-3-yl)-N-((1s,4s)-4-methylcyclohexyl)pyrimidin-2-amine | 302.1 | 303.2 |
| 102 | 5-(4-isopropoxyphenyl)-4-methoxy-N-((1s,4s)-4-methylcyclohexyl)pyrimidin-2-amine | 355.2 | 356.2 |
| 103 | 4-methoxy-N-((1s,4s)-4-methylcyclohexyl)-5-(4-(trifluoromethoxy)phenyl)pyrimidin-2-amine | 381.2 | 382.2 |
| 104 | 5-(4-(difluoromethoxy)phenyl)-4-methoxy-N-((1s,4s)-4-methylcyclohexyl)pyrimidin-2-amine | 363.2 | 364.2 |
| 105 | 5-(4-tert-butoxyphenyl)-N-((1s,4s)-4-methylcyclohexyl)pyrimidin-2-amine | 339.2 | 340.2 |
| 106 | 5-(4-(5-methyl-1,3,4-oxadiazol-2-yl)phenyl)-N-((1s,4s)-4-methylcyclohexyl)pyrimidin-2-amine | 349.2 | 350.2 |
| 107 | N-cyclohexyl-5-(4-(difluoromethoxy)phenyl)-4-methoxypyrimidin-2-amine | 349.2 | 350.2 |
| 108 | N-bicyclo[2.2.1]heptan-2-yl)-5-(4-(trifluoromethoxy)phenyl)pyrimidin-2-amine | 349.2 | 350.2 |
| 109 | 5-(4-isopropoxyphenyl)-N-((1s,4s)-4-methylcyclohexyl)pyrimidin-2-amine | 379.2 | 380.2 |
| 110 | 5-(4-(difluoromethoxy)phenyl)-N-((1s,4s)-4-(trifluoromethyl)cyclohexyl)pyrimidin-2-amine | 387.1 | 388.2 |
| 111 | 4-methoxy-5-(2-methyl-4-(trifluoromethoxy)phenyl)-N-((1s,4s)-4-methylcyclohexyl)pyrimidin-2-amine | 395.2 | 396.2 |
| 112 | 4-methoxy-5-(2-methoxy-4-(trifluoromethoxy)phenyl)-N-((1s,4s)-4-methylcyclohexyl)pyrimidin-2-amine | 411.2 | 412.2 |
| 113 | 5-(5-chloro-2-methoxypyridin-4-yl)-N-((1s,4s)-4-methylcyclohexyl)pyrimidin-2-amine | 332.1 | 333.2 |
| 114 | N-((1s,4s)-4-methylcyclohexyl)-5-(2-methylpyridin-4-yl)pyrimidin-2-amine | 282.2 | 283.2 |
| 115 | 4-methoxy-N-((1s,4s)-4-methylcyclohexyl)-5-(4-(piperidin-1-yl)phenyl)pyrimidin-2-amine | 380.3 | 381.2 |
| 116 | 5-(2-methoxy-4-(trifluoromethoxy)phenyl)-N-((1s,4s)-4-methylcyclohexyl)pyrimidin-2-amine | 381.2 | 382.2 |
| 117 | 5-(4-(difluoromethoxy)phenyl)-N-(1-methylcyclohexyl)pyrimidin-2-amine | 333.2 | 334.2 |
| 118 | 5-(6-isopropoxypyridin-3-yl)-4-methoxy-N-((1s,4s)-4-methylcyclohexyl)pyrimidin-2-amine | 356.2 | 357.2 |
| 119 | 4-methoxy-N-((1s,4s)-4-methylcyclohexyl)-5-(6-(piperidin-1-yl)pyridin-3-yl)pyrimidin-2-amine | 381.3 | 382.2 |
| 120 | N-cyclohexyl-5-(2-methoxy-4-(trifluoromethoxy)phenyl)pyrimidin-2-amine | 367.2 | 368.4 |
| 121 | 4-methoxy-N-((1s,4s)-4-methylcyclohexyl)-5-(2-(trifluoromethyl)pyridin-4-yl)pyrimidin-2-amine | 366.2 | 367.4 |
| 122 | 5-(5-chloro-2-methoxypyridin-4-yl)-4-methoxy-N-((1s,4s)-4-methylcyclohexyl)pyrimidin-2-amine | 362.2 | 363.4 |
| 123 | 5-(4-(difluoromethoxy)phenyl)-N4,N4-dimethyl-N2-((1s,4s)-4-methylcyclohexyl)pyrimidine-2,4-diamine | 376.2 | 377.4 |
| 124 | 4-(cyclopropylmethoxy)-5-(4-isopropoxyphenyl)-N-((1s,4s)-4-methylcyclohexyl)pyrimidin-2-amine | 395.3 | 396.4 |
| 125 | 2-(4-(4-methoxy-2-((1s,4s)-4-methylcyclohexylamino)pyrimidin-5-yl)phenoxy)acetonitrile | 352.2 | 353.4 |
| 126 | 4-tert-butoxy-5-(4-isopropoxyphenyl)-N-((1s,4s)-4-methylcyclohexyl)pyrimidin-2-amine | 397.3 | 398.4 |
| 127 | 4-(cyclopropylmethoxy)-5-(4-(difluoromethoxy)phenyl)-N-((1s,4s)-4-methylcyclohexyl)pyrimidin-2-amine | 403.2 | 404.4 |
| 128 | 4-cyclobutoxy-5-(4-(difluoromethoxy)phenyl)-N-((1s,4s)-4-methylcyclohexyl)pyrimidin-2-amine | 403.2 | 404.4 |
| 129 | 4-cyclobutoxy-5-(4-isopropoxyphenyl)-N-((1s,4s)-4-methylcyclohexyl)pyrimidin-2-amine | 395.3 | 396.4 |
| 130 | 4-methoxy-N-((1s,4s)-4-methylcyclohexyl)-5-(6-(methylthio)pyridin-3-yl)pyrimidin-2-amine | 344.2 | 345.4 |
| 131 | 2-(4-(4-cyclobutoxy-2-((1s,4s)-4-methylcyclohexylamino)pyrimidin-5-yl)phenoxy)acetonitrile | 392.2 | 393.4 |
| 132 | N-(2-admantanyl)-5-(4-isopropoxyphenyl)-4-methoxypyrimidin-2-amine | 393.2 | 394.4 |
| 133 | 2-(4-(4-(cyclopropylmethoxy)-2-((1s,4s)-4-methylcyclohexylamino)pyrimidin-5-yl)phenoxy)acetonitrile | 392.2 | 393.4 |
| 134 | 2-(4-(2-((1s,4s)-4-methylcyclohexylamino)-4-morpholinopyrimidin-5-yl)phenoxy)acetonitrile | 407.2 | 408.4 |
| 135 | 4-methoxy-N-((1s,4s)-4-methylcyclohexyl)-5-(6-(methylsulfonyl)pyridin-3-yl)pyrimidin-2-amine | 376.2 | 377.4 |
| 136 | 5-(4-(difluoromethoxy)phenyl)-N-((1s,4s)-4-methylcyclohexyl)-4-morpholinopyrimidin-2-amine | 418.2 | 419.4 |
| 137 | 5-(4-isopropoxyphenyl)-4,6-dimethyl-N-((1s,4s)-4-methylcyclohexyl)pyrimidin-2-amine | 353.3 | 354.4 |
| 138 | 4-methoxy-N-((1s,4s)-4-methylcyclohexyl)-5-(6-(pyrrolidin-1-yl)pyridin-3-yl)pyrimidin-2-amine | 367.2 | 368.4 |
| 139 | 5-(6-(dimethylamino)pyridin-3-yl)-4-methoxy-N-((1s,4s)-4-methylcyclohexyl)pyrimidin-2-amine | 341.2 | 342.4 |
| 140 | 2-(4-(4,6-dimethyl-2-((1s,4s)-4-methylcyclohexylamino)pyrimidin-5-yl)phenoxy)acetonitrile | 350.2 | 351.4 |
| 141 | 4-(cyclopropylmethoxy)-N-((1s,4s)-4-methylcyclohexyl)-5-(6-(piperidin-1-yl)pyridin-3-yl)pyrimidin-2-amine | 421.3 | 422.5 |
| 142 | 4-methoxy-N-((1s,4s)-4-methylcyclohexyl)-5-(6-(2,2,2-trifluoroethoxy)pyridin-3-yl)pyrimidin-2-amine | 396.2 | 397.4 |
| 143 | 4-(4-methoxy-2-((1s,4s)-4-methylcyclohexylamino)pyrimidin-5-yl)picolinonitrile | 323.2 | 324.4 |
| 144 | 5-(4-(difluoromethoxy)phenyl)-N-((1s,4s)-4-methylcyclohexyl)-4-(pyrrolidin-1-yl)pyrimidin-2-amine | 402.2 | 403.4 |
| 145 | 5-(6-(cyclopropylmethoxy)pyridin-3-yl)-4-methoxy-N-((1s,4s)-4-methylcyclohexyl)pyrimidin-2-amine | 368.2 | 369.4 |
| 146 | 2-(4-(4-methoxy-2-(2-admantanylamino)pyrimidin-5-yl)phenoxy)acetonitrile | 390.2 | 391.3 |
| 147 | 5-(6-(dimethylamino)pyridin-3-yl)-4-methoxy-N-(2-admantanyl)pyrimidin-2-amine | 379.2 | 380.3 |
| 148 | 5-(6-(dimethylamino)pyridin-3-yl)-N-((1s,4s)-4-methylcyclohexyl)-4-(tetrahydro-2H-pyran-4-yloxy)pyrimidin-2-amine | 411.3 | 412.3 |
| 149 | 2-(4-(2-((1s,4s)-4-methylcyclohexylamino)-4-(tetrahydro-2H-pyran-4-yloxy)pyrimidin-5-yl)phenoxy)acetonitrile | 422.2 | 423.2 |
| 150 | 2-(4-(2-((1s,4s)-4-methylcyclohexylamino)-4-(tetrahydrofuran-3-yloxy)pyrimidin-5-yl)phenoxy)acetonitrile | 408.2 | 409.2 |
| 151 | 5-(6-(dimethylamino)pyridin-3-yl)-N-((1s,4s)-4-methylcyclohexyl)-4-(tetrahydrofuran-3-yloxy)pyrimidin-2-amine | 397.3 | 398.3 |
| 152 | 4-(cyclopropylmethoxy)-5-(6-methoxypyridin-3-yl)-N-((1s,4s)-4-methylcyclohexyl)pyrimidin-2-amine | 368.2 | 369.2 |
| 153 | 4-(cyclopropylmethoxy)-5-(6-(dimethylamino)pyridin-3-yl)-N-((1s,4s)-4-methylcyclohexyl)pyrimidin-2-amine | 381.3 | 382.3 |
| 154 | 4-(cyclopropylmethoxy)-5-(2-methoxypyridin-4-yl)-N-((1s,4s)-4-methylcyclohexyl)pyrimidin-2-amine | 368.2 | 369.2 |
| 155 | 4-methoxy-5-(3-(5-methyl-1,3,4-oxadiazol-2-yl)phenyl)-N-((1s,4s)-4-methylcyclohexyl)pyrimidin-2-amine | 379.2 | 380.2 |
| 156 | 5-(2-isopropoxypyridin-4-yl)-4-methoxy-N-((1s,4s)-4-methylcyclohexyl)pyrimidin-2-amine | 356.2 | 357.2 |
| 157 | 5-(2,6-dimethoxypyridin-3-yl)-4-methoxy-N-((1s,4s)-4-methylcyclohexyl)pyrimidin-2-amine | 358.2 | 359.2 |
| 158 | 5-(benzo[d]thiazol-5-yl)-4-methoxy-N-((1s,4s)-4-methylcyclohexyl)pyrimidin-2-amine | 354.2 | 355.2 |

TABLE 2-continued

| Example No. | Compound Name | MS Calc M+ | MS Found M+ + 1 |
|---|---|---|---|
| 159 | 2-(4-(4-methoxy-6-methyl-2-((1s,4s)-4-methylcyclohexylamino)pyrimidin-5-yl)phenoxy)acetonitrile | 366.2 | 367.2 |
| 160 | 2-(4-(2-((1s,4R)-4-methylcyclohexylamino)-4-((S)-tetrahydrofuran-3-yloxy)pyrimidin-5-yl)phenoxy)acetonitrile | 408.2 | 409.2 |
| 161 | 5-(6-isopropoxypyridin-3-yl)-N-((1s,4R)-4-methylcyclohexyl)-4-((S)-tetrahydrofuran-3-yloxy)pyrimidin-2-amine | 412.3 | 413.2 |
| 162 | 2-(4-(2-((1s,4S)-4-methylcyclohexylamino)-4-((R)-tetrahydrofuran-3-yloxy)pyrimidin-5-yl)phenoxy)acetonitrile | 408.2 | 409.1 |
| 163 | 5-(6-isopropoxypyridin-3-yl)-N-((1s,4S)-4-methylcyclohexyl)-4-((R)-tetrahydrofuran-3-yloxy)pyrimidin-2-amine | 412.3 | 413.2 |
| 164 | 5-(6-(dimethylamino)pyridin-3-yl)-N-((1s,4s)-4-methylcyclohexyl)-4-(tetrahydro-2H-pyran-3-yloxy)pyrimidin-2-amine | 411.3 | 412.3 |
| 165 | 5-(3-(5-methyl-1,3,4-oxadiazol-2-yl)phenyl)-N-((1s,4s)-4-methylcyclohexyl)-4-(tetrahydro-2H-pyran-3-yloxy)pyrimidin-2-amine | 449.2 | 450.4 |
| 166 | 4-methoxy-5-(4-methyl-3,4-dihydro-2H-pyrido[3,2-b][1,4]oxazin-7-yl)-N-((1s,4s)-4-methylcyclohexyl)pyrimidin-2-amine | 369.2 | 370.3 |
| 167 | 2-(4-(2-((1s,4s)-4-methylcyclohexylamino)-4-(tetrahydro-2H-pyran-3-yloxy)pyrimidin-5-yl)phenoxy)acetonitrile | 422.2 | 423.2 |
| 168 | 2-(4-(2-((1s,4s)-4-methylcyclohexylamino)-4-((tetrahydrofuran-3-yl)methoxy)pyrimidin-5-yl)phenoxy)acetonitrile | 422.2 | 423.2 |
| 169 | 5-(6-(dimethylamino)pyridin-3-yl)-N-((1s,4s)-4-methylcyclohexyl)-4-((tetrahydrofuran-3-yl)methoxy)pyrimidin-2-amine | 411.3 | 412.3 |
| 170 | 2-(4-(2-((1s,4s)-4-methylcyclohexylamino)-4-((tetrahydro-2H-pyran-4-yl)methoxy)pyrimidin-5-yl)phenoxy)acetonitrile | 436.3 | 437.2 |
| 171 | 5-(6-isopropoxypyridin-3-yl)-N-((1s,4s)-4-methylcyclohexyl)-4-((tetrahydro-2H-pyran-4-yl)methoxy)pyrimidin-2-amine | 440.3 | 441.2 |
| 172 | 4-methoxy-5-(1-methyl-1H-indazol-5-yl)-N-((1s,4s)-4-methylcyclohexyl)pyrimidin-2-amine | 351.2 | 352.2 |
| 173 | 2',4-dimethoxy-N-((1s,4s)-4-methylcyclohexyl)-5,5'-bipyrimidin-2-amine | 329.2 | 330.2 |
| 174 | 2',4,4'-trimethoxy-N-((1s,4s)-4-methylcyclohexyl)-5,5'-bipyrimidin-2-amine | 359.2 | 360.2 |
| 175 | 4-methoxy-5-(2-methyl-2H-indazol-6-yl)-N-((1s,4s)-4-methylcyclohexyl)pyrimidin-2-amine | 351.2 | 352.2 |
| 176 | 5-(4-isopropoxyphenyl)-N-((1s,4S)-4-methylcyclohexyl)-4-((R)-tetrahydrofuran-3-yloxy)pyrimidin-2-amine | 411.3 | 412.2 |
| 177 | 5-(4-(difluoromethoxy)phenyl)-N-((1s,4S)-4-methylcyclohexyl)-4-((R)-tetrahydrofuran-3-yloxy)pyrimidin-2-amine | 419.2 | 420.1 |
| 178 | 5-(4-isopropoxyphenyl)-N-((1s,4s)-4-methylcyclohexyl)-4-((tetrahydrofuran-2-yl)methoxy)pyrimidin-2-amine | 425.3 | 426.2 |
| 179 | 5-(4-(difluoromethoxy)phenyl)-N-((1s,4s)-4-methylcyclohexyl)-4-((tetrahydrofuran-3-yl)methoxy)pyrimidin-2-amine | 433.2 | 434.2 |
| 180 | 5-(benzo[d]thiazol-5-yl)-N-((1s,4S)-4-methylcyclohexyl)-4-((R)-tetrahydrofuran-3-yloxy)pyrimidin-2-amine | 410.2 | 411.2 |
| 181 | 5-(2,6-dimethoxypyridin-3-yl)-N-((1s,4S)-4-methylcyclohexyl)-4-((R)-tetrahydrofuran-3-yloxy)pyrimidin-2-amine | 414.2 | 415.2 |
| 182 | 2-(4-(4-(benzyloxy)-2-((1s,4s)-4-methylcyclohexylamino)pyrimidin-5-yl)phenoxy)acetonitrile | 428.2 | 429.2 |
| 183 | 5-(4-isopropoxyphenyl)-N-((1s,4R)-4-methylcyclohexyl)-4-((S)-tetrahydrofuran-3-yloxy)pyrimidin-2-amine | 411.3 | 412.2 |
| 184 | 5-(4-(difluoromethoxy)phenyl)-N-((1s,4R)-4-methylcyclohexyl)-4-((S)-tetrahydrofuran-3-yloxy)pyrimidin-2-amine | 419.2 | 420.2 |
| 185 | 5-(3-(5-methyl-1,3,4-oxadiazol-2-yl)phenyl)-N-((1s,4S)-4-methylcyclohexyl)-4-((R)-tetrahydrofuran-3-yloxy)pyrimidin-2-amine | 435.2 | 436.2 |
| 186 | 5-(4-isopropoxyphenyl)-N-((1s,4s)-4-methylcyclohexyl)-4-(tetrahydro-2H-pyran-3-yloxy)pyrimidin-2-amine | 425.3 | 425.2 |
| 187 | 5-(2-methyl-2H-indazol-6-yl)-N-((1s,4S)-4-methylcyclohexyl)-4-((R)-tetrahydrofuran-3-yloxy)pyrimidin-2-amine | 407.2 | 408.2 |
| 188 | 5-(4-isopropoxyphenyl)-N-((1s,4R)-4-methylcyclohexyl)-4-(((S)-tetrahydrofuran-3-yl)methoxy)pyrimidin-2-amine | 425.3 | 426.2 |
| 189 | 2-(4-(2-((1s,4s)-4-methylcyclohexylamino)-4-((1-methylcyclopropyl)methoxy)pyrimidin-5-yl)phenoxy)acetonitrile | 406.2 | 407.2 |
| 190 | 4-methoxy-5-(2-methylbenzo[d]oxazol-6-yl)-N-((1s,4s)-4-methylcyclohexyl)pyrimidin-2-amine | 352.2 | 353.2 |
| 191 | N-((1s,4s)-4-methylcyclohexyl)-4-(tetrahydro-2H-pyran-4-yl)methoxy)-5-(4-(trifluoromethoxy)phenyl)pyrimidin-2-amine | 465.2 | 466.2 |
| 192 | 5-(4-isopropoxyphenyl)-N-((1s,4s)-4-methylcyclohexyl)-4-((tetrahydro-2H-pyran-4-yl)methoxy)pyrimidin-2-amine | 439.3 | 440.2 |
| 193 | N-((1s,4s)-4-methylcyclohexyl)-4-((1-methylcyclopropyl)methoxy)-5-(4-(trifluoromethoxy)phenyl)pyrimidin-2-amine | 435.2 | 436.2 |
| 194 | 5-(4-isopropoxyphenyl)-4-methoxy-6-methyl-N-((1s,4s)-4-methylcyclohexyl)pyrimidin-2-amine | 369.2 | 370.2 |
| 195 | N4-(2-methoxyethyl)-N4-methyl-N2-((1s,4s)-4-methylcyclohexyl)-5-(4-(trifluoromethoxy)phenyl)pyrimidine-2,4-diamine | 438.2 | 439.2 |
| 196 | N-((1s,4s)-4-methylcyclohexyl)-4-((tetrahydro-2H-pyran-2-yl)methoxy)-5-(4-(trifluoromethoxy)phenyl)pyrimidin-2-amine | 465.2 | 466.2 |
| 197 | 4-methoxy-6-methyl-5-(2-methyl-2H-indazol-6-yl)-N-((1s,4s)-4-methylcyclohexyl)pyrimidin-2-amine | 365.2 | 366.2 |
| 198 | 4-((2,5-dimethyloxazol-4-yl)methoxy)-5-(2-methyl-2H-indazol-6-yl)-N-((1s,4s)-4-methylcyclohexyl)pyrimidin-2-amine | 446.2 | 447.2 |
| 199 | 4-((2,5-dimethyloxazol-4-yl)methoxy)-5-(4-isopropoxyphenyl)-N-((1s,4s)-4-methylcyclohexyl)pyrimidin-2-amine | 450.3 | 451.2 |
| 200 | 5-(2-methyl-2H-indazol-5-yl)-N-((1s,4S)-4-methylcyclohexyl)-4-((R)-tetrahydrofuran-3-yloxy)pyrimidin-2-amine | 407.2 | 408.2 |
| 201 | 5-(2,3-dihydrobenzo[b][1,4]dioxin-6-yl)-N-((1s,4S)-4-methylcyclohexyl)-4-((R)-tetrahydrofuran-3-yloxy)pyrimidin-2-amine | 411.2 | 412.2 |
| 202 | 4-(3-methoxyphenoxy)-5-(2-methyl-2H-indazol-6-yl)-N-((1s,4s)-4-methylcyclohexyl)pyrimidin-2-amine | 443.2 | 444.2 |
| 203 | 2-(4-(4-(cyclopentylmethoxy)-2-((1s,4s)-4-methylcyclohexylamino)pyrimidin-5-yl)phenoxy)acetonitrile | 420.3 | 421.2 |
| 204 | 5-(4-isopropoxyphenyl)-N-((1s,4S)-4-methylcyclohexyl)-4-(((R)-tetrahydrofuran-2-yl)methoxy)pyrimidin-2-amine | 425.3 | 426.2 |
| 205 | N-((1s,4S)-4-methylcyclohexyl)-5-(6-(tetrahydro-2H-pyran-4-yloxy)pyridin-3-yl)-4-((R)-tetrahydrofuran-3-yloxy)pyrimidin-2-amine | 454.3 | 455.2 |
| 206 | 4-methyl-5-(2-methyl-2H-indazol-6-yl)-N-((1s,4S)-4-methylcyclohexyl)-6-((R)-tetrahydrofuran-3-yloxy)pyrimidin-2-amine | 421.3 | 422.2 |
| 207 | 5-(2-methyl-2H-indazol-6-yl)-N-((1s,4S)-4-methylcyclohexyl)-4-(((R)-tetrahydrofuran-2-yl)methoxy)pyrimidin-2-amine | 421.3 | 422.2 |
| 208 | 5-(2,3-dihydrobenzo[b][1,4]dioxin-6-yl)-N-((1s,4S)-4-methylcyclohexyl)-4-(((R)-tetrahydrofuran-2-yl)methoxy)pyrimidin-2-amine | 425.2 | 426.2 |

TABLE 2-continued

| Example No. | Compound Name | MS Calc M+ | MS Found M+ + 1 |
|---|---|---|---|
| 209 | 5-(2,3-dihydrobenzo[b][1,4]dioxin-6-yl)-N-((1s,4s)-4-methylcyclohexyl)-4-((tetrahydro-2H-pyran-4-yl)methoxy)pyrimidin-2-amine | 439.3 | 440.2 |
| 210 | 5-(2,3-dihydrobenzo[b][1,4]dioxin-6-yl)-N-((1s,4s)-4-methylcyclohexyl)-4-((tetrahydro-2H-pyran-2-yl)methoxy)pyrimidin-2-amine | 439.3 | 440.2 |
| 211 | N-((1s,4S)-4-methylcyclohexyl)-5-(4-morpholinophenyl)-4-((R)-tetrahydrofuran-3-yloxy)pyrimidin-2-amine | 438.3 | 439.2 |
| 212 | 5-(2,3-dihydrobenzo[b][1,4]dioxin-6-yl)-N-((1s,4R)-4-methylcyclohexyl)-4-(((S)-tetrahydrofuran-3-yl)methoxy)pyrimidin-2-amine | 425.2 | 426.2 |
| 213 | 5-(4-(5-methyl-1,3,4-oxadiazol-2-yl)phenyl)-N-((1s,4S)-4-methylcyclohexyl)-4-((R)-tetrahydrofuran-3-yloxy)pyrimidin-2-amine | 435.2 | 436.2 |
| 214 | 5-(3,4-dihydro-2H-benzo[b][1,4]dioxepin-7-yl)-N-((1s,4S)-4-methylcyclohexyl)-4-((R)-tetrahydrofuran-3-yloxy)pyrimidin-2-amine | 425.2 | 426.2 |
| 215 | 5-(1-methyl-1H-indazol-5-yl)-N-((1s,4S)-4-methylcyclohexyl)-4-((R)-tetrahydrofuran-3-yloxy)pyrimidin-2-amine | 407.2 | 408.2 |
| 216 | 5-(2-methylbenzo[d]oxazol-6-yl)-N-((1s,4S)-4-methylcyclohexyl)-4-((R)-tetrahydrofuran-3-yloxy)pyrimidin-2-amine | 408.2 | 409.2 |
| 217 | 5-(2-methylbenzo[d]thiazol-5-yl)-N-((1s,4S)-4-methylcyclohexyl)-4-((R)-tetrahydrofuran-3-yloxy)pyrimidin-2-amine | 424.2 | 425.2 |
| 218 | 5-(2,3-dihydrobenzo[b][1,4]dioxin-6-yl)-4-methyl-N-((1s,4S)-4-methylcyclohexyl)-6-((R)-tetrahydrofuran-3-yloxy)pyrimidin-2-amine | 425.2 | 426.2 |
| 219 | methyl 3-(5-(2-methyl-2H-indazol-6-yl)-2-((1s,4s)-4-methylcyclohexylamino)pyrimidin-4-yloxy)pyrrolidine-1-carboxylate | 464.3 | 465.3 |
| 220 | 5-(2-methyl-2H-indazol-5-yl)-N-((1s,4s)-4-methylcyclohexyl)-4-((tetrahydro-2H-pyran-4-yl)methoxy)pyrimidin-2-amine | 435.3 | 436.2 |
| 221 | N-((1s,4S)-4-methylcyclohexyl)-5-(6-(piperidin-1-yl)pyridin-3-yl)-4-((R)-tetrahydrofuran-3-yloxy)pyrimidin-2-amine | 437.3 | 438.2 |
| 222 | 5-(4-methyl-3,4-dihydro-2H-benzo[b][1,4]oxazin-7-yl)-N-((1s,4S)-4-methylcyclohexyl)-4-((R)-tetrahydrofuran-3-yloxy)pyrimidin-2-amine | 424.3 | 425.2 |
| 223 | 5-(2,2-difluorobenzo[d][1,3]dioxol-5-yl)-N-((1s,4S)-4-methylcyclohexyl)-4-((R)-tetrahydrofuran-3-yloxy)pyrimidin-2-amine | 433.2 | 434.2 |
| 224 | 5-(benzo[c][1,2,5]oxadiazol-5-yl)-N-((1s,4S)-4-methylcyclohexyl)-4-((R)-tetrahydrofuran-3-yloxy)pyrimidin-2-amine | 395.2 | 396.2 |
| 225 | 5-(2-methylbenzo[d]oxazol-5-yl)-N-((1s,4S)-4-methylcyclohexyl)-4-((R)-tetrahydrofuran-3-yloxy)pyrimidin-2-amine | 408.2 | 409.2 |
| 226 | 5-(2,3-dihydrobenzo[b][1,4]dioxin-6-yl)-N-((1s,4s)-4-methylcyclohexyl)-4-(oxetan-3-yloxy)pyrimidin-2-amine | 397.2 | 398.2 |
| 227 | 5-(1-methyl-1H-indazol-5-yl)-N-((1s,4s)-4-methylcyclohexyl)-4-(oxetan-3-yloxy)pyrimidin-2-amine | 393.2 | 394.2 |
| 228 | N-((1s,4s)-4-methylcyclohexyl)-5-(4-morpholinophenyl)-4-(oxetan-3-yloxy)pyrimidin-2-amine | 424.3 | 425.2 |
| 229 | N-((1s,4S)-4-methylcyclohexyl)-5-(1-methylindolin-5-yl)-4-((R)-tetrahydrofuran-3-yloxy)pyrimidin-2-amine | 408.3 | 409.3 |
| 230 | 5-(2-((1s,4S)-4-methylcyclohexylamino)-4-((R)-tetrahydrofuran-3-yloxy)pyrimidin-5-yl)indolin-2-one | 408.2 | 409.2 |
| 231 | 5-(2,3-dihydrobenzo[b][1,4]dioxin-6-yl)-N-((1s,4S)-4-methylcyclohexyl)-4-((R)-tetrahydro-2H-pyran-3-yloxy)pyrimidin-2-amine | 425.2 | 426.2 |
| 232 | 5-(5-chloro-2-methoxypyridin-4-yl)-N-((1s,4S)-4-methylcyclohexyl)-4-((R)-tetrahydrofuran-3-yloxy)pyrimidin-2-amine | 418.2 | 419.2 |
| 233 | 5-(2-(methoxymethyl)benzo[d]oxazol-5-yl)-N-((1s,4S)-4-methylcyclohexyl)-4-((R)-tetrahydrofuran-3-yloxy)pyrimidin-2-amine | 438.2 | 439.2 |
| 234 | N-((1s,4s)-4-methylcyclohexyl)-5-(4-morpholinophenyl)-4-((tetrahydro-2H-pyran-4-yl)methoxy)pyrimidin-2-amine | 466.3 | 467.3 |
| 235 | 5-(1-methyl-1H-indazol-5-yl)-N-((1s,4S)-4-methylcyclohexyl)-4-((tetrahydro-2H-pyran-4-yl)methoxy)pyrimidin-2-amine | 435.3 | 436.2 |
| 236 | 5-(2-methylbenzo[d]oxazol-5-yl)-N-((1s,4S)-4-methylcyclohexyl)-4-((tetrahydro-2H-pyran-4-yl)methoxy)pyrimidin-2-amine | 436.3 | 437.3 |
| 237 | 5-(1-methyl-1H-indazol-5-yl)-N-((1s,4S)-4-methylcyclohexyl)-4-((R)-tetrahydro-2H-pyran-3-yloxy)pyrimidin-2-amine | 421.3 | 422.2 |
| 238 | 5-(2-methyl-2H-indazol-5-yl)-N-((1s,4S)-4-methylcyclohexyl)-4-((R)-tetrahydro-2H-pyran-3-yloxy)pyrimidin-2-amine | 421.3 | 422.2 |
| 239 | N-((1s,4S)-4-methylcyclohexyl)-5-(4-morpholinophenyl)-4-((R)-tetrahydro-2H-pyran-3-yloxy)pyrimidin-2-amine | 452.3 | 453.2 |
| 240 | 1-methyl-5-(2-((1s,4S)-4-methylcyclohexylamino)-4-((R)-tetrahydrofuran-3-yloxy)pyrimidin-5-yl)indolin-2-one | 422.2 | 423.2 |
| 241 | 5-(2-methylbenzo[d]thiazol-5-yl)-N-((1s,4s)-4-methylcyclohexyl)-4-(oxetan-3-yloxy)pyrimidin-2-amine | 410.2 | 411.2 |
| 242 | N-((1s,4s)-4-methylcyclohexyl)-4-(oxetan-3-yloxy)-5-(6-(piperidin-1-yl)pyridin-3-yl)pyrimidin-2-amine | 423.3 | 424.4 |
| 243 | 5-(3,4-dihydro-2H-benzo[b][1,4]dioxepin-7-yl)-N-((1s,4s)-4-methylcyclohexyl)-4-(oxetan-3-yloxy)pyrimidin-2-amine | 411.2 | 412.3 |
| 244 | 5-(2-methyl-1,3-benzoxazol-5-yl)-N-(4-methylcyclohexyl)-4-(oxetan-3-yloxy)pyrimidin-2-amine | 394.2 | 395.2 |
| 245 | 5-(2-methyl-2H-indazol-5-yl)-N-(4-methylcyclohexyl)-4-(oxetan-3-yloxy)pyrimidin-2-amine | 393.2 | 394.3 |
| 246 | 5-(2-methyl-2H-indazol-6-yl)-N-(4-methylcyclohexyl)-4-(oxetan-3-yloxy)pyrimidin-2-amine | 393.2 | 394.3 |
| 247 | 4-[(2R)-1,4-dioxan-2-ylmethoxy]-N-(4-methylcyclohexyl)-5-[4-(morpholin-4-yl)phenyl]pyrimidin-2-amine | 468.3 | 469.2 |
| 248 | isopropyl 3-(5-(2,3-dihydrobenzo[b][1,4]dioxin-6-yl)-2-((1s,4s)-4-methylcyclohexylamino)pyrimidin-4-yloxy)pyrrolidine-1-carboxylate | 496.3 | 497.2 |
| 249 | 1-(3-(5-(2,3-dihydrobenzo[b][1,4]dioxin-6-yl)-2-((1s,4s)-4-methylcyclohexylamino)pyrimidin-4-yloxy)pyrrolidin-1-yl)ethanone | 452.2 | 453.3 |

Example 250

Dual Corrector Potentiator Assay

The ability of exemplary compounds to correct the processing defect of ΔF508 CTFR, i.e. increase the surface expression of CFTR channels, and potentiate existing channels was demonstrated in an FRT cell electrophysiological (Ussing chamber) assay. FRT epithelial cell monolayers were grown on Snapwell filter inserts and optionally treated with a reference corrector N-(2-(5-chloro-2-methoxyphenylamino)-4'-methyl-4,5'-bithiazol-2'-yl)benzamide. The cells were exposed to a compound of the invention for 24 hours prior to the assay. The inserts were transferred to a Navicyte Ussing recording chamber and superfused with a HEPES buffered physiological saline (HB-PS) with composition (in mM): NaCl, 137; KCl, 4.0; CaCl$_2$, 1.8; MgCl$_2$, 1; HEPES, 10; Glucose, 10; pH adjusted to 7.4 with NaOH. The mucosal solution was 10CF-PS (composition in mM: Na-gluconate, 137; KCl, 4; CaCl$_2$, 1.8; MgCl$_2$, 1; HEPES, 10; Mannitol, 10; pH adjusted to 7.4 with N-methyl-D-glucamine) to create a transepithelial Cl ion gradient. A Physiologic Instruments VCC MC6 epithelial voltage clamp (Physiologic Instruments, Inc., San Diego, Calif.) was used to record the short circuit current (ISC).

Inserts were voltage clamped at 0 mV to measure the ISC. 10CF-PS solution (5 ml) was added to the mucosal (top) side of the Snapwell filter and HB-PS solution (5 mL) was added to the serosal (bottom) side of the Snapwell filter insert to permeabilize the serosal membrane. Solution additions and replacements in the Navicyte chambers were performed in a way to maintain a hydrostatic pressure gradient from mucosal to serosal sides of the filters by maintaining a solution level greater or equal in the mucosal chamber relative to the serosal chamber during solution changes. After acquisition of at least 10 minutes of baseline current, agonists (final concentrations: 10 μM forskolin, 100 μM 3-isobutyl-1-methylxanthine [IBMX] and 20 μM genistein) and antagonist (final concentration: 10 μM CFTRinh-172) were applied sequentially and cumulatively at 10 minute intervals for forskolin and IBMX, and at 15 minute intervals for genistein and CFTRinh-172, to both serosal and mucosal epithelial surfaces.

Agonists were prepared as 200×-1000× concentrated solutions in HP-PS and 10CF-PS. Agonist stocks prepared in HB-PS were added to the serosal surface, while agonist stocks prepared in 10CF-PS were added to the mucosal surface. In potentiator assays, appropriate volumes from 10 mM test compound solution in DMSO were added to the mucosal 10CF-PS solution. Agonists were diluted to the final working concentration in the Navicyte chamber by removal of chamber solution and addition of the concentrated stock solution. Order of solution removal was serosal then mucosal and for solution additions mucosal then serosal in order to maintain a hydrostatic pressure gradient from mucosal to serosal during solution changes. Transepithelial resistance was monitored every 20 s with 10 mV voltage steps.

EC$_{50}$ values are defined as the concentration of compound that gives a >25% increase in whole cell Cl⁻ conductance (compared to DMSO at 37° C. as a vehicle) at 10 μM. The corrector efficacy was measured as a percentage change in agonist+compound vs. agonist: $\Delta I_{compound}$(forskolin+IBMX+genistein)/$\Delta I_{vehicle}$(forskolin+IBMX+genistein). The potentiator efficacy was measured as a percentage change in forskolin activity: ΔI(forskolin+compound)/ΔI (forskolin+IBMX+genistein).

Table 3 provides results for several exemplary compounds. Corrector efficacy ranges correspond to +=<2, ++=2-3, and +++=>3. Potentiator efficacy ranges correspond to +=<0.3, ++=0.3-0.6, and +++=>0.6.

TABLE 3

| Example No. | Name | Corrector EC$_{50}$ μM | Corrector Efficacy | Potentiator EC$_{50}$ μM | Potentiator Efficacy |
|---|---|---|---|---|---|
| 79 | N-cyclohexyl-5-(4-trifluoromethoxy)-phenyl)pyrimidin-2-amine | <10 | ++ | <3 | +++* |
| 4 | N-((1S,4S)-4-methylcyclohexyl)-5-(4-(trifluoromethoxy)phenyl)pyrimidin-2-amine | <10 | +++ | <3<br><3 | +++*<br>+++** |
| 19 | 5-(4-(difluoromethoxy)phenyl)-N-((1s,4s)-4-methylcyclohexyl)pyrimidin-2-amine | <10 | +++ | <3 | +++** |
| 23 | 5-(4-isopropoxyphenyl)-N-((1s,4s)-4-methylcyclohexyl)pyrimidin-2-amine | <10 | +++ | <3 | +++** |
| 27 | 5-(4-methoxyphenyl)-N-((1s,4s)-4-methylcyclohexyl)pyrimidin-2-amine | <10 | +++ | <3 | ++** |
| 7 | 5-(4-isopropoxyphenyl)-4-methoxy-N-((1S,4S)-4-methylcyclohexyl)pyrimidin-2-amine | <10 | +++ | <10 | ++** |
| 58 | 4-methoxy-N-((1s,4s)-4-methylcyclohexyl)-5-(4-(trifluoromethoxy)phenyl)pyrimidin-2-amine | <10 | +++ | <3 | +++** |
| 59 | 5-(4-(difluoromethoxy)phenyl)-4-methoxy-N-((1s,4s)-4-methylcyclohexyl)pyrimidin-2-amine | <10 | +++ | <3 | ++** |
| 102 | 5-(4-isopropoxyphenyl)-4-methoxy-N-((1s,4s)-4-methylcyclohexyl)pyrimidin-2-amine | — | — | <3 | ++ |
| 103 | 4-methoxy-N-((1s,4s)-4-methylcyclohexyl)-5-(4-(trifluoromethoxy)phenyl)pyrimidin-2-amine | — | — | <3 | ++ |
| 104 | 5-(4-(difluoromethoxy)phenyl)-4-methoxy-N-((1s,4s)-4-methylcyclohexyl)pyrimidin-2-amine | — | — | <3 | ++ |

TABLE 3-continued

| Example No. | Name | Corrector EC$_{50}$ μM | Corrector Efficacy | Potentiator EC$_{50}$ μM | Potentiator Efficacy |
| --- | --- | --- | --- | --- | --- |
| 118 | 5-(6-isopropoxypyridin-3-yl)-4-methoxy-N-((1s,4s)-4-methylcyclohexyl)pyrimidin-2-amine | <10 | +++ | — | — |
| 119 | 4-methoxy-N-((1s,4s)-4-methylcyclohexyl)-5-(6-(piperidin-1-yl)pyridin-3-yl)pyrimidin-2-amine | <10 | +++ | — | — |
| 125 | 2-(4-(4-methoxy-2-((1s,4s)-4-methylcyclohexylamino)-pyrimidin-5-yl)phenoxy)-acetonitrile | >20 | +++ | — | — |
| 133 | 2-(4-(4-(cyclopropyl methoxy)-2-((1s,4s)-4-methylcyclohexylamino) pyrimidin-5-yl)phenoxy) acetonitrile | >20 | +++ | — | — |
| 143 | 4-(4-methoxy-2-((1s,4s)-4-methylcyclohexylamino)pyrimidin-5-yl)picolinonitrile | — | — | <3 | ++ |
| 150 | 2-(4-(2-((1s,4s)-4-methylcyclohexylamino)-4-(tetrahydrofuran-3-yloxy) pyrimidin-5-yl)phenoxy) acetonitrile | >10 | +++ | — | — |
| 201 | 5-(2,3-dihydrobenzo[b][1,4] dioxin-6-yl)-N-((1s,4S)-4-methylcyclohexyl)-4-((R)-tetrahydrofuran-3-yloxy) pyrimidin-2-amine | ~10 | +++ | — | — |

*vehicle treated
**N-(2-(5-chloro-2-methoxyphenylamino)-4'-methyl-4,5'-bithiazol-2'-yl)benzamide treated

REFERENCES

All publications and patents mentioned herein, including those items listed below, are hereby incorporated by reference in their entirety as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:
1. A compound of formula I:

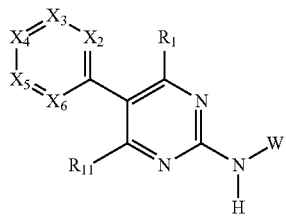

including a pharmaceutically acceptable salt, prodrug or N-oxide thereof, wherein:

$X_2$ is $CR_2$ or N, $X_3$ is $CR_3$ or N, $X_4$ is $CR_4$ or N, $X_5$ is $CR_5$ or N, and $X_6$ is $CR_6$ or N, where no more than two of $X_2$-$X_6$ are N;

W is $C_4$-$C_{10}$cycloalkyl substituted with one or two substituents independently selected from the group consisting of $C_1$-$C_6$alkyl, $C_3$-$C_{10}$cycloalkyl, —$OC_1$-$C_6$alkyl, —O—$C_3$-$C_{10}$cycloalkyl, —$CF_3$, and fluoro;

$R_1$ and $R_{11}$ are independently hydrogen, $C_1$-$C_6$alkyl, $C_3$-$C_{10}$cycloalkyl, $C_3$-$C_{10}$heterocycloalkyl, —$OC_1$-$C_6$alkyl-O—$C_1$-$C_{10}$cycloalkyl, —O—$C_1$-

$C_{10}$heterocycloalkyl, $-O-C(R_{12})(R_{13})-C_1$-$C_{10}$heterocycloalkyl, —O-aryl, —O-heteroaryl, $-O-C(R_{12})(R_{13})$-aryl, or $-O-C(R_{12})(R_{13})$-heteroaryl;

$R_2$ and $R_6$ are independently hydrogen, F, Br, I, —CF$_3$, —OCF$_3$, —OCHF$_2$, —OCH$_2$F, $C_2$-$C_6$alkyl, $C_3$-$C_{10}$cycloalkyl, $C_3$-$C_{10}$heterocyclyl, —O$C_1$-$C_6$alkyl, —O—$C_3$-$C_{10}$cycloalkyl, —CN, aryl, or heteroaryl;

$R_3$ and $R_5$ are independently hydrogen, halogen, —CF$_3$, —OCF$_3$, —OCHF$_2$, —OCH$_2$F, $C_1$-$C_6$alkyl, $C_3$-$C_{10}$cycloalkyl, $C_3$-$C_{10}$heterocyclyl, —O$C_1$-$C_6$alkyl, —O—$C_3$-$C_{10}$cycloalkyl, —CN, aryl, or heteroaryl;

$R_4$ is hydrogen, F, Cl, Br, I, —CF$_3$, —CN, —OCHF$_2$, —OCH$_2$F, —OCF$_3$, $C_1$-$C_{10}$alkyl, $C_3$-$C_{10}$cycloalkyl, $C_3$-$C_{10}$heterocyclyl, —O$C_1$-$C_{10}$alkyl, —O$C_3$-$C_{10}$cycloalkyl, —O$C_3$-$C_{10}$heterocycloalkyl, —S$C_1$-$C_{10}$alkyl, —S$C_3$-$C_{10}$cycloalkyl, aryl, or heteroaryl;

$R_{12}$ and $R_{13}$ each represent independently for each occurrence H, methyl, ethyl, n-propyl, isopropyl, or cyclopropyl;

n is 1, 2, or 3;

where at least one of $R_2$, $R_3$, $R_4$, $R_5$, and $R_6$ is not hydrogen; where $R_3$ is not morpholino or pyridyl; and where if $R_4$ is —CH$_3$, —OCF$_3$, —OCH$_3$, F, or Cl, then W is not unsubstituted cyclohexyl or unsubstituted cyclopropyl, or $R_1$ is not hydrogen.

2. The compound of claim 1, wherein $X_2$ is $CR_2$, $X_3$ is $CR_3$ or N, $X_4$ is $CR_4$, $X_5$ is $CR_5$, and $X_6$ is $CR_6$.

3. The compound of claim 1, wherein W is $C_4$-$C_{10}$cycloalkyl substituted with one or two substituents independently selected from the group consisting of $C_1$-$C_6$alkyl and fluoro.

4. The compound of claim 1, wherein W is cyclohexyl substituted with $C_1$-$C_6$alkyl.

5. The compound of claim 1, wherein $R_1$ and $R_{11}$ are independently hydrogen, $C_1$-$C_6$alkyl, $C_3$-$C_{10}$cycloalkyl, $C_3$-$C_{10}$heterocycloalkyl, —O$C_1$-$C_6$alkyl, —O—$C_3$-$C_{10}$cycloalkyl, —O—$C_3$-$C_{10}$heterocycloalkyl, or —O—C$(R_{12})(R_{13})$—$C_3$-$C_{10}$heterocycloalkyl.

6. The compound of claim 1, wherein $R_1$ is methoxy, ethoxy, propoxy, t-butoxy, cyclobutoxy, morpholinyl, —O-tetrahydrofuranyl, —O—CH$_2$-tetrahydrofuranyl, —O-tetrahydropyranyl, —O—CH$_2$-tetrahydropyranyl, —O-oxetanyl, —O—CH$_2$-oxetanyl, phenoxy or benzyloxy; and $R_{11}$ is hydrogen or methyl.

7. The compound of claim 1, wherein $R_2$ and $R_6$ are hydrogen.

8. The compound of claim 1, wherein $R_3$ and $R_5$ are hydrogen or halogen.

9. The compound of claim 1, wherein $R_4$ is —CF$_3$, —OCHF$_2$, —OCH$_2$F, —OCF$_3$, $C_1$-$C_6$alkyl, $C_3$-$C_{10}$cycloalkyl, $C_3$-$C_{10}$heterocyclyl, —O$C_1$-$C_6$alkyl, —O$C_3$-$C_{10}$cycloalkyl, or —O$C_3$-$C_{10}$heterocycloalkyl.

10. The compound of claim 1, wherein the compound is represented by formula Ia:

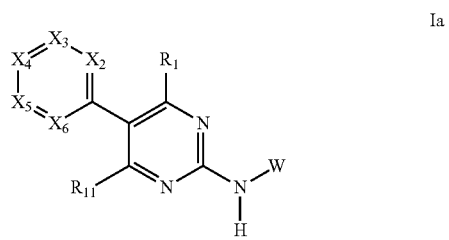

including a pharmaceutically acceptable salt thereof, wherein:

$X_2$ is $CR_2$, $X_3$ is $CR_3$, $X_4$ is $CR_4$, $X_5$ is $CR_5$, and $X_6$ is $CR_6$;

W is $C_4$-$C_{10}$cycloalkyl substituted with one or two substituents independently selected from the group consisting of $C_1$-$C_6$alkyl, $C_3$-$C_{10}$cycloalkyl, —O$C_1$-$C_6$alkyl, —O—$C_3$-$C_{10}$cycloalkyl, —CF$_3$, and fluoro;

$R_1$ and $R_{11}$ are independently hydrogen, $C_1$-$C_6$alkyl, $C_3$-$C_{10}$cycloalkyl, —O$C_1$-$C_6$alkyl, or —O—$C_3$-$C_{10}$cycloalkyl;

$R_2$ and $R_6$ are independently hydrogen, F, Br, I, —CF$_3$, —OCF$_3$, —OCHF$_2$, —OCH$_2$F, —O$C_1$-$C_6$alkyl, or —O—$C_3$-$C_{10}$cycloalkyl;

$R_3$ and $R_5$ are independently hydrogen, halogen, —CF$_3$, —OCF$_3$, —OCHF$_2$, —OCH$_2$F, —O$C_1$-$C_6$alkyl, or —O—$C_3$-$C_{10}$cycloalkyl; and $R_4$ is F, Cl, Br, I, —CF$_3$, —CN, —OCHF$_2$, —OCH$_2$F, —OCF$_3$, $C_3$-$C_{10}$heterocyclyl, —O$C_1$-$C_6$alkyl, —O$C_3$-$C_{10}$cycloalkyl, or heteroaryl.

11. The compound according to claim 10, wherein at least one of $R_1$ and $R_{11}$ is selected from the group consisting of hydrogen, $C_1$-$C_6$alkyl, —O—$C_1$-$C_6$alkyl, and —O—$C_3$-$C_{10}$cycloalkyl.

12. The compound of claim 10, wherein at least one of $R_1$ and $R_{11}$ is selected from the group consisting of hydrogen, —CH$_3$, —OCH$_3$, —O-isopropyl, —O-t-butyl, and —O-cyclobutyl.

13. A pharmaceutical composition comprising a compound of claim 1 and a pharmaceutically acceptable carrier.

* * * * *